(12) United States Patent
Shimomura et al.

(10) Patent No.: US 7,700,361 B2
(45) Date of Patent: Apr. 20, 2010

(54) SECRETORY OR MEMBRANE PROTEIN EXPRESSED IN SKELETAL MUSCLES

(75) Inventors: Iichirou Shimomura, 33-11, Higashitoyonakacho, 1-chome, Toyonaka-shi, Osaka, 560-0003 (JP); Yukio Yamada, Osaka (JP)

(73) Assignees: Takeda Pharmaceutical Company Limited, Osaka-Shi (JP); Iichirou Shimomura, Toyonaka-Shi (JP)

( * ) Notice: Subject to any disclaimer, the term of this patent is extended or adjusted under 35 U.S.C. 154(b) by 0 days.

(21) Appl. No.: 10/561,144

(22) PCT Filed: Jun. 15, 2004

(86) PCT No.: PCT/JP2004/008699
§ 371 (c)(1),
(2), (4) Date: Oct. 17, 2006

(87) PCT Pub. No.: WO2004/111234
PCT Pub. Date: Dec. 23, 2004

(65) Prior Publication Data
US 2007/0042374 A1 Feb. 22, 2007

(51) Int. Cl.
*G01N 33/00* (2006.01)
*A61K 39/00* (2006.01)

(52) U.S. Cl. .................... 436/86; 436/87; 424/198.1
(58) Field of Classification Search ................ None
See application file for complete search history.

(56) References Cited

U.S. PATENT DOCUMENTS

2003/0125258 A1* 7/2003 Lanctot et al. ............... 514/12

FOREIGN PATENT DOCUMENTS

| EP | 1 033 401 | | 9/2000 |
|---|---|---|---|
| WO | WO-00/21990 | | 4/2000 |
| WO | WO/00/21990 | * | 4/2000 |
| WO | WO-03/054005 | | 7/2003 |

OTHER PUBLICATIONS

Ngo et al., in The Protein Folding Problem and Tertiary Structure Prediction, 1994, Merz et al. (ed.), Birkhauser, Boston, MA, pp. 433 and 492-495.*

Kisselev, Structure, vol. 10, pp. 8-9, 2002.*
Witkowski et al., Biochemistry, 38, 11643-11650, 1999.*
Wishart et al., Journal of Biological Chemistry, vol. 270, No. 45, pp. 26782-26785, 1995.*
Database Geneseq [Online] Aug. 21, 2000, "Human secreted expressed sequence tag SEQ ID No.507." Database accesion No. AAA41767.
Database EMBL [Online] Oct. 14, 2000, "BP250016B10F12 Soares normalized bovine placenta Bos taurus cDNA clone BP250016810F12 5', mRNA sequence." Database accession No. BF045261.
Database EMBL [Online] Jul. 8, 2002, "Homo sapiens 3 BAC RP11-656G9 (Roswell Park Cancer Institute Human BAC Library) complete sequence." Database accession No. AC126567.
G. Thomas, et al., "Osteocrin, a Novel Bone-specific Secreted Protein That Modulates the Osteoblast Phenotype", The Journal of Biological Chemistry, Dec. 2001, 278(50), pp. 50563-50571.
Ichiro Shimomura, et al., "Himan Shibo Saibo o Megutte Kiso Adipocytokine to Seikatsu Shukanbyo", Pharma Medica, 2002, 20(12), pp. 69-74.
GenBank database Accession No. XM-155941 (Feb. 24, 2003).
H. Nishizawa, et al., "Musclin, a Novel Skeletal Muscle-derived Secretory Factory", The Journal of Biological Chemistry, vol. 279, No. 19, 2004, pp. 19391-19395.
Y. Arita, et al., "Paradoxical Decrease of an Adipose-Specific Protein, Adiponectin, in Obesity", Biochemical and Biophysical Research Communications, vol. 257, 1999, pp. 79-83.
K. Hotta, et al., "Circulating Concentrations of the Adipocyte Protein Adiponectin Are Decreased in Parallel With Reduced Insulin Sensitivity During the Progression to Type 2 Diabetes in Rhesus Monkeys," Diabetes, vol. 50, May 2001, 1126-1133.
C. M. Steppan, et al., "The hormone resistin links obesity to diabetes", Nature, vol. 409, Jan. 18, 2001, pp. 307-312.
I. Shimomura, et al., "Enhanced expression of PAI-1 in visceral fat: Possible contributor to vascular disease in obesity", Nature Medicine, vol. 2, Nov. 7, Jul. 1996, pp. 800-803.

* cited by examiner

Primary Examiner—Suzanne M. Noakes
Assistant Examiner—Jae W Lee
(74) Attorney, Agent, or Firm—Edwards Angell Palmer & Dodge LLP; David G. Conlin; Lisa Swiszez

(57) ABSTRACT

The present invention provides a novel secretory or membrane protein expressed specifically in skeletal muscles, a nucleic acid encoding the same, an antibody against the same, useful as a prophylactic/therapeutic agent or diagnostic agent for a disease associated with an abnormality of differentiation of skeletal muscle cell or metabolism function, or as a tool for screening a drug-candidate compound effective for the prophylaxis/treatment of the disease.

4 Claims, 10 Drawing Sheets

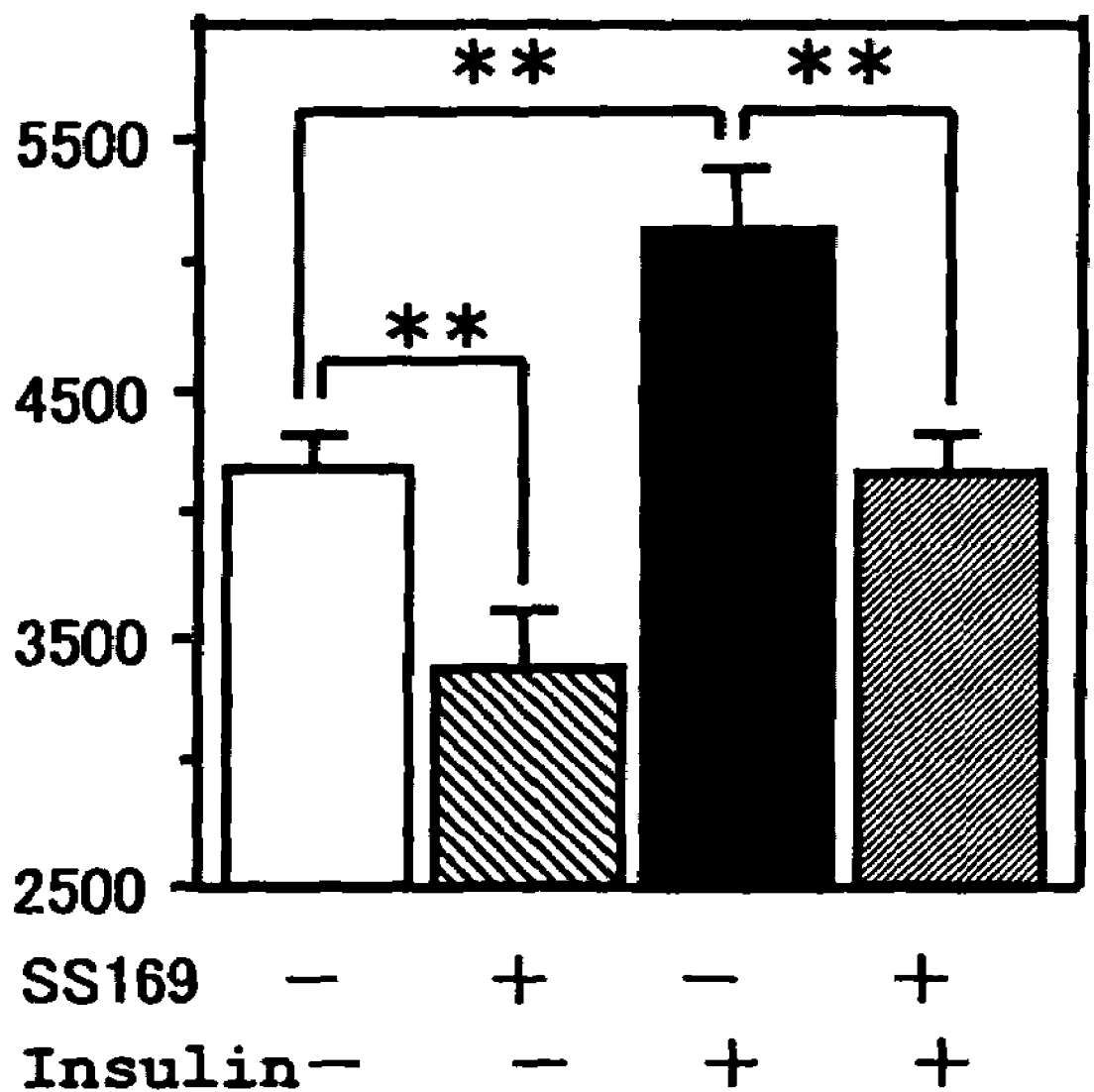

SECRETORY OR MEMBRANE PROTEIN EXPRESSED IN SKELETAL MUSCLES

CROSS-REFERENCE TO PRIOR APPLICATIONS

This application is a 35 USC § 371 national phase filing of international application number PCT/JP2004/008699, which has an international filing date of 15 Jun. 2004 and a claimed priority date of 16 Jun. 2003 and which is incorporated herein by reference. The claimed priority date is based on Japanese Patent Application Numbers 2003-171188 (filed 16 Jun. 2003), 2003-391047 (filed 20 Nov. 2003), 2004-023557 (filed 30 Jan. 2004), and 2004-030988 (filed 6 Feb. 2004), which are incorporated herein by reference.

TECHNICAL FIELD

The present invention relates to a novel secretory or membrane protein expressed specifically in skeletal muscles, a nucleic acid encoding the same, an antibody against the same, and uses thereof.

BACKGROUND ART

Lifestyle-related diseases such as diabetes mellitus, hyperlipemia, hypertension, and ischemic heart disease represent the major cause of oppressing the medical finances in advanced countries, including Japan. Modern people are liable to overeating and underexcersise; as a result, excess energy is accumulated in adipose tissue as neutral fats, which in turn causes obesity.

In recent years, it has been shown that various physiologically active proteins secreted from adipose tissue (generically referred to as adipocytokines) mediate metabolic regulation and insulin resistance, and their application to the treatment of lifestyle-related diseases has been attempted. For example, adiponectin was identified as an adipocytokine that occurs at high concentrations in blood, the secretion of which decreases with the increase in visceral fat (non-patent document 1), and it has been suggested that the decrease in the secretion of this hormone and the reduction in insulin action may be closely associated with each other (non-patent document 2). On the other hand, resistin was identified as a hormone secreted from adipocytes, which decreases the insulin action in adipose tissue, skeletal muscles, liver and the like (non-patent document 3), and is drawing attention as an adipocytokine closely associated with the onset of insulin resistance. Also, it has been shown that if fat accumulation occurs, plasminogen activator inhibitor-1 (PAI-1) is expressed remarkably in visceral fat and its blood concentration increases, which can be a cause of vascular complications (non-patent document 4).

Fat accumulation in obesity also occurs in the liver, muscles, pancreas, vascular walls and the like, and causes metabolic abnormalities in these organs, resulting in the onset of insulin resistance, diabetes mellitus, hyperlipemia, hypertension and the like. These organs are considered to be mutually associated via endocrine factors to achieve complex and sophisticated metabolic regulation. It is postulated, therefore, that endocrine factors acting like adipocytokines are also produced and secreted from muscles, liver, small intestine, blood vessels and the like, but to date there have been almost no reports on such factors.

Non-patent document 1: Arita et al., "Biochemical and Biophysical Research Communication", (USA), 1999, Vol. 257, pp. 79-83

Non-patent document 2: Hotta et al., "Diabetes," (USA), 2001, Vol. 50, pp. 1126-1133

Non-patent document 3: Steppan et al., "Nature," (UK), 2001, Vol. 409, pp. 307-312

Non-patent document 4: Shimomura et al., "Nature Medicine", (USA), 1996, Vol. 2, pp. 800-803

DISCLOSURE OF INVENTION

It is an object of the present invention to identify a novel muscle-derived secretory or membrane protein that can serve as a useful tool for the development of prophylactic/therapeutic drugs for diseases associated with sugar/lipid metabolic abnormalities, including what are called lifestyle-related diseases such as obesity, diabetes mellitus, and arteriosclerosis, or as a useful diagnostic marker for these diseases, and a gene encoding the same. It is another object of the present invention to provide a recombination vector comprising the gene, a transformant bearing the recombination vector, a method of producing the secretory or membrane protein by culturing the transformant, an antibody against the secretory or membrane protein, a compound that changes the expression amount of the secretory or membrane protein, a method of identifying a substance capable of interacting with the secretory or membrane protein (receptor or ligand), a method of screening a compound that changes the bindability between the substance and the secretory or membrane protein (antagonist, agonist) and a kit therefor, a compound that changes the bindability between the substance and the secretory or membrane protein, which is obtained using the screening method or screening kit, a pharmaceutical containing a compound that changes the bindability between the substance and the secretory or membrane protein or a compound that changes the expression amount of the secretory or membrane protein, and the like.

With the aim of accomplishing the above-described objectives, the present inventors prepared a cDNA library derived from mouse skeletal muscle, constructed a retrovirus expression library incorporating the cDNA on the 5' side of a cDNA of a constantly active thrombopoietin receptor (serine at 498 position substituted by asparagine) lacking the extracellular region at the N-terminus, collected high-titer retrovirus from packaging cells, infected the mouse proB cell line (Ba/F3) with the retrovirus, and selected cells retaining growing capacity. Genomic DNA was extracted from the selected cells, the introduced cDNA fragment derived from mouse skeletal muscle was subcloned using a PCR method, and the base sequence thereof was determined. cDNA clones containing the full-length protein-coding region were isolated from mouse, rat and human skeletal muscle cDNAs using the cDNA fragment obtained, and the base sequences thereof were determined; all these cDNA clones were found to be novel genes. The present inventors conducted further investigations based on these findings, and developed the present invention.

Accordingly, the present invention provides:

[1] a protein comprising the same or substantially the same amino acid sequence as the amino acid sequence starting at Amino Acid No. 1 in the amino acid sequence shown by SEQ ID NO:2 or 4 or a salt thereof,

[2] the protein described in [1] above, which comprises the same or substantially the same amino acid sequence as the amino acid sequence starting at Amino Acid No. 1 in the amino acid sequence shown by SEQ ID NO:2 or 4 or a salt thereof,

[3] a partial peptide of the protein described in [1] above or a salt thereof,

[4] a nucleic acid comprising a base sequence encoding the protein described in [1] above,

[5] the nucleic acid described in [4] above, which comprises the base sequence starting at Base No. 88 in the base sequence shown by SEQ ID NO:1 or 3 (if the nucleic acid is an RNA, however, the base shown by the symbol t in the base sequence is replaced with "u"),

[6] a nucleic acid comprising a base sequence encoding a polypeptide comprising the same or substantially the same amino acid sequence as the amino acid sequence shown by SEQ ID NO:2 or 4, or a portion thereof,

[7] a recombination vector comprising the nucleic acid described in [4] above,

[8] a transformant obtained by transforming a host cell with the recombination vector described in [7] above,

[9] a method of producing the protein described in [1] above or a salt thereof, which comprises culturing the transformant described in [8] above to produce the protein or a salt thereof,

[10] a pharmaceutical containing the protein described in [1] above or the partial peptide described in [3] above or a salt thereof,

[11] a pharmaceutical containing the nucleic acid described in [4] above,

[12] the pharmaceutical described in [10] or [11] above, which is a prophylactic/therapeutic agent for a disease involved in differentiation of skeletal muscle cell and/or metabolic abnormality,

[13] the pharmaceutical described in [12] above, wherein the metabolic abnormality is a sugar/lipid metabolic abnormality,

[14] a prophylactic/therapeutic method for a disease involved in differentiation of skeletal muscle cell and/or metabolic abnormality, which comprises administering an effective amount of the protein described in [1] above, the partial peptide described in [3] above or a salt thereof, or the nucleic acid described in [4] above, to a mammal,

[15] the method described in [14] above, wherein the metabolic abnormality is a sugar/lipid metabolic abnormality,

[16] a use of the protein described in [1] above, the partial peptide described in [3] above or a salt thereof, or the nucleic acid described in [4] above, which is for producing a prophylactic/therapeutic agent for a disease involved in differentiation of skeletal muscle cell and/or metabolic abnormality,

[17] the use described in [16] above, wherein the metabolic abnormality is a sugar/lipid metabolic abnormality,

[18] a diagnostic reagent containing the nucleic acid described in [6] above,

[19] an antibody against the protein described in [1] above or the partial peptide described in [3] above or a salt thereof,

[20] a diagnostic reagent containing the antibody described in [19] above,

[21] the diagnostic reagent described in [18] or [20] above, which is for diagnosing a disease involved in differentiation of skeletal muscle cell and/or metabolic abnormality,

[22] a pharmaceutical containing the antibody described in [19] above,

[23] a nucleic acid comprising a base sequence complementary to the base sequence encoding a polypeptide comprising the same or substantially the same amino acid sequence as the amino acid sequence shown by SEQ ID NO:2 or 4, or a portion thereof,

[24] a pharmaceutical containing the nucleic acid described in [23] above,

[25] the pharmaceutical described in [22] or [24] above, which is a prophylactic/therapeutic agent for a disease involved in differentiation of skeletal muscle cell and/or metabolic abnormality,

[26] the pharmaceutical described in [25] above, wherein the metabolic abnormality is a sugar/lipid metabolic abnormality,

[27] a prophylactic/therapeutic method for a disease involved in differentiation of skeletal muscle cell and/or metabolic abnormality, which comprises administering an effective amount of the antibody described in [19] above or the nucleic acid described in [23] above to a mammal,

[28] the method described in [27] above, wherein the metabolic abnormality is a sugar/lipid metabolic abnormality,

[29] a use of the antibody described in [19] above or the nucleic acid described in [23] above, which is for producing a prophylactic/therapeutic agent for a disease involved in differentiation of skeletal muscle cell and/or metabolic abnormality,

[30] the use described in [29] above, wherein the metabolic abnormality is a sugar/lipid metabolic abnormality,

[31] a screening method for a prophylactic/therapeutic substance for a disease involved in differentiation of skeletal muscle cell and/or metabolic abnormality, which comprises using the protein described in [1] above or the partial peptide described in [3] above or a salt thereof,

[32] the screening method described in [31] above, wherein the metabolic abnormality is a sugar/lipid metabolic abnormality,

[33] a screening kit for a prophylactic/therapeutic substance for a disease involved in differentiation of skeletal muscle cell and/or metabolic abnormality, which comprises the protein described in [1] above or the partial peptide described in [3] above or a salt thereof,

[34] the screening kit described in [33] above, wherein the metabolic abnormality is a sugar/lipid metabolic abnormality,

[35] a screening method for a prophylactic/therapeutic substance for a disease involved in differentiation of skeletal muscle cell and/or metabolic abnormality, which comprises using the nucleic acid described in [4] above,

[36] the screening method described in [35] above, wherein the metabolic abnormality is a sugar/lipid metabolic abnormality,

[37] a screening kit for a prophylactic/therapeutic substance for a disease involved in differentiation of skeletal muscle cell and/or metabolic abnormality, which comprises the nucleic acid described in [4] above,

[38] the screening kit described in [37] above, wherein the metabolic abnormality is a sugar/lipid metabolic abnormality,

[39] a prophylactic/therapeutic agent for a disease involved in differentiation of skeletal muscle cell and/or metabolic abnormality, which contains a regulator of the protein described in [1] above or a salt thereof,

[40] the prophylactic/therapeutic agent described in [39] above, wherein the metabolic abnormality is a sugar/lipid metabolic abnormality,

[41] a prophylactic/therapeutic method for a disease involved in differentiation of skeletal muscle cell and/or metabolic abnormality, which comprises administering an effective amount of a regulator of the protein described in [1] above or a salt thereof to a mammal,

[42] the method described in [41] above, wherein the metabolic abnormality is a sugar/lipid metabolic abnormality,

[43] a use of a regulator of the protein described in [1] above or a salt thereof for producing a prophylactic/therapeutic agent for a disease involved in differentiation of skeletal muscle cell and/or metabolic abnormality,

[44] the use described in [43] above, wherein the metabolic abnormality is a sugar/lipid metabolic abnormality, and the like.

The protein of the present invention, which is encoded by a skeletal muscle-derived gene, is a secretory or membrane protein expressed specifically in skeletal muscle cells in a feeding state and in diabetes mellitus and obesity, and has effects such as regulation of differentiation of skeletal muscle cell and sugar/lipid metabolic function.

BRIEF DESCRIPTION OF THE DRAWINGS

FIG. 15 shows the effects of SS169 on glycogen synthesis in C2C12 cells with and without insulin stimulation. The ordinate indicates D-[1–$^{14}$C]glucose uptake (cpm/mg protein) in the glycogen fraction within C2C12 cells; ** indicates $p<0.001$.

BEST MODE OF EMBODIMENT OF THE INVENTION

Figure 1:
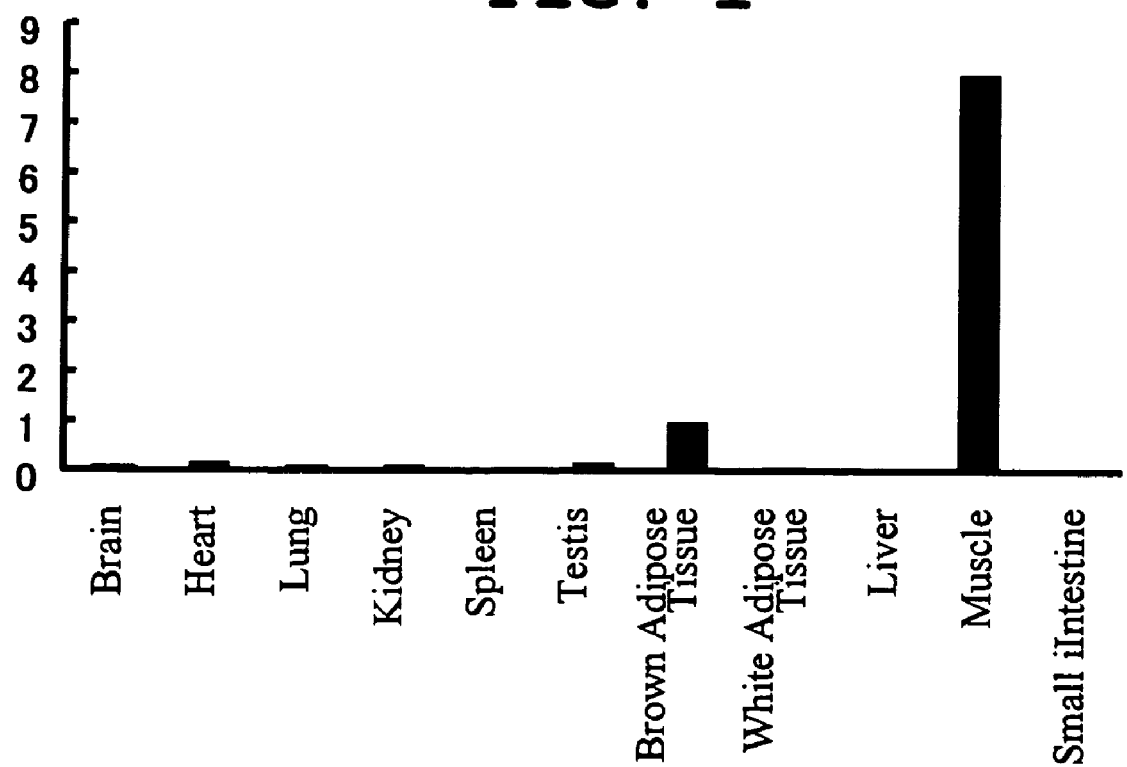
FIG. 1 shows the tissue distribution of the expression of the mouse SS169 gene [the brain, heart, lung, kidney, spleen, testis, brown adipose tissue, white adipose tissue, liver, muscles and small intestine are shown from the left]. The ordinate indicates an arbitrary unit.

The protein of the present invention is a protein comprising the same or substantially the same amino acid sequence as the amino acid sequence starting at Amino Acid No. 1 in the amino acid sequence shown by SEQ ID NO:2 or 4.

The protein of the present invention is a secretory or membrane protein particularly highly expressed in mammalian skeletal muscles (weakly expressed in brown adipose tissue) (the protein of the present invention is hereinafter sometimes referred to as "SS169"), and is not subject to limitation as to the source thereof, as long as it has the above-described properties; for example, the protein of the present invention may be a protein isolated and purified from cells [for example, liver cells, splenocytes, nerve cells, glial cells, β cells of pancreas, bone marrow cells, mesangial cells, Langerhans' cells, epidermic cells, epithelial cells, goblet cells, endothelial cells, smooth muscle cells, fibroblasts, fibrocytes, myocytes, adipocytes, immune cells (e.g., macrophages, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocytes or interstitial cells, or corresponding precursor cells, stem cells, cancer cells, and the like], or from any tissues where these cells are present [for example, brain, brain regions (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gallbladder, bone marrow, adrenal gland, skin, lung, gastrointestinal organs (e.g., large intestine, small intestine), blood vessels, heart, thymus, spleen, submandibular gland, peripheral blood, prostate, testis, ovary, placenta, uterus, bone, joints, adipose tissues (e.g., brown adipose tissue, white adipose tissue), skeletal muscles and the like] of mammals (for example, humans, mice, rats, rabbits, sheep, swine, cattle, horses, cats, dogs, monkeys, chimpanzee and the like) and the like. The protein may also be a chemically synthesized protein or a protein biochemically synthesized using a cell-free translation system, or a recombinant protein produced from a transformant incorporating a nucleic acid having the base sequence encoding the above-described amino acid sequence.

As substantially the same amino acid sequence as the amino acid sequence starting at Amino Acid No. 1 in the amino acid sequence shown by SEQ ID NO:2 or 4, an amino acid sequence having a homology of about 70% or more, preferably about 80% or more, more preferably about 90% or more, and particularly preferably about 95% or more, to the amino acid sequence starting at Amino Acid No. 1 in the amino acid sequence shown by SEQ ID NO:2 or 4. As used herein, "homology" means the proportion (%) of the same and similar amino acid residues to all overlapping amino acid residues in the optimal alignment where two amino acid sequences are aligned using a mathematic algorithm known in the relevant technical field (preferably, the algorithm is such that a gap can be introduced into one or both of the sequences for the optimal alignment). "A similar amino acid" means an amino acid having similar physiochemical properties; as examples, amino acids classified under the same group, such as aromatic amino acids (Phe, Trp, Tyr), aliphatic amino acids (Ala, Leu, Ile, Val), polar amino acids (Gln, Asn), basic amino acids (Lys, Arg, His), acidic amino acids (Glu, Asp), amino acids having a hydroxy group (Ser, Thr), and amino acids having a small side chain (Gly, Ala, Ser, Thr, Met), can be mentioned. Substitution by such a similar amino acid is expected to produce no change in the phenotype of protein (i.e., conservative amino acid substitution). Specific examples of conservative amino acid substitution are known in the relevant technical field and described in various pieces of the literature (see, for example, Bowie et al., Science, 247: 1306-1310 (1990)).

Algorithms to determine the homology of an amino acid sequence include, for example, but are not limited to, the algorithm described in Karlin et al., Proc. Natl. Acad. Sci. USA, 90: 5873-5877 (1993) [the algorithm is incorporated in the NBLAST and XBLAST programs (version 2.0) (Altschul et al., Nucleic Acids Res., 25: 3389-3402 (1997))], the algorithm described in Needleman et al., J. Mol. Biol., 48: 444-453 (1970) [the algorithm is incorporated in the GAP program in the GCG software package], the algorithm described in Myers and Miller, CABIOS, 4: 11-17 (1988) [the algorithm is incorporated in the ALIGN program (version 2.0), which is part of the CGC sequence alignment software package], the algorithm described in Pearson et al., Proc. Natl. Acad. Sci. USA, 85: 2444-2448 (1988)-[the algorithm is incorporated in the FASTA program in the GCG software package] and the like.

More preferably, substantially the same amino acid sequence as the amino acid sequence starting at Amino Acid No. 1 in the amino acid sequence shown by SEQ ID NO:2 or 4 is an amino acid sequence having a homology of about 60% or more, preferably about 70% or more, more preferably about 80% or more, and particularly preferably about 90% or more, to the amino acid sequence starting at Amino Acid No. 1 in the amino acid sequence shown by SEQ ID NO:2 or 4.

The protein comprising substantially the same amino acid sequence as the amino acid sequence shown by SEQ ID NO:2 or 4 is preferably, for example, a protein comprising the same or substantially the same amino acid sequence as the aforementioned amino acid sequence shown by SEQ ID NO:2 or 4, and having substantially the same quality of activity as a protein comprising the amino acid sequence shown by SEQ ID NO:2 or 4, or the like.

As examples of substantially the same quality of activity, receptor- (or ligand)-binding activity, signal transmission activity and the like can be mentioned. "Substantially the same quality" means that the activities of the proteins are qualitatively (e.g., physiologically or pharmacologically) equivalent to each other. It is preferable, therefore, that activities such as receptor- (or ligand)-binding activity and signal transmission activity be equivalent to each other (e.g., about 0.5 to about 2 times), but quantitative factors such as the extent of these activities and the molecular weights of the proteins may be different.

A measurement of an activity such as receptor- (or ligand)-binding activity or signal transmission activity can be performed using a method known per se; for example, a measurement can be performed according to a method used in the method described below of identifying a biological substance having specific affinity (receptor or ligand) or of screening for an agonist or antagonist.

Examples of the protein of the present invention also include what are called muteins of proteins comprising (1) an amino acid sequence having one or two or more amino acids (preferably about 1 to 30, more preferably about 1 to 10, and still more preferably several (1 to 5) amino acids) deleted from the amino acid sequence starting at Amino Acid No. 1 in the amino acid sequence shown by SEQ ID NO:2 or 4, (2) an amino acid sequence having one or two or more amino acids (preferably about 1 to 30, more preferably about 1 to 10, and still more preferably several (1 to 5) amino acids) added to the amino acid sequence starting at Amino Acid No. 1 in the amino acid sequence shown by SEQ ID NO:2 or 4, (3) an amino acid sequence having one or two or more amino acids (preferably about 1 to 30, more preferably about 1 to 10, and still more preferably several (1 to 5) amino acids) inserted in the amino acid sequence starting at Amino Acid No. 1 in the amino acid sequence shown by SEQ ID NO:2 or 4, (4) an amino acid sequence having one or two or more amino acids (preferably about 1 to 30, more preferably about 1 to 10, and still more preferably several (1 to 5) amino acids) substituted with other amino acids in the amino acid sequence starting at Amino Acid No. 1 in the amino acid sequence shown by SEQ ID NO:2 or 4, or (5) an amino acid sequence comprising a combination thereof, and the like.

When an amino acid sequence is inserted, deleted or substituted as described above, the position of the insertion, deletion or substitution is not subject to limitation, as long as the protein activities are retained.

The protein of the present invention is a secretory or membrane protein, and is translated as a precursor polypeptide having a signal peptide at the N-terminus in vivo, and then undergoes processing by signal peptidase to become a mature protein. The cleavage site of the signal peptide (N-terminus of the mature protein) can be determined by, for example, subjecting the fully or partially purified protein of the resent invention to Edman degradation, and can be estimated from the primary structure of the precursor polypeptide using a known mathematic algorithm. Such algorithms include, for example, but are not limited to, the algorithm described in Nielsen et al., Int. Neural Syst., 8 (5-6): 581-599 (1997) [the algorithm is incorporated in the Signal P program published in. e.g., *Identification of prokaryotic and eukaryotic signal peptides and prediction of their cleavage sites*, Henrik Nielsen, Jacob Engelbrecht, Søren Brunak and Gunnar von Heijne, Protein Engineering, 10:1-6, 1997; *Improved prediction of signal peptides*: SignalP 3.0, Jannick Dyrløv Bendtsen, Henrik Nielsen, Gunnar von Heijne and Søren Brunak. Mol. Biol., 340:783-795, 2004], the algorithm described in Emanuelsson et al., J. Mol. Biol. 300: 1005-1016 (2000) [the algorithm is incorporated in the Target P program published in *Predicting subcellular localization of proteins based on their N-terminal amino acid seguence*, Olof Emanuelsson, Henrik Nielsen, Søren Brunak and Gunnar von Heijne, J. Mel. Biol., 300: 1005-1016, 2000)]and the like. For example, when the SOSUI (Signal) program published in, e.g., *SOSUIsignal: Software System for Prediction of Signal Pentide and Membrane Protein*, Gomi M., Akazawa F., Mitaku S., Genome Informatics, 11 414-415 (2000); High performance system for signal peptide prediction: SOSUIsignal, Gomi M., Sonoyama M., and Mitaku S., Chem-Bie Info. J., 4 142-147 (2004)) is used, the polypeptide having the amino acid sequence shown by SEQ ID NO:2 or 4 is predicted to be cleaved between Amino Acid No. −1 and Amino Acid No. 1, but this does not always agree with the actual cleavage site, and the signal cleavage position can differ depending on the cell species that expresses the protein of the present invention. Therefore, amino acid sequences having one or two or more amino acids added to, or deleted from, the amino acid sequence starting at Amino Acid No. 1 in the amino acid sequence shown by SEQ ID NO:2 or 4 also include amino acid sequences having one or two or more amine acids added to the N-terminus thereof and amino acid sequences having one or two or more amino acids deleted from the N-terminus thereof.

The protein of the present invention is preferably the human SS169 protein having the amino acid sequence starting at Amino Acid No. 1 in the amino acid sequence shown by SEQ ID NO:2, the mouse SS169 protein having the amino acid sequence starting at Amino Acid No. 1 in the amino acid sequence shown by SEQ ID NO:4, or a homologue thereof in another mammal (e.g., rat homologue having the amino acid sequence starting at Amino Acid No.1 in the amino acid sequence shown by SEQ ID NO:23, and the like).

In the present specification, proteins and peptides are denoted with the N-terminus (amino terminus) described as the left end and the C-terminus (carboxyl terminus) as the right end, in accordance with the common way of describing peptides. The protein of the present invention (SS169), including a protein comprising the amino acid sequence starting at Amino Acid No.1 in the amino acid sequence shown by SEQ ID NO: 2 or 4, may have any of a carboxyl group (—COOH), a carboxylate (—COO⁻), an amide (—CONH$_2$) or an ester (—COOR) at the C-terminus thereof.

As used herein, R in the ester is exemplified by $C_{1-6}$ alkyl groups, for example, as methyl, ethyl, n-propyl, isopropyl, n-butyl and the like; $C_{3-8}$ cycloalkyl groups, for example, cyclopentyl, cyclohexyl and the like; $C_{6-12}$ aryl groups, for example, phenyl, α-naphthyl and the like; phenyl-$C_{1-2}$ alkyl groups, for example, benzyl, phenethyl and the like; $C_{7-14}$ aralkyl groups such as α-naphthyl-$C_{1-2}$-alkyl groups such as α-naphthylmethyl; pivaloyloxymethyl groups; and the like.

When the protein of the present invention has a carboxyl group (or carboxylate) at a position other than the C-terminus, the carboxyl group may be amidated or esterified, and such proteins are also included in the protein of the present invention. As examples of the ester used in this case, the above-described esters at the C-terminus can be mentioned.

Furthermore, the protein of the present invention also includes those wherein the amino group of the amino acid residue at the N-terminus is protected with a protecting group (for example, $C_{1-6}$ acyl groups such as $C_{1-6}$ alkanoyl groups such as formyl group and acetyl group); those wherein the glutamyl group at the N-terminus, which can be produced upon cleavage in vivo, is pyroglutaminated; those wherein a substituent (for example, —OH, —SH, amino group, imidazole group, indole group, guanidino group and the like) on the side chain of an amino acid in the molecule is protected with an appropriate protecting group (for example, $C_{1-6}$ acyl groups such as $C_{1-6}$ alkanoyl groups such as formyl group and acetyl group, and the like), conjugated proteins such as what are called glycoproteins having sugar chains bound thereto, and the like.

A partial peptide of SS169 (hereinafter sometimes simply abbreviated as "the partial peptide of the present invention") may be any peptide having the above-described partial amino acid sequence of SS169, and having substantially the same quality of activity to that of SS169. As used herein, "substantially the same quality of activity" has the same meaning as described above. A measurement of "substantially the same quality of activity" can be performed in the same manner as SS169.

Specifically, examples of the partial peptide of the present invention include one having a partial amino acid sequence further comprising a region involved in the binding of a biological substance capable of interacting with SS169 (receptor or ligand) and a region involved in the signal transduction mediated by the interaction, in the amino acid sequence starting at Amino Acid No. 1 in the amino acid sequence shown by SEQ ID NO:2 or 4.

The partial peptide of the present invention is preferably a peptide having at least 30 or more, preferably 60 or more, and more preferably 100 or more amino acids.

On the other hand, peptides comprising a partial amino acid sequence of SS169, but not having substantially the same quality of activity as SS169, for example, one having a partial amino acid sequence comprising a region involved in the binding of a biological substance capable of interacting with SS169 (receptor or ligand), but not comprising a region involved in the signal transduction mediated by the interaction, in the amino acid sequence starting at Amino Acid No. 1 in the amino acid sequence shown by SEQ ID NO:2 or 4, and the like, are not included in "the partial peptide of the present invention". However, because such peptides are capable of binding to a biological substance capable of interacting with SS169 (receptor or ligand) to block the signal transduction action of SS169, they can be useful for the prophylaxis/treatment of conditions/diseases involved in abnormal elevation of the signal transduction, and the like.

Also, the partial peptide of the present invention may have any of a carboxyl group (—COOH), a carboxylate (—COO⁻), an amide (—CONH₂), or an ester (—COOR) at the C-terminus thereof. As used herein, R in the ester is exemplified by the same examples as those mentioned with respect to SS169. When the partial peptide of the present invention has a carboxyl group (or carboxylate) at a position other than the C-terminus, the carboxyl group may be amidated or esterified, and such partial peptides are also included in the partial peptide of the present invention. In this case, the ester is exemplified by the same examples as those mentioned with respect to the ester at the C-terminus.

Furthermore, the partial peptide of the present invention, like the above-described SS169, also includes those wherein the amino group of the amino acid residue at the N-terminus is protected with a protecting group, those wherein the glutamine residue at the N-terminus is pyroglutaminated; those wherein a substituent on the side chain of an amino acid in the molecule is protected with an appropriate protecting group, conjugated peptides such as what are called glycopeptides having sugar chains bound thereto, and the like.

As the salt of SS169 or a partial peptide thereof, physiologically acceptable salts with acids or bases can be mentioned, with preference given to physiologically acceptable acid adduct salts. Examples of such salts include salts with inorganic acids (for example, hydrochloric acid, phosphoric acid, hydrobromic acid, sulfuric acid), salts with organic acids (for example, acetic acid, formic acid, propionic acid, fumaric acid, maleic acid, succinic acid, tartaric acid, citric acid, malic acid, oxalic acid, benzoic acid, methanesulfonic acid, benzenesulfonic acid), and the like.

SS169 or a salt thereof can be produced from cells or tissues of mammals described above by a method of protein purification known per se. Specifically, when SS169 is localized on the cell membrane, SS169 or a salt thereof can be prepared by homogenizing a tissue or cells of a mammal, removing the cell debris by low-speed centrifugation, centrifuging the supernatant at high speed to precipitate the cell membrane-containing fraction (if necessary, the cell membrane fraction is purified by density gradient centrifugation and the like), and subjecting the fraction to a chromatography such as reverse phase chromatography, ion exchange chromatography, or affinity chromatography, and the like. When SS169 is secreted extracellularly, SS169 or a salt thereof can be prepared by culturing a tissue or cells of a mammal in an appropriate medium, collecting the culture supernatant by filtration, centrifugation or the like, and subjecting the supernatant to a chromatography and the like in the same manner as described above.

SS169 or a partial peptide thereof or a salt thereof (hereinafter sometimes generically referred to as "SS169 species") can also be produced according to a known method of peptide synthesis.

The method of peptide synthesis may, for example, be any of solid phase synthesis and liquid phase synthesis. The desired protein can be produced by condensing a partial peptide or amino acids that can constitute an SS169 species and the remaining portion, and, when the product has a protecting group, removing the protecting group.

Condensation and protecting group removal can be achieved by methods known per se, for example, the methods described in (1) to (5) below.

(1) M. Bodanszky and M. A. Ondetti: Peptide Synthesis, Interscience Publishers, New York (1966)
(2) Schroeder and Luebke: The Peptide, Academic Press, New York (1965)
(3) Nobuo Izumiya et al.: Peptide Gosei-no-Kiso to Jikken (Basics and experiments of peptide synthesis), Maruzen Co. (1975)
(4) Haruaki Yajima and Shunpei Sakakibara: Seikagaku Jikken Koza (Biochemical Experiment) 1, Tanpakushitsu no Kagaku (Chemistry of Proteins) IV, 205 (1977)
(5) Haruaki Yajima ed.: Zoku Iyakuhin no Kaihatsu (A sequel to Development of Pharmaceuticals), Vol. 14, Peptide Synthesis, Hirokawa Shoten The protein (peptide) thus obtained can be purified and isolated using a known method of purification. Here, as examples of the method of purification, solvent extraction, distillation, column chromatography, liquid chromatography, recrystallization, combinations thereof and the like can be mentioned.

When the protein (peptide) obtained by the above-described method is the free form, the free form can be converted into an appropriate salt by a known method or a method based thereon; conversely, when the protein (peptide) is obtained in the form of a salt, the salt can be converted into the free form or another salt by a known method or a method based thereon.

To synthesize an SS169 species, ordinary commercially available resins for protein synthesis may be used. As examples of such resins, chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl)phenoxy resin and the like can be mentioned. Using such a resins, amino acids having α-amino groups and side-chain functional groups protected as appropriate are condensed on the resin in accordance with the sequence of the desired protein (peptide) according to various methods of condensation methods known per se. At the end of the reaction, the protein and the like are excised from the resin and the various protecting groups are removed simultaneously; then, an intramolecular disulfide bond-forming reaction is performed in a highly diluted solution to give the desired protein (peptide) or an amide thereof.

For the above-described condensation of protected amino acids, various activation reagents for protein synthesis may be used, with preference given to carbodiimides. Useful carbodiimides include DCC, N,N'-diisopropylcarbodiimide, N-ethyl-N'-(3-dimethylaminopropyl)carbodiimide and the like. For activation with these reagents, protected amino acids, along with a racemization inhibitor (for example, HOBt, HOOBt), may be added directly to the resin, or may be added to the resin after being previously activated in the form of a symmetric acid anhydride, HOBt ester, or HOOBt ester.

Solvents used in the activation of protected amino acids or condensation with the resin can be selected as appropriate from among solvents known to be usable for protein condensation reactions. For example, acid amides such as N,N-dimethylformamide, N,N-dimethylacetamide, and N-methylpyrrolidone; halogenated hydrocarbons such as methylene chloride and chloroform; alcohols such as trifluoroethanol; sulfoxides such as dimethylsulfoxide; amines such as pyridine; ethers such as dioxane and tetrahydrofuran; nitriles such as acetonitrile and propionitrile; esters such as methyl acetate and ethyl acetate; appropriate mixtures of these solvents, and the like can be used. Reaction temperature is selected as appropriate from the range known to be useful for protein binding reactions, and is normally selected as appropriate from the range of about −20° C. to 50° C. The activated amino acid derivative is normally used in an excess of 1.5 to 4 times.

If a test using the ninhydrin reaction reveals insufficient condensation, the condensation can be completed by repeating the condensation reaction without splitting off the protecting groups. If the condensation is yet insufficient even after repeating the reaction, unreacted amino acids can be acetylated with acetic anhydride or acetylimidazole.

Protection and protecting groups for the functional groups that should not involve the reaction of the starting materials, splitting off the protecting groups, activation of the functional groups involved in the reaction, and the like can be selected as appropriate from among known groups or known means.

Examples of the protecting groups for the amino groups of the starting materials include Z, Boc, tertiary pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc and the like.

A carboxyl group can be protected by, for example, alkyl esterification (for example, esterification with a linear, branched or cyclic alkyl such as methyl, ethyl, propyl, butyl, tertiary butyl, cyclopentyl, cyclohexyl, cycloheptyl, cyclooctyl, or 2-adamantyl), aralkyl esterification (for example, benzyl esterification, 4-nitrobenzyl esterification, 4-methoxybenzyl esterification, 4-chlorobenzyl esterification, benzhydryl esterification), phenacyl esterification, benzyloxycarbonyl hydrazidation, tertiary butoxycarbonyl hydrazidation, trityl hydrazidation and the like.

The hydroxyl group of serine can be protected by, for example, esterification or etherification. Examples of groups suitable for this esterification include lower alkanoyl groups such as acetyl group, aroyl groups such as benzoyl group, groups derived from carbonic acid, such as benzyloxycarbonyl group and ethoxycarbonyl group, and the like. As examples of groups suitable for the etherification, benzyl group, tetrahydropyranyl group, t-butyl group and the like can be mentioned.

Examples of the protecting group for the phenolic hydroxyl group of tyrosine include Bzl, $C_2$-Bzl, 2-nitrobenzyl, Br-Z, tertiary butyl and the like.

Examples of the protecting group for the imidazole moiety of histidine include Tos, 4-methoxy-2,3,6-trimethylbenzenesulfonyl, DNP, benzyloxymethyl, Bum, Boc, Trt, Fmoc and the like.

As examples of the method used to remove (split off) the protecting group, catalytic reduction in a hydrogen gas stream in the presence of a catalyst such as Pd-black or Pd-carbon; acid treatment with anhydrous hydrogen fluoride, methanesulfonic acid, trifluoromethanesulfonic acid or trifluoroacetic acid, or a mixed solution thereof; treatment with a base such as diisopropylethylamine, triethylamine, piperidine or piperazine; reduction with sodium in liquid ammonia, and the like can be mentioned. The reaction of splitting of the protecting group by the above-described acid treatment is normally performed at a temperature of about −20° C. to 40° C.; in the acid treatment, addition of a cation scavenger such as anisole, phenol, thioanisole, meta-cresol, para-cresol, dimethylsulfide, 1,4-butanedithiol or 1,2-ethanedithiol is effective. The 2,4-dinitrophenyl group used as the protecting group for the imidazole moiety of histidine is removed by thiophenol treatment; the formyl group used as the protecting group for the indole moiety of tryptophan is removed by alkali treatment with dilute sodium hydroxide solution, dilute ammonia or the like, as well as by the above-described acid treatment in the presence of 1,2-ethanedithiol, 1,4-butanedithiol or the like.

Examples of activated carboxyl groups in the starting material include corresponding acid anhydrides, azides, activated esters (esters with alcohols (for example, pentachlorophenol, 2,4,5-trichlorophenol, 2,4-dinitrophenol, cyanomethyl alcohol, para-nitrophenol, HONB, N-hydroxysuccimide, N-hydroxyphthalimide, HOBt)]. Examples of activated amino groups in the starting material include corresponding phosphoric amides.

In another method of obtaining an amide of the protein (peptide), for example, the α-carboxyl group of the carboxy-terminal amino acid is first protected by amidation, and the peptide chain on the amino group side is then extended to a desired length; thereafter, a protein (peptide) having only the protecting group for the N-terminal α-amino group in the peptide chain removed and a protein (peptide) having only the protecting group for the C-terminal carboxyl group removed are prepared, and the two proteins (peptides) are condensed in a mixed solvent as described above. Details of the condensation reaction are the same as those described above. After the protected protein (protected peptide) obtained by the condensation is purified, all the protecting groups are removed by the above-described method to give the desired crude protein (crude peptide). This crude protein (crude peptide) may be purified by various known means of purification, and the major fraction may be lyophilized to give an amide of the desired protein (peptide).

An ester of the protein (peptide) can be obtained by, for example, condensing the α-carboxyl group of the carboxy-terminal amino acid with a desired alcohol to prepare an amino acid ester, and then following the same procedures as those for the above-described amide of the protein (peptide).

The partial peptide of the present invention or a salt thereof can also be produced by cleaving SS169 or a salt thereof with an appropriate peptidase.

Furthermore, an SS169 species can also be produced by culturing a transformant comprising a nucleic acid encoding SS169 or a partial peptide thereof, and separating and purifying the SS169 species from the culture obtained. The nucleic acid encoding SS169 or a partial peptide thereof may be a DNA or RNA, or may be a DNA/RNA chimera. The nucleic acid is preferably a DNA. Also, the nucleic acid may be double stranded or single stranded. When the nucleic acid is double stranded, it may be a double-stranded DNA, a double-stranded RNA or a DNA:RNA hybrid. When the nucleic acid is single stranded, it may be a sense strand (i.e., code strand) or an antisense strand (i.e., non-code strand).

As the DNA encoding SS169 or a partial peptide thereof, genomic DNAs, genomic DNA libraries, cDNAs derived from any cells [for example, liver cells, splenocytes, nerve cells, glial cells, β cells of pancreas, bone marrow cells, mesangial cells, Langerhans' cells, epidermic cells, epithelial cells, goblet cells, endothelial cells, smooth muscle cells, fibroblasts, fibrocytes, myocytes, adipocytes, immune cells (e.g., macrophages, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocytes or interstitial cells, or corresponding precursor cells, stem cells, cancer cells, and the like], or any tissues where such cells are present [for example, brain, brain regions (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, lung, gastrointestinal organs (e.g., large intestine, small intestine), blood vessels, heart, thymus, spleen, submandibular gland, peripheral blood, prostate, testis, ovary, placenta, uterus, bone, joints, adipose tissues (e.g., brown adipose tissue, white adipose tissue), skeletal muscles and the like] of mammals (for example, humans, cattle, monkeys, horses, swine, sheep, goat, dogs, cats, guinea pigs, rats, mice, rabbits, hamsters and the like), cDNA libraries derived from the aforementioned cells/tissues, synthetic DNAs and the like can be mentioned. The vector used for the library may be any of bacteriophage, plasmid, cosmid, phagemid and the like. The DNA encoding SS169 or a partial peptide thereof can also be amplified directly by Reverse Transcriptase Polymerase Chain Reaction (hereinafter abbreviated as "the RT-PCR method") using a total RNA or mRNA fraction prepared from the above-described cells/tissues.

As examples of the DNA encoding SS169, a DNA encoding a protein comprising the base sequence starting at Base No. 88 in the base sequence shown by SEQ ID NO:1 or 3, a DNA comprising a base sequence that hybridizes with the base sequence starting at Base No. 88 in the base sequence shown by SEQ ID NO:1 or 3 under high stringent conditions, and having substantially the aforementioned same quality of activity as SS169 (e.g., receptor- (or ligand)-binding activity, signal transmission activity and the like), and the like can be mentioned.

As examples of the DNA capable of hybridizing under high stringent conditions with the base sequence starting at Base No. 88 in the base sequence shown by SEQ ID NO:1 or 3, a DNA comprising a base sequence having a homology of about 50% or more, preferably about 60% or more, more preferably about 70% or more, particularly preferably about 80% or more, and most preferably about 90% or more, to the base sequence starting at Base No. 88 in the base sequence shown by SEQ ID NO:1 or 3 and the like can be used.

The hybridization can be performed by a method known per se or a method based thereon, for example, the method described in Molecular Cloning, 2nd edition (J. Sambrook et al., Cold Spring Harbor Lab. Press, 1989) and the like. When a commercially available library is used, the hybridization can be performed according to the method described in the instruction manual attached. The hybridization can be performed preferably under highly stringent conditions.

As examples of the highly stringent conditions, conditions of a sodium salt concentration of about 19 mM to about 40 mM, preferably about 19 mM to about 20 mM, and a temperature of about 50° C. to about 70° C., preferably about 60° C. to about 65° C., and the like can be mentioned. In particular, the case of a sodium salt concentration of about 19 mM and a temperature of about 65° C. is preferred.

The DNA encoding SS169 is preferably a DNA comprising the base sequence encoding the mature human SS169 protein, shown by the base sequence starting at Base No. 88 in the base sequence shown by SEQ ID NO:1, more preferably a DNA having the base sequence encoding the human SS169 precursor polypeptide, shown by SEQ ID NO:1, or a DNA comprising the base sequence encoding the mature mouse SS169 protein, comprising the base sequence starting at Base No. 88 in the base sequence shown by SEQ ID NO:3, more preferably a DNA having the base sequence encoding the mouse SS169 precursor polypeptide, shown by SEQ ID NO:3, or a homologue thereof in another mammal (e.g., a DNA comprising the base sequence encoding the mature rat SS169 protein, comprising the base sequence starting at Base No. 88 in the base sequence shown by SEQ ID NO:22, preferably a DNA having the base sequence encoding the rat SS169 precursor polypeptide, shown by SEQ ID NO:23, and the like).

The DNA encoding the partial peptide of the present invention may be any one, as long as it comprises the base sequence encoding a peptide comprising the same or substantially the same amino acid sequence as a portion of the amino acid sequence starting at Amino Acid No. 1 in the amino acid sequence shown by SEQ ID NO:2 or 4. The DNA encoding the partial peptide of the present invention may also be any of genomic DNAs, genomic DNA libraries, cDNAs derived from the above-described cells/tissue, cDNA libraries derived from the above-described cells/tissue, and synthetic DNAs. The vector used for the library may be any of bacteriophage, plasmid, cosmid, phagemid and the like. The DNA encoding SS169 or a partial peptide thereof can also be amplified directly by the RT-PCR method using an mRNA fraction prepared from the above-described cells/tissues.

Specifically, as examples of the DNA encoding the partial peptide of the present invention, (1) a DNA comprising a partial base sequence of the base sequence starting at Base No.88 in the base sequence shown by SEQ ID NO:1 or 3, or (2) a DNA having a base sequence that hybridizes under high stringent conditions with a DNA having the base sequence starting at Base No.88 in the base sequence shown by SEQ ID NO:1 or 3, and encoding a peptide having substantially the aforementioned same quality of activity as SS169 (e.g., receptor- (or ligand)-binding activity, signal transmission activity and the like) and the like can be used.

As examples of the DNA capable of hybridizing under high stringent conditions with the base sequence starting at Base No. 88 in the base sequence shown by SEQ ID NO:1 or 3, a DNA comprising a base sequence having a homology of about 60% or more, preferably about 70% or more, more preferably about 80% or more, and most preferably about 90% or more, to the base sequence, and the like can be used.

The DNA encoding SS169 or a partial peptide thereof can be cloned by amplification by the PCR method using a synthetic DNA primer having a portion of the base sequence encoding the SS169 or a partial peptide thereof, or by hybridization of the DNA incorporated in an appropriate expression vector with a labeled DNA fragment or synthetic DNA encoding a portion or whole of the SS169 protein. The hybridization can be performed according to, for example, the method described in Molecular Cloning, 2nd edition (ibidem) and the like. When a commercially available library is used, the hybridization can be performed according to the method described in the instruction manual attached to the library.

The base sequence of the DNA can be converted by a method known per se such as the ODA-LA PCR method, the Gapped duplex method, or the Kunkel method, or a method based thereon, using a known kit, for example, Mutan™-super Express Km (Takara Shuzo Co., Ltd.), Mutan™-K (Takara Shuzo Co., Ltd.) and the like.

The cloned DNA can be used as is or, if desired, after digestion with a restriction enzyme or addition of a linker, depending on the purpose of use. The DNA may have ATG as a translation initiation codon at the 5' end thereof, and may have TAA, TGA or TAG as a translation termination codon at the 3' end thereof. These translation initiation and termination codons may be added using an appropriate synthetic DNA adapter.

An expression vector comprising the DNA encoding SS169 or a partial peptide thereof can be produced by, for example, excising the desired DNA fragment from the DNA encoding SS169, and joining the DNA fragment downstream of a promoter in an appropriate expression vector.

As the expression vector, plasmids derived from *Escherichia coli* (e.g., pBR322, pBR325, pUC12, pUC13); plasmids derived from *Bacillus subtilis* (e.g., pUB110, pTP5, pC194); plasmids derived from yeast (e.g., pSH19, pSH15); insect cell expression plasmids (e.g., pFast-Bac); animal cell expression plasmids (e.g., pA1-11, pXT1, pRc/CMV, pRc/RSV, pcDNAI/Neo); bacteriophages such as λ phage; insect virus vectors such as baculovirus (e.g., BmNPV, AcNPV); animal virus vectors such as retrovirus, vaccinia virus, and adenovirus, and the like can be used.

The promoter may be any promoter that matches well with the host used for gene expression.

For example, when the host is an animal cell, the SRα promoter, the SV40 promoter, the LTR promoter, the CMV (cytomegalovirus) promoter, the RSV (Rous sarcoma virus) promoter, the MoMuLV (Moloney mouse leukemia virus) LTR, the HSV-TK (herpes simplex virus thymidine kinase) promoter and the like can be used. In particular, the CMV promoter, the SRα promoter and the like are preferable.

When the host is a bacterium of the genus Escherichia, the trp promoter, the lac promoter, the recA promoter, the $\lambda P_L$ promoter, the lpp promoter, the T7 promoter and the like are preferable.

When the host is a bacterium of the genus Bacillus, the SPO1 promoter, the SPO2 promoter, the penP promoter and the like are preferable.

When the host is a yeast, the PHO5 promoter, the PGK promoter, the GAP promoter, the ADH promoter and the like are preferable.

When the host is an insect cell, the polyhedrin promoter, the P10 promoter and the like are preferable.

As the expression vector, one optionally comprising an enhancer, a splicing signal, a poly A-addition signal, a selection marker, an SV40 replication origin (hereinafter sometimes abbreviated as SV40 ori) and the like, in addition to the above-described examples, can be used. As examples of the selection marker, the dihydrofolate reductase gene (hereinafter sometimes abbreviated as dhfr, methotrexate (MTX) resistance), the ampicillin resistance gene (hereinafter sometimes abbreviated as amp$^r$), the neomycin resistance gene (hereinafter sometimes abbreviated as neo$^r$, G418 resistance) and the like can be mentioned. In particular, when Chinese hamster cells lacking the dhfr gene are used in combination with the dhfr gene as the selection marker, it is also possible to select the desired gene on a thymidine-free medium.

Also, a base sequence encoding a signal sequence (signal codon) that matches with the host may be added as necessary to the 5' end side of the DNA encoding SS169 or a partial peptide thereof (or substituted with a native signal codon). For example, when the host is a bacterium of the genus Escherichia, a PhoA signal sequence, a OmpA signal sequence and the like can be used; when the host is a bacterium of the genus Bacillus, an α-amylase signal sequence, a subtilisin signal sequence and the like can be used; when the host is a yeast, an MF α signal sequence, an SUC2 signal sequence and the like can be used; when the host is an animal cell, an insulin signal sequence, an α-interferon signal sequence, an antibody molecule signal sequence and the like can be used.

By transforming the host with the above-described expression vector comprising the DNA encoding SS169 or a partial peptide thereof, and culturing the transformant obtained, an SS169 species can be produced.

As examples of the host used, bacteria of the genus Escherichia, bacteria of the genus Bacillus, yeasts, insect cells, insects, animal cells and the like can be mentioned.

As examples of the bacteria of the genus Escherichia, Escherichia coli K12●DH1 [Proceedings of the National Academy of Sciences of the USA (Proc. Natl. Acad. Sci. USA), Vol. 60, 160 (1968)], Escherichia coli JM103 [Nucleic Acids Research, Vol. 9, 309 (1981)], Escherichia coli JA221 [Journal of Molecular Biology, Vol. 120, 517 (1978)], Escherichia coli HB101 [Journal of Molecular Biology, Vol. 41, 459 (1969)], Escherichia coli C600 [Genetics, Vol. 39, 440 (1954)] and the like can be used.

As examples of the bacteria of the genus Bacillus, Bacillus subtilis MI114 [Gene, Vol. 24, 255 (1983)], Bacillus subtilis 207-21 [Journal of Biochemistry, Vol. 95, 87 (1984)] and the like can be used.

As examples of the yeasts, Saccharomyces cerevisiae AH22, AH22R$^-$, NA87-11A, DKD-5D, and 20B-12, Schizosaccharomyces pombe NCYC1913 and NCYC2036, Pichia pastoris KM71 and the like can be used.

As the insect cells, an established cell line derived from the cabbage armyworm (Spodoptera frugiperda cells; Sf cells), MG1 cells derived from the Trichoplusia ni mid-intestine, High Five™ cells derived from Trichoplusia ni eggs, cells derived from Mamestra brassicae, cells derived from Estigmena acrea, and the like can be used when the virus is AcNPV, for example. When the virus is BmNPV, an established cell line derived from Bombyx mori (Bombyx mori N cells; BmN cells) and the like can be used as the insect cells. As examples of the Sf cells, Sf9 cells (ATCC CRL1711), Sf21 cells (both types of cells are described in Vaughn, J. L. et al., In Vivo, 13, 213-217 (1977)) and the like can be used.

As examples of the insects, Bombyx mori larvae and the like can be used [Maeda et al., Nature, Vol. 315, 592 (1985)].

As examples of the animal cells, monkey COS-7 cells, monkey Vero cells, Chinese hamster cells CHO (hereinafter abbreviated as CHO cells), Chinese hamster cells CHO lacking the dhfr gene (hereinafter abbreviated as CHO(dhfr$^-$) cells), mouse L cells, mouse AtT-20 cells, mouse myeloma cells, rat GH3 cells, human FL cells and the like can be used.

Transformation can be performed according to a known method depending on the kind of the host. Bacteria of the genus Escherichia can be transformed according to, for example, the methods described in Proceedings of the National Academy of Sciences of the USA (Proc. Natl. Acad. Sci. U.S.A.), Vol. 69, 2110 (1972), Gene, Vol. 17, 107 (1982) and the like.

Bacteria of the genus Bacillus can be transformed according to, for example, the methods described in Molecular & General Genetics, Vol. 168, 111 (1979) and the like.

Yeasts can be transformed according to, for example, the methods described in Methods in Enzymology, Vol. 194, 182-187 (1991), Proceedings of the National Academy of Sciences of the USA (Proc. Natl. Acad. Sci. U.S.A.), Vol. 75, 1929 (1978) and the like.

Insect cells and insects can be transformed according to, for example, the methods described in Bio/Technology, Vol. 6, 47-55 (1988) and the like.

Animal cells can be transformed, for example, according to the methods described in Saibo Kogaku (Cell Engineering), extra issue 8, Shin Saibo Kogaku Jikken Protocol (New Cell Engineering Experimental Protocol), 263-267 (1995), published by Shujunsha, and Virology, Vol. 52, 456 (1973).

Cultivation of a transformant can be performed according to a known method depending on the kind of the host.

For example, when culturing a transformant whose host is a bacterium of the genus Escherichia or Bacillus, the medium used for cultivation is preferably a liquid medium. The medium preferably contains substances required for the growth of the transformant, such as carbon sources, nitrogen sources, and inorganic substances. As examples of the carbon sources, glucose, dextrin, soluble starch, sucrose and the like can be mentioned; as examples of the nitrogen sources, inorganic or organic substances such as ammonium salts, nitrate salts, corn steep liquor, peptone, casein, meat extract, soybean cake, and potato extract can be mentioned; as examples of the inorganic substances, calcium chloride, sodium dihydrogenphosphate, magnesium chloride and the like can be mentioned. In addition, yeast extract, vitamins, growth promoting factors and the like may be added to the medium. The pH of the medium is preferably about 5 to about 8.

The medium for cultivation of a transformant whose host is a bacterium of the genus *Escherichia* is preferably, for example, an M9 medium containing glucose and Casamino acids [Miller, Journal of Experiments in Molecular Genetics, 431-433, Cold Spring Harbor Laboratory, New York, 1972]. Chemicals such as 3β-indolylacrylic acid may be added to the medium as necessary to allow the promoter to function efficiently.

Cultivation of a transformant whose host is a bacterium of the genus *Escherichia* is normally performed at about 15° C. to about 43° C. for about 3 to about 24 hours. The culture may be aerated or agitated as necessary.

Cultivation of a transformant whose host is a bacterium of the genus *Bacillus* is normally performed at about 30° C. to about 40° C. for about 6 to about 24 hours. The culture may be aerated or agitated as necessary.

As examples of the medium for culturing a transformant whose host is a yeast, Burkholder's minimal medium [Bostian, K. L. et al., Proceedings of the National Academy of Sciences of the USA (Proc. Natl. Acad. Sci. USA), Vol. 77, 4505 (1980)], an SD medium containing 0.5% Casamino acid [Bitter, G. A. et al., Proceedings of the National Academy of Sciences of the USA (Proc. Natl. Acad. Sci. USA), Vol. 81, 5330 (1984)] and the like can be mentioned. The pH of the medium is preferably about 5 to about 8. Cultivation is normally performed at about 20° C. to about 35° C. for about 24 to about 72 hours. The culture may be aerated or agitated as necessary.

As examples of the medium for culturing a transformant whose host is an insect cell or an insect, Grace's Insect Medium [Grace, T. C. C., Nature, Vol. 195, 788 (1962)] having additives such as 10% inactivated bovine serum added thereto as appropriate, and the like can be used. The pH of the medium is preferably about 6.2 to about 6.4. Cultivation is normally performed at about 27° C. for about 3 to about 5 days. The culture may be aerated or agitated as necessary.

As examples of the medium for culturing a transformant whose host is an animal cell, a minimal essential medium (MEM) containing about 5% to about 20% fetal bovine serum [Science, Vol. 122, 501 (1952)], Dulbecco's modified Eagle's medium (DMEM) [Virology, Vol. 8, 396 (1959)], RPMI 1640 medium [The Journal of the American Medical Association, Vol. 199, 519 (1967)], 199 medium [Proceeding of the Society for the Biological Medicine, Vol. 73, 1 (1950)] and the like can be used. The pH of the medium is preferably about 6 to about 8. Cultivation is normally performed at about 30° C. to about 40° C. for about 15 to about 60 hours. The culture may be aerated or agitated as necessary.

As described above, an SS169 species can be produced in or outside the cells of a transformant.

The SS169 species can be separated and purified from the culture obtained by culturing the aforementioned transformant according to a method known per se.

For example, when the SS169 species is extracted from the cytoplasm of cultured cells, a method that comprises suspending the cells collected from the culture by a known method in an appropriate buffer, disrupting the cells by ultrasonication, lysozyme and/or freeze-thawing and the like, and performing centrifugation and filtration, to yield a crude extract of the soluble protein, and the like can be used as appropriate. The buffer may contain a protein denaturant such as urea or guanidine hydrochloride and a surfactant such as Triton X-100™. On the other hand, when the SS169 species is extracted from a membrane fraction, a method that comprises disrupting cells in the same manner as described above, performing low-speed centrifugation to precipitate and remove cell debris, and centrifuging the supernatant at a high speed to precipitate a fraction containing the cell membrane (the cell membrane fraction is purified by density gradient centrifugation and the like as necessary) and the like can be used. When the SS169 species is secreted outside the cells, a method that comprises separating the culture supernatant from the culture by centrifugation, filtration or the like, and the like can be used.

The SS169 species contained in the soluble fraction, membrane fraction or culture supernatant thus obtained can be isolated and purified according to a method known per se. Such methods include methods based on differences in solubility, such as salting-out and solvent precipitation; methods based mainly on differences in molecular weight, such as dialysis, ultrafiltration, gel filtration, and SDS-polyacrylamide gel electrophoresis; methods based on differences in electric charge, such as ion exchange chromatography; methods based on specific affinity, such as affinity chromatography; methods based on differences in hydrophobicity, such as reverse phase high performance liquid chromatography; methods based on differences in isoelectric point, such as isoelectric focusing; and the like. These methods may be combined as appropriate.

When the protein or peptide thus obtained is in the free form, the free form can be converted into a salt by a method known per se or a method based thereon; when the protein or peptide is obtained in the form of a salt, the salt can be converted into the free form or another salt by a method known per se or a method based thereon.

The SS169 species produced by the transformant can be treated with a suitable protein-modifying enzyme before or after the purification, so as to make an optionally chosen modification or to partially remove a polypeptide. As examples of the protein-modifying enzyme used, trypsin, chymotrypsin, arginyl endopeptidase, protein kinase, glycosidase and the like can be mentioned.

The presence of the SS169 species thus obtained can be confirmed by an enzyme immunoassay, Western blotting and the like using a specific antibody.

Furthermore, an SS169 species can be synthesized in vitro using a cell-free protein translation system comprising rabbit reticulocyte lysate, wheat germ lysate, *Escherichia coli* lysate or the like, with an RNA corresponding to the DNA encoding the above-described SS169 or a partial peptide thereof as the template. Alternatively, an SS169 species can also be synthesized using a cell-free transcription/translation system further comprising RNA polymerase, with the DNA encoding SS169 or a partial peptide thereof as the template.

A nucleic acid comprising the base sequence encoding the SS169 protein or the initial translation product thereof, i.e., a polypeptide comprising the same or substantially the same amino acid sequence as the amino acid sequence shown by SEQ ID NO:2 or 4, or a portion thereof, or a base sequence complementary to the base sequence or a portion thereof, is meant to include not only the above-described nucleic acid encoding SS169 or a partial peptide thereof, but also base sequences comprising a mismatch frame.

A nucleic acid comprising a base sequence complementary to the target region of the desired nucleic acid, i.e., a nucleic acid capable of hybridizing with the desired nucleic acid, can be said to be "antisense" against the desired nucleic acid. On the other hand, a nucleic acid comprising a base sequence having a homology to the target region of the desired nucleic acid can be said to be "sense" against the target nucleic acid.

As used herein, "having a homology" or "(being) complementary" means having a homology or complementarity of about 70% or more, preferably about 80% or more, more preferably about 90% or more, and most preferably about 95% or more, between the base sequences.

A nucleic acid comprising a base sequence complementary to the base sequence encoding the SS169 protein or the initial translation product thereof or a portion thereof (hereinafter also referred to as "the antisense nucleic acid of the present invention") can be designed and synthesized on the basis of the base sequence information of a cloned or sequenced SS169-encoding nucleic acid. Such nucleic acids are capable of inhibiting the replication or expression of the SS169 gene. Hence, the antisense nucleic acid of the present invention is capable of hybridizing with the RNA transcribed from the SS169 gene, and of inhibiting the synthesis (processing) or function (translation into protein) of mRNA.

The target region of the antisense nucleic acid of the present invention is not subject to limitation as to length, as long as hybridization of the antisense nucleic acid results in the inhibition of the translation of the SS169 protein, and may be the whole sequence or a partial sequence of SS169 mRNA; for example, about 15 bases for the shortest and the whole sequence of mRNA or the initial transcription product for the longest can be mentioned. Considering the issues of the ease of synthesis and antigenicity, an oligonucleotide comprising about 15 to about 30 bases is preferred, but the length is not limited thereto. Specifically, for example, the 5'-end hairpin loop, 5'-end 6-base-pair repeat, 5'-end untranslated region, polypeptide translation initiation codon, protein coding region, ORF translation initiation codon, 3'-end untranslated region, 3'-end palindrome region, and 3'-end hairpin loop of the nucleic acid encoding the SS169 precursor polypeptide, may be selected as the target region, but any other region within the SS169 gene may also be selected as the target. For example, it is also preferable that the intron portion of the gene be the target region.

Furthermore, the antisense nucleic acid of the present invention may be capable of inhibiting RNA transcription by binding with the SS169 gene, which is a double-stranded DNA, to form a triple strand (triplex, as well as inhibiting translation into protein by hybridizing with SS169 mRNA or the initial transcription product.

Examples of the antisense nucleic acid include deoxypolynucleotides comprising 2-deoxy-D-ribose, ribonucleotides comprising D-ribose, other types of nucleotides which are N-glycosides of the purine or pyrimidine base, or other polymers having a non-nucleotide backbone (for example, commercially available nucleic acid polymers specific for protein nucleic acids and synthetic sequences) or other polymers comprising a special linkage (provided that the polymers comprise nucleotides having such an alignment that allows base pairing or base attachment, as found in DNA or RNA) and the like. These may be double-stranded DNAs; single-stranded DNAs, double-stranded RNAs, single-stranded RNAs, or DNA:RNA hybrids, and may also be unmodified polynucleotides (or unmodified oligonucleotides); those with known modifications, for example, those with labels known in the art, those with caps, those methylated, those with substitution of one or more naturally occurring nucleotides with their analogue, those with intramolecular modifications of nucleotides such as those with uncharged linkages (for example, methyl phosphonates, phosphotriesters, phosphoramidates, carbamates and the like) and those with charged linkages or sulfur-containing linkages (for example, phosphorothioates, phosphorodithioates and the like); those having side chain groups such as proteins (nucleases, nuclease inhibitors, toxins, antibodies, signal peptides, poly-L-lysine and the like) or saccharides (for example, monosaccharides and the like); those with intercalators (for example, acridine, psoralen and the like); those with chelators (for example, metals, radioactive metals, boron, oxidative metals and the like); those with alkylating agents; or those with modified linkages (for example, α anomeric nucleic acids and the like). As used herein, "nucleoside", "nucleotide" and "nucleic acid" may comprise not only the purine and pyrimidine bases, but also other modified heterocyclic bases. Such modified produced may comprise a methylated purine and pyrimidine, acylated purine and pyrimidine, and another heterocyclic ring. The modified nucleotide and modified nucleotide may have a modification in the sugar moiety thereof; for example, one or more hydroxyl groups may be substituted with halogens, aliphatic groups and the like, or may be converted into functional groups such as ethers and amines.

The antisense nucleic acid is an RNA, a DNA, or a modified nucleic acid (RNA, DNA). Specific examples of the modified nucleic acid include, but are not limited to, sulfur and thiophosphate derivatives of nucleic acids and those resistant to degradation of polynucleoside amides and oligonucleoside amides. The antisense nucleic acid of the present invention can be designed preferably on the following plan, that is, to increase the intracellular stability of the antisense nucleic acid, to increase the cell permeability of the antisense nucleic acid, to increase the affinity for the targeted sense strand, and to reduce the toxicity, if any, of the antisense nucleic acid. Many such modifications are known in the art, as disclosed in, for example, J. Kawakami, et al., Pharm. Tech. Japan, Vol. 8, p. 247, 1992; Vol. 8, p. 395, 1992; S. T. Crooke et al. ed., Antisense Research and Applications, CRC Press, 1993; and the like.

The antisense nucleic acid may comprise an altered or modified sugar, base, and bond, and can be supplied in a special form such as liposomes or microspheres, can be applied to gene therapy, and can be given in the form of an adduct. As substances for the adduct, polycations such as polylysine, which acts to neutralize the electric charge of the phosphate group backbone, and hydrophobic substances such as lipids that enhance the interaction with the cell membrane or increase nucleic acid uptake (for example, phospholipids, cholesterols and the like) can be mentioned. As lipids preferred for the adduct, cholesterol and derivatives thereof (for example, cholesteryl chloroformate, cholic acid and the like) can be mentioned. These substances may be attached to the 3' or 5' end of the nucleic acid, and can be attached via a base, sugar, or intramolecular nucleoside bond. As other groups, capping groups specifically placed at the 3' or 5' end of the nucleic acid to prevent its degradation by nucleases such as exonuclease and RNase, can be mentioned. Such capping groups include, but are not limited to, hydroxyl group protecting groups known in the art, including glycols such as polyethylene glycol and tetraethylene glycol.

Ribozymes capable of specifically cleaving SS169 mRNA or the initial transcription product thereof inside the coding region (comprising the intron moiety in the case of the initial transcription product) can also be included in the antisense nucleic acid of the present invention. "A ribozyme" refers to an RNA having enzyme activity to cleave nucleic acids; since it has recently been shown that oligo-DNAs having the base sequence of the enzyme activity moiety likewise have nucleic acid cleavage activity, this term is used herein as a concept including DNAs, as long as they have sequence-specific nucleic acid cleavage activity. The most versatile ribozymes include self-splicing RNAs found in infectious RNAs such as viroid and virusoid, and are known to occur in the hammerhead type, the hairpin type and the like. The hammerhead type exhibits enzyme activity with about 40 bases, and is capable of specifically cleaving only the target mRNA by rendering several bases at each end adjacent to the hammerhead structure moiety (about 10 bases in total) a sequence complementary to the desired cleavage site of mRNA. Because this type of ribozyme utilizes only RNA as the substrate, it offers a further advantage of not attacking genomic DNA. When SS169 mRNA itself has a double strand structure, the target sequence can be made single-stranded by using a hybrid ribozyme joined with an RNA motif derived from a viral nucleic acid capable of specifically binding to RNA helicase [Proc. Natl. Acad. Sci. USA, 98(10): 5572-5577 (2001)]. Furthermore, when ribozyme is used in the form of an expression vector comprising the DNA encoding the ribozyme, it is also possible to make the ribozyme a hybrid ribozyme further joined with a sequence with tRNA modified to promote the transfer of the transcription product to cytoplasm [Nucleic Acids Res., 29(13): 2780-2788 (2001)].

Double-stranded oligo-RNAs (siRNAs) complementary to a partial sequence within the coding region of SS169 mRNA or the initial transcription product thereof (comprising the intron moiety in the case of the initial transcription product) can also be included in the antisense nucleic acid of the present invention. What is called RNA interference (RNAi), the phenomenon in which introducing a short double-stranded RNA into cells results in the degradation of mRNAs complementary to the RNA, has been known to occur in nematodes, insects, plants and the like; since this phenomenon has recently been found to occur in mammalian cells as well [Nature, 411(6836): 494-498 (2001)], it is drawing attention as an alternative technique to ribozymes.

The antisense oligonucleotide and ribozyme of the present invention can be prepared by determining the target region of mRNA or the initial transcription product thereof on the basis of SS169 cDNA sequence or genomic DNA sequence information, and synthesizing a sequence complementary thereto using a commercially available automated DNA/RNA synthesizer (Applied Biosystems Company, Beckman Company and the like). siRNA having RNAi activity can be prepared by synthesizing a sense strand and an antisense strand, respectively, using an automated DNA/RNA synthesizer, denaturing them in an appropriate annealing buffer, for example, at about 90° C. to about 95° C. for about 1 minute, and annealing them at about 30° C. to about 70° C. for about 1 to about 8 hours. A longer double-stranded polynucleotide can be prepared by synthesizing complementary oligonucleotide strands to overlap alternately, annealing them, and ligating them using ligase.

The gene expression inhibitory activity of the antisense nucleic acid of the present invention can be examined using a transformant comprising the nucleic acid encoding SS169, an in vivo or in vitro SS169 gene expression system, or an in vivo or in vitro SS169 protein translation system. The nucleic acid can be applied to cells by various methods known per se.

The present invention also provides an antibody against SS169 or a partial peptide thereof or a salt thereof. The antibody may be a monoclonal antibody or a polyclonal antibody, as long as it has specific affinity for an SS169 species. An antibody against an SS169 species can be produced using the SS169 species as the antigen according to a method of antibody or antiserum production known per se.

[Preparation of Monoclonal Antibody]

(a) Preparation of Cells Producing a Monoclonal Antibody

An SS169 species is administered as is, or along with a carrier or a diluent, to a mammal at a site enabling antibody production by its administration. In order to increase antibody productivity upon the administration, Freund's complete adjuvant or Freund's incomplete adjuvant may be administered. Dosing is normally performed about two to 10 times in total every 2 to 6 weeks. As examples of the mammal used, monkeys, rabbits, dogs, guinea pigs, mice, rats, sheep, and goat can be mentioned, with preference given to mice and rats.

In preparing cells producing a monoclonal antibody, an individual showing an antibody titer is selected from among mammals, e.g., mice, immunized with an antigen, the spleen or lymph node is collected 2 to 5 days after final immunization, and antibody-producing cells contained therein are fused with myeloma cells, whereby a monoclonal antibody-producing hybridoma can be prepared. A measurement of antibody titer in an antiserum can be performed by, for example, reacting an SS169 species labeled as described below with the antiserum, then determining the activity of labeling agent bound to the antibody. The fusion can be performed according to a known method, for example, the method of Koehler and Milstein [Nature, Vol. 256, p. 495 (1975)]. As examples of the fusogen, polyethylene glycol (PEG), Sendai virus and the like can be mentioned, with preference given to PEG.

As examples of the myeloma cells, NS-1, P3U1, SP2/0 and the like can be mentioned, with preference given to P3U1. The ratio by number of antibody-producing cells (splenocytes) and myeloma cells is preferably about 1:1 to 20:1; cell fusion can be efficiently performed by adding PEG (preferably PEG1000 to PEG6000) at a concentration of about 10% to 80%, and incubating the cells at about 20° C. to 40° C., preferably about 30° C. to 37° C., for about 1 to 10 minutes.

Various methods can be used for screening a monoclonal antibody-producing hybridoma; for example, a method that comprises adding a hybridoma culture supernatant to a solid phase (e.g., microplate) having an antigen such as a protein, directly or along with a carrier, adsorbed thereto, then adding an anti-immunoglobulin antibody (an anti-mouse immunoglobulin antibody is used when mouse cells are used for the cell fusion) labeled with a radioactive substance, an enzyme or the like, or Protein A, and detecting the monoclonal antibody bound to the solid phase; a method that comprises adding a hybridoma culture supernatant to a solid phase having an anti-immunoglobulin antibody or Protein A adsorbed thereto, adding a protein or the like labeled with a radioactive substance, an enzyme or the like, and detecting the monoclonal antibody bound to the solid phase; and the like can be mentioned.

Monoclonal antibodies can be selected according to a method known per se or a method based thereon; this selection can normally be achieved using a medium for animal cells supplemented with HAT (hypoxanthine, aminopterin, thymidine) and the like. Any selection and breeding medium can be used, as long as it allows the hybridoma to grow. For example, an RPMI 1640 medium containing 1% to 20%, preferably 10% to 20%, fetal calf serum, a GIT medium (Wako Pure Chemical Industries, Ltd.) containing 1% to 10% fetal calf serum, a serum free medium for hybridoma culture (SFM-101, Nissui Seiyaku Co., Ltd.) and the like can be used. Cultivation temperature is normally 20° C. to 40° C., preferably about 37° C. Cultivation time is normally 5 days to 3 weeks, preferably 1 week to 2 weeks. The cultivation may be performed normally in the presence of 5% gaseous carbon dioxide. The antibody titer of hybridoma culture supernatant can be determined in the same manner as the above-described determination of antibody titer in antiserum.

(b) Purification of Monoclonal Antibody

Separation and purification of the monoclonal antibody can be performed according to a method of immunoglobulin separation and purification, as in ordinary separation and purification of polyclonal antibody [e.g., salting-out, alcohol precipitation, isoelectric point precipitation, electrophoresis, adsorption and desorption with ion exchangers (e.g., DEAE), ultracentrifugation, gel filtration, specific purification comprising collecting only the antibody using an activated adsorbent such as an antigen-bound solid phase, Protein A, or Protein G, and dissociating the linkage to separate the desired antibody].

[Preparation of Polyclonal Antibody]

The polyclonal antibody of the present invention can be produced according to a method known per se or a method based thereon. For example, the polyclonal antibody of the present invention can be produced by forming a complex of an immunoantigen (an antigen such as a protein) and a carrier protein, immunizing a mammal with the complex in the same manner as the above-described method of monoclonal antibody production, collecting a product containing an antibody against an SS169 species from the immunized animal, and separating and purifying the antibody.

Regarding the complex of immunoantigen and carrier protein used to immunize a mammal, the kind of carrier protein and the mixing ratio of carrier and hapten may be any ones whatever they are, as long as an antibody against the immunizing hapten crosslinked to the carrier is efficiently produced; for example, a method that comprises coupling bovine serum albumin, bovine thyroglobulin, keyhole limpet hemocyanin or the like to the hapten in a ratio by weight of about 0.1 to 20, preferably about 1 to 5, to 1 of hapten, can be used.

Various condensing agents can be used for the coupling of hapten and carrier; glutaraldehyde, carbodiimide, maleimide activated ester, activated ester reagents comprising the thiol group or the dithiopyridyl group, and the like can be used.

The condensation product is administered as is, or along with a carrier or a diluent, to a mammal at a site enabling antibody production by its administration. In order to increase antibody productivity upon the administration, Freund's complete adjuvant or Freund's incomplete adjuvant may be administered. Dosing is normally performed about three to 10 times in total every 2 to 6 weeks.

The polyclonal antibody can be collected from blood, ascites fluid and the like, preferably blood, of a mammal immunized by the above-described method.

Polyclonal antibody titer in antiserum can be determined in the same manner as the above-described determination of antibody titer in serum. Separation and purification of the polyclonal antibody can be performed according to a method of immunoglobulin separation and purification, as in the above-described separation and purification of monoclonal antibody.

SS169 or a partial peptide thereof or a salt thereof, the nucleic acid encoding SS169 or a partial peptide thereof (including antisense nucleic acids), and an antibody against SS169 or a partial peptide thereof can be used for (1) identification of a compound having specific affinity for SS169 (ligand or receptor) or a salt thereof, (2) a prophylactic/therapeutic agent for a disease associated with SS169 dysfunction, (3) a prophylactic/therapeutic agent for a disease associated with SS169 overexpression, (4) a genetic diagnostic agent, (5) a method of screening a compound that changes the expression amount of SS169, (6) a prophylactic/therapeutic agent for various diseases comprising a compound that changes the expression amount of SS169, (7) a method of quantifying a compound having specific affinity for SS169, (8) a method of screening a compound that changes the bindability between SS169 and a compound having specific affinity for SS169 (agonist, antagonist and the like), (9) a prophylactic/therapeutic agent for various diseases comprising a compound that changes the bindability between SS169 and a compound having specific affinity for SS169 (agonist, antagonist), (10) quantitation of SS169 or a partial peptide thereof or a salt thereof, (11) a method of screening a compound that changes the amount of SS169 in the cell membrane or extracellular fluid, (12) a prophylactic/therapeutic agent for various diseases comprising a compound that changes the amount of SS169 in the cell membrane or extracellular fluid, (13) preparation of a non-human transgenic animal bearing the SS169-encoding DNA, (14) preparation of a non-human knockout animal having the SS169-encoding gene inactivated therein, and the like.

In particular, by using an affinity assay system using an expression system for the recombinant SS169 of the present invention or a partial peptide thereof, it is possible to screen a compound that changes the bindability between SS169 and a receptor thereof (or ligand) (e.g., agonist, antagonist and the like), and to use the agonist or antagonist as a prophylactic/therapeutic agent for various diseases and the like.

Uses of SS169 species, DNAs encoding SS169 or a partial peptide thereof (hereinafter sometimes abbreviated as "the DNA of the present invention"), the antisense nucleic acid of the present invention, and an antibody against SS169 species (hereinafter sometimes abbreviated as "the antibody of the present invention") are hereinafter described specifically.

(1) Identification of Compound Having Specific Affinity for SS169

SS169 or a partial peptide thereof or a salt thereof is useful as a reagent for searching or identifying a compound having specific affinity for SS169 or a salt thereof (receptor or ligand).

Accordingly, the present invention provides a method of identifying a compound having specific affinity for SS169 or a salt thereof, which comprises bringing an SS169 species into contact with a test compound.

As the test compound, known ligands (for example, angiotensin, bombesin, canavinoid, cholecystokinin, glutamine, serotonin, melatonin, neuropeptide Y, opioid, purines, vasopressin, oxytocin, PACAP, secretin, glucagon, calcitonin, adrenomedulin, somatostatin, GHRH, CRF, ACTH, GRP, PTH, VIP (vasoactive intestinal and related polypeptide), somatostatin, dopamine, motilin, amylin, bradykinin, CGRP (calcitonin gene-related peptide), leukotrienes, pancreastatin, prostaglandins, thromboxane, adenosine, adrenaline, α- and β-chemokines (for example, IL-8, GROα, GROβ, GROγ, NAP-2, ENA-78, PF4, IP10, GCP-2, MCP-1, HC14, MCP-3, I-309, MIP1α, MIP-1β, RANTES and the like), endothelin, enterogastrin, histamine, neurotensin, TRH, pancreatic polypeptide, galanin and the like, known receptors for the above-described ligands, orphan receptors identified as a result of genome analysis, as well as other substances, for example, tissue extracts, intact cells, cell membrane fractions, cell culture supernatants and the like of mammals (for example, humans, mice, rats, swine, cattle, sheep, monkeys and the like), can be used. For example, a tissue extract, a cell culture supernatant or the like is added to cells expressing an SS169 species, fractionation is performed with a cell stimulation activity or the like as an index, and a single ligand can be obtained finally. Alternatively, an SS169 species is added to intact cells, a cell membrane fraction or the like, fractionation is performed with a cell stimulation activity, binding activity or the like as an index, and a single receptor can be obtained finally.

Specifically, the method of identifying a compound having specific affinity for SS169 or a salt thereof is a method of identifying a compound that binds to SS169 to exhibit a cell stimulation activity (for example, activities that promote or suppress arachidonic acid release, acetylcholine release, intracellular $Ca^{2+}$ release, intracellular cAMP production, intracellular cGMP production, inositolphosphate production, cell membrane potential changes, intracellular protein phosphorylation, c-fos activation, pH reduction and the like) (for example, peptides, proteins, non-peptide compounds, synthetic compounds, fermentation products and the like) or a salt thereof by using an SS169 species, or by constructing an expression system for recombinant SS169 or a partial peptide thereof, and using an affinity assay system using the expression system.

The method of identifying a compound having specific affinity for SS169 or a salt thereof comprises measuring the amount of test compound bound to an SS169 species, a cell stimulation activity or the like when the SS169 species and the test compound are brought into contact with each other.

More specifically, the present invention provides:
(1) a method of identifying a compound having specific affinity for SS169 or a salt thereof, which comprises measuring the amount of labeled test compound bound to an SS169 species when the labeled test compound is brought into contact with the SS169 species,
(2) a method of identifying a compound having specific affinity for SS169 or a salt thereof, which comprises measuring the amount of labeled test compound to SS169-producing cells or a cell membrane fraction thereof, an extracellular fluid, or a cell culture supernatant when the labeled test compound is brought into contact with the cells, the membrane fraction, the extracellular fluid or the cell culture supernatant (in this case, for example, SS169 is immobilized using the above-described solid phase (cell culture plate and the like) having the antibody of the present invention immobilized thereon)),
(3) a method of identifying a compound having specific affinity for SS169 or a salt thereof, which comprises measuring the amount of labeled test compound bound to an SS169 species when the labeled test compound is brought into contact with an SS169 species expressed on the cell membrane, or secreted in the culture supernatant, by culturing a transformant comprising the DNA encoding SS169 or a partial peptide thereof (in this case, for example, the SS169 species is immobilized using the above-described solid phase (cell culture plate and the like) having the antibody of the present invention immobilized thereon),
(4) a method of identifying a ligand (or receptor) for SS169 or a salt thereof, which comprises measuring a cell stimulation activity (for example, activities that promote or suppress arachidonic acid release, acetylcholine release, intracellular $Ca^{2+}$ release, intracellular cAMP production, intracellular cGMP production, inositolphosphate production, cell membrane potential changes, intracellular protein phosphorylation, c-fos activation, pH reduction and the like, and the like) mediated by SS169 (or test compound membrane protein or the like) when a test compound (or cells containing test compound membrane protein or the like on the cell membrane) is brought into contact with SS169-producing cells (or culture supernatant of SS169-secreting cells), and
(5) a method of identifying a ligand (or receptor) for SS169 or a salt thereof, which comprises measuring a cell stimulation activity (for example, activities that promote or suppress arachidonic acid release, acetylcholine release, intracellular $Ca^{2+}$ release, intracellular CAMP production, intracellular cGMP production, inositolphosphate production, cell membrane potential changes, intracellular protein phosphorylation, c-fos activation, pH reduction and the like, and the like) mediated by an SS169 species (or test compound membrane protein or the like) when a test compound (or cells containing test compound membrane protein or the like on the cell membrane) is brought into contact with an SS169 species expressed on the cell membrane by culturing a transformant comprising the DNA encoding SS169 or a partial peptide thereof (an SS169 species secreted in the culture supernatant by culturing a transformant comprising the DNA encoding SS169 or a partial peptide thereof).

In particular, it is preferable that the tests of (4) to (5) above be performed after the tests of (1) to (3) above are performed and the test compound is confirmed to bind to SS169.

First, as the SS169 species used in the method of identifying a ligand (or receptor), any of the above-described SS169, a partial peptide thereof, and a salt thereof may be used, but recombinant SS169 expressed in large amounts using animal cells and the like are suitable.

Recombinant SS169 is produced by the expression method described above, which is preferably performed by expressing the SS169-encoding DNA in mammalian cells or insect cells. A cDNA is normally used as the DNA fragment encoding the desired portion of the protein, but is not construed as limiting. For example, a gene fragment or a synthetic DNA may also be used. For introducing an SS169-encoding DNA fragment into host animal (or insect) cells and efficiently expressing the same, it is preferable to insert the DNA fragment downstream of an SV40-derived promoter, a retrovirus promoter, a metallothionein promoter, a human heat shock promoter, a cytomegalovirus promoter, an SRα promoter, the polyhedrin promoter of nuclear polyhedrosis virus (NPV), which is a baculovirus having insect hosts, or the like.

In the method of the present invention of identifying a ligand (or receptor), the SS169 species may be an SS169 species purified according to a method known per se, or may be used as cells producing the SS169 species or a membrane fraction thereof, or as a culture supernatant of cells secreting the SS169 species.

When cells producing an SS169 species are used in the method of the present invention of identifying a ligand, the cells may be fixed with glutaraldehyde, formalin and the like. This fixation can be performed according to a method known per se.

Cells producing an SS169 species refer to host cells expressing the SS169 species; as the host cells, *Escherichia coli, Bacillus subtilis*, yeasts, insect cells, animal cells and the like can be used.

The aforementioned cell membrane fraction refers to a fraction rich in cell membrane obtained by a method known per se after cell disruption. As the method of cell disruption, cell squashing using a Potter-Elvehjem homogenizer, disruption using a Waring blender or Polytron (manufactured by Kinematica Inc.), disruption by ultrasonication, disruption by cell spraying through a thin nozzle under an increased pressure using a French press or the like, and the like can be mentioned. For cell membrane fractionation, fractionation by centrifugal forces, such as fractional centrifugation or density gradient centrifugation, is mainly used. For example, a cell disruption fluid is centrifuged at a low speed (500 rpm to 3000 rpm) for a short time (normally about 1 to 10 minutes), the supernatant is centrifuged at a higher speed (15000 rpm to 30000 rpm) normally for 30 minutes to 2 hours, and the precipitate obtained is used as the membrane fraction. The membrane fraction is rich in the SS169 species expressed and cell-derived membrane components such as phospholipids and membrane proteins.

The amount of SS169 species in the cells producing the SS169 species and the membrane fraction thereof is preferably $10^3$ to $10^8$ molecules per cell, more preferably $10^5$ to $10^7$ molecules. Note that as the expression amount increases, ligand-binding activity per unit of membrane fraction (specific activity) increases so that it is possible to construct a highly sensitive screening system, and to assay a large number of samples in the same lot.

For performing methods (1) to (3) above for identifying a ligand for SS169 or a salt thereof, an appropriate SS169 species-containing membrane fraction and labeled test compound are necessary.

As the SS169 species-containing membrane fraction, a naturally occurring SS169-containing membrane fraction, or a recombinant SS169 species-containing membrane fraction having the same quality of activity thereas, and the like are desirable. As used herein, the same quality of activity means equivalent ligand-binding activity, signal transmission activity or the like.

As the labeled test compound, angiotensin, bombesin, canavinoid, cholecystokinin, glutamine, serotonin, melatonin, neuropeptide Y, opioid, purines, vasopressin, oxytocin, PACAP, secretin, glucagon, calcitonin, adrenomedulin, somatostatin, GHRH, CRF, ACTH, GRP, PTH, VIP (vasoactive intestinal and related polypeptide), somatostatin, dopamine, motilin, amylin, bradykinin, CGRP (calcitonin gene-related peptide), leukotrienes, pancreastatin, prostaglandins, thromboxane, adenosine, adrenaline, α- and β-chemokines (for example, IL-8, GROα, GROβ, GROγ, NAP-2, ENA-78, PF4, IP10, GCP-2, MCP-1, HC14, MCP-3, I-309, MIP1α, MIP-10β, RANTES and the like), endothelin, enterogastrin, histamine, neurotensin, TRH, pancreatic polypeptide, galanin and the like, labeled with [$^3$H], [$^{125}$I], [$^{14}$C], [$^{35}$S] or the like, are suitable.

Specifically, to perform a method of identifying a ligand for SS169 or a salt thereof, a standard preparation of SS169 species is first prepared by suspending SS169-producing cells or a membrane fraction thereof in a buffer suitable for the method of identification. The buffer may be any buffer that does not interfere with the binding of SS169 and its ligand, such as a phosphate buffer or Tris-hydrochloride buffer having a pH value of 4 to 10 (desirably a pH value of 6 to 8). To reduce non-specific binding, a surfactant such as CHAPS, Tween-80™ (Kao-Atlas Co.), digitonin or deoxycholate, and various proteins such as bovine serum albumin and gelatin may be added to the buffer. Furthermore, to suppress the degradation of receptors and ligands by proteases, a protease inhibitor such as PMSF, leupeptin, E-64 (manufactured by Peptide Research Laboratory, Co.), or pepstatin may be added. A test compound labeled with a given amount (5,000 cpm to 500,000 cpm) of [$^3$H], [$^{125}$I], [$^{14}$C], [$^{35}$S] or the like is added to 0.01 ml to 10 ml of a suspension of SS169 species. To determine non-specific binding (NSB), a reaction tube containing the unlabeled test compound in large excess is also provided. The reaction is performed at about 0° C. to 50° C., desirably about 4° C. to 37° C., for about 20 minutes to 24 hours, desirably about 30 minutes to 3 hours. After the reaction, the reaction mixture is filtered through glass fiber filter paper and the like, and washed with an appropriate amount of the same buffer; thereafter, the residual radioactivity on the glass fiber filter paper is counted using a liquid scintillation counter or a γ-counter. A test compound showing a count (B-NSB) exceeding 0 cpm, calculated by subtracting non-specific binding (NSB) from total binding (B), can be selected as a ligand (agonist) for SS169 or a salt thereof.

To perform methods (4) and (5) above of identifying a ligand for SS169 or a salt thereof, a cell stimulation activity (for example, activities that promote or suppress arachidonic acid release, acetylcholine release, intracellular $Ca^{2+}$ release, intracellular cAMP production, intracellular cGMP production, inositolphosphate production, cell membrane potential changes, intracellular protein phosphorylation, c-fos activation, pH reduction and the like, and the like) mediated by SS169 can be measured using a known method or a commercially available assay kit. Specifically, first, cells producing an SS169 species are cultured on a multi-well plate or the like. In ligand identification, the medium is replaced with a fresh medium or an appropriate non-cytotoxic buffer in advance, and a test compound and the like are added, followed by incubation for a given time; thereafter, the cells are extracted or the supernatant is recovered, and the resulting product is quantified by each method. If it is difficult to detect the production of an indicator substance for cell stimulation activity (for example, arachidonic acid and the like) due to a degrading enzyme contained in the cells, the assay may be performed with the addition of an inhibitor of the degrading enzyme. Activities such as cAMP production suppression can be detected as suppressive effects on the production of cells having baseline production previously increased with forskolin or the like.

Although a method of identifying a compound having specific affinity for SS169 has been described specifically with reference to a case wherein SS169 is a membrane protein, those skilled in the art can easily identify a compound having specific affinity for SS169 by applying the above-described technique even when SS169 is a secretory protein.

The kit for identifying a compound having specific affinity for SS169 or a salt thereof comprises an SS169 species, SS169-producing cells or a membrane fraction thereof, a culture supernatant of SS169-secreting cells, and the like.

As examples of the kit of the present invention for identifying a ligand (receptor), the following can be mentioned.

1. Reagents for Ligand (Receptor) Identification (1) Assay Buffer Solution and Wash Buffer Solution Hanks' balanced salt solution (manufactured by Gibco Co.) supplemented with 0.05% bovine serum albumin (manufactured by Sigma Co.).

The solution is sterilized by filtration through a filter of 0.45-µm pore size and stored at 4° C., or may be prepared freshly just before use.

(2) Standard Preparation of SS169 Species

CHO cells expressing an SS169 species are subcultured on a 12-well plate at a density of $5 \times 10^5$ cells/well and cultured at 37° C. under 5% $CO_2$ and 95% air for 2 days (when SS169 is a secretory protein, the plate is coated with anti-SS169 antibody).

(3) Labeled Test Compound

A commercially available compound labeled with [$^3$H], [$^{125}$I], [$^{14}$C], [$^{35}$S] or the like, or a compound labeled by an appropriate method.

An aqueous solution of the compound is stored at 4° C. or −20° C. and diluted to 1 µM with the assay buffer solution just before use. A test compound slightly soluble in water is dissolved in dimethylformamide, DMSO, methanol or the like.

(4) Non-Labeled Test Compound

The same compound as the labeled compound is prepared at a 100 to 1,000 fold higher concentration.

2. Assay Method
(1) CHO cells expressing an SS169, cultured on a 12-well tissue culture plate, are washed twice with 1 ml of the assay buffer solution (when SS169 is secreted, the cells and culture supernatant are removed, then the plate is washed with the assay buffer solution in the same manner); thereafter 490 µl of the assay buffer solution is added to each well.
(2) 5 µl of the labeled test compound is added and the reaction is performed at room temperature for 1 hour. To determine non-specific binding, 5 µl of the non-labeled test compound is added in advance.
(3) The reaction liquid is removed and the wells are washed 3 times with 1 ml of the wash buffer solution. The labeled test compound bound to the cells (plate) is dissolved in 0.2N NaOH-1% SDS, and mixed with 4 ml of liquid scintillator A (manufactured by Wako Pure Chemical Industries, Ltd.).
(4) Radioactivity is measured using a liquid scintillation counter (manufactured by Beckman Co.).

As examples of the ligand capable of binding to SS169 or a salt thereof, substances specifically present in the brain, hypophysis, pancreas and the like, and the like can be mentioned; specifically, known ligands such as angiotensin, bombesin, canavinoid, cholecystokinin, glutamine, serotonin, melatonin, neuropeptide Y, opioid, purines, vasopressin, oxytocin, PACAP, secretin, glucagon, calcitonin, adrenomedulin, somatostatin, GHRH, CRF, ACTH, GRP, PTH, VIP (vasoactive intestinal and related polypeptide), somatostatin, dopamine, motilin, amylin, bradykinin, CGRP (calcitonin gene-related peptide), leukotrienes, pancreastatin, prostaglandins, thromboxane, adenosine, adrenaline, α- and β-chemokines (for example, IL-8, GROα, GROβ, GROγ, NAP-2, ENA-78, PF4, IP10, GCP-2, MCP-1, HC14, MCP-3, I-309, MIP1α, MIP-1β, RANTES and the like), endothelin, enterogastrin, histamine, neurotensin, TRH, pancreatic polypeptide, galanin and the like, known receptors for the above-described ligands, various orphan receptors and the like can be used.

(2) Prophylactic/Therapeutic Agents for Diseases Associated with SS169 Dysfunction In method (1) above, provided that a compound having specific affinity for SS169 is revealed, (1) an SS169 species or (2) the DNA encoding SS169 or a partial peptide thereof can be used as a pharmaceutical such as a prophylactic/therapeutic agent for a disease associated with SS169 dysfunction, depending on the action of the compound.

For example, for a patient in a condition where the physiological action of ligand (or receptor) is unexpected due to a reduction is SS169 in his or her body (SS169 deficiency), it is possible to increase the amount of SS169 in the patient's body, and to allow the ligand (or receptor) to act in full, by (1) administering an SS169 species to the patient to replenish SS169, or (2) (i) administering the DNA encoding SS169 or a partial peptide thereof to the patient to allow the expression thereof, or (ii) introducing the DNA encoding SS169 or a partial peptide thereof into the subject cells to allow the expression thereof, and then transplanting the cells to the patient, or the like. Accordingly, an SS169 species or the DNA encoding the same is useful as a safe and less toxic prophylactic/therapeutic agent for a disease associated with SS169 dysfunction.

SS169 is expressed nearly specifically in skeletal muscles and highly expressed in diabetic model mice and during refeeding after fasting, and its expression is influenced by insulin and influences insulin action; for these and other reasons, as the disease associated with SS169 dysfunction, diseases involved in (i) skeletal muscle cell differentiation and/or (ii) metabolic abnormality (hypofunction or hyperfunction) [examples include, but are not limited to, metabolic abnormalities (particularly sugar/lipid metabolic abnormalities) in the liver, adipose tissue, skeletal muscles, pancreas and the like, and the like; the same applies below] (for example, obesity, diabetes mellitus, impaired glucose tolerance, arteriosclerosis, hypertension, hyperlipemia and the like) and the like can be mentioned.

(1) An SS169 species and (2) the DNA encoding SS169 or a partial peptide thereof (in the present specification, also referred to as "the DNA of the present inventions") can be used as prophylactic/therapeutic agents for diseases associated with SS169 dysfunction after being mixed with a pharmacologically acceptable carrier to prepare pharmaceutical compositions as necessary.

As the pharmacologically acceptable carrier, various organic or inorganic carrier substances in common use as pharmaceutical materials can be used, which are formulated as excipients, lubricants, binders, and disintegrants in solid preparations; as solvents, solubilizers, suspending agents, isotonizing agents, buffers, soothing agents and the like in liquid preparations. Pharmaceutical additives such as antiseptics, antioxidants, colorants, and sweeteners can also be used as necessary.

As examples of preferable excipients, lactose, sucrose, D-mannitol, D-sorbitol, starch, α-starch, dextrin, crystalline cellulose, low-substituted hydroxypropylcellulose, carboxymethylcellulose sodium, gum arabic, pullulan, light silicic anhydride, synthetic aluminum silicate, magnesium metasilicate aluminate and the like can be mentioned.

As examples of preferable lubricants, magnesium stearate, calcium stearate, talc, colloidal silica and the like can be mentioned.

As examples of preferable binders, α-starch, cane sugar, gelatin, gum arabic, methylcellulose, carboxymethylcellulose, carboxymethylcellulose sodium, crystalline cellulose, sucrose, D-mannitol, trehalose, dextrin, pullulan, hydroxypropylcellulose, hydroxypropylmethylcellulose, polyvinylpyrrolidone and the like can be mentioned.

As examples of preferable disintegrants, lactose, sucrose, starch, carboxymethylcellulose, carboxymethylcellulose calcium, crosslinked carmellose sodium, carboxymethylstarch sodium, light silicic anhydride, low-substituted hydroxypropylcellulose and the like can be mentioned.

As examples of preferable solvents, water for injection, physiological saline, Ringer's solution, alcohol, propylene glycol, polyethylene glycol, sesame oil, corn oil, olive oil, cottonseed oil and the like can be mentioned.

As examples of preferable solubilizers, polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like can be mentioned.

As examples of preferable suspending agents, surfactants such as stearyltriethanolamine, sodium lauryl sulfate, laurylaminopropionic acid, lecithin, benzalkonium chloride, benzethonium chloride, and glyceryl monostearate; hydrophilic polymers such as polyvinyl alcohol, polyvinylpyrrolidone, carboxymethylcellulose sodium, methylcellulose, hydroxymethylcellulose, hydroxyethylcellulose, and hydroxypropylcellulose; polysorbates, polyoxyethylene hydrogenated castor oil and the like can be mentioned.

As examples of preferable isotonizing agents, sodium chloride, glycerin, D-mannitol, D-sorbitol, glucose and the like can be mentioned.

As examples of preferable buffers, buffer solutions such as of phosphates, acetates, carbonates and citrates, and the like can be mentioned.

As examples of preferable soothing agents, benzyl alcohol and the like can be mentioned.

As examples of preferable antiseptic agents, para-oxybenzoic acid esters, chlorobutanol, benzyl alcohol, phenethyl alcohol, dehydroacetic acid, sorbic acid and the like can be mentioned.

As examples of preferable antioxidants, sulfites, ascorbic acid salts and the like can be mentioned.

As examples of preferable colorants, water-soluble food tar colors (e.g., food colors such as Food Color Red No.2 and No. 3, Food Color Yellow No. 4 and No. 5, and Food Color Blue No. 1 and No. 2), water-insoluble lake colors (e.g., aluminum salts of the aforementioned water-soluble food tar colors, and the like), natural colors (e.g., β-carotene, chlorophyll, red iron oxide and the like) and the like can be mentioned.

As examples of preferable sweeteners, saccharin sodium, dipotassium glycyrrhizinate, aspartame, stevia and the like can be mentioned.

As examples of dosage forms for the aforementioned pharmaceutical composition, oral preparations such as tablets, capsules (including soft capsules and microcapsules), granules, powders, syrups, emulsions, and suspensions; and non-oral preparations such as injections (e.g., subcutaneous injections, intravenous injections, intramuscular injections, intraperitoneal injections and the like), external preparations (e.g., nasal preparations, transdermal preparations, ointments and the like), suppositories (e.g., rectal suppositories, vaginal suppositories and the like), pellets, drip infusions, and sustained-release preparations (e.g., sustained-release microcapsules and the like) can be mentioned.

These pharmaceutical compositions can be produced by a method in common use in the field of drug formulation technology, for example, methods described in the Japanese Pharmacopoeia and the like. Specific methods of preparing preparations are described in detail below. The active ingredient content in the pharmaceutical composition varies depending on dosage form, active ingredient dose and the like, and is, for example, about 0.1% to 100% by weight.

For example, an oral preparation is produced by adding an excipient (e.g., lactose, sucrose, starch, D-mannitol and the like), a disintegrant (e.g., carboxymethylcellulose calcium and the like), a binder (e.g., α-starch, gum arabic, carboxymethylcellulose, hydroxypropylcellulose, polyvinylpyrrolidone and the like), a lubricant (e.g., talc, magnesium stearate, polyethylene glycol 6000 and the like) and the like, to active ingredients, and compressing them, with coating performed, if necessary, using a coating base for the purpose of taste masking, enteric dissolution or sustained release, by a method known per se.

As examples of the coating base, sugar-coating bases, water-soluble film-coating bases, enteric film-coating bases, sustained-release film-coating bases and the like can be mentioned.

As the sugar-coating base, sucrose is used, which may be used in combination with one or two or more kinds selected from among talc, precipitated calcium carbonate, gelatin, gum arabic, pullulan, carnauba wax and the like.

As examples of the water-soluble film-coating base, cellulose polymers such as hydroxypropylcellulose, hydroxypropylmethylcellulose, hydroxyethylcellulose and methylhydroxyethylcellulose; synthetic polymers such as polyvinylacetal diethylaminoacetate, aminoalkylmethacrylate copolymer E [Eudragit E (trade name), Roehm Pharma GmbH], and polyvinylpyrrolidone; polysaccharides such as pullulan; and the like can be mentioned.

As examples of the enteric film-coating base, cellulose polymers such as hydroxypropylmethylcellulose phthalate, hydroxypropylmethylcellulose acetate succinate, carboxymethylethylcellulose, and cellulose acetate phthalate; acrylate polymers such as methacrylate copolymer L [Eudragit L (trade name), Roehm Pharma GmbH], methacrylate copolymer LD [Eudragit L-30D55 (trade name), Roehm Pharma GmbH], and methacrylate copolymer S [Eudragit S (trade name), Roehm Pharma GmbH]; naturally occurring substances such as shellac; and the like can be mentioned.

As examples of the sustained-release film-coating base, cellulose polymers such as ethylcellulose; acrylate polymers such as aminoalkylmethacrylate copolymer RS [Eudragit RS (trade name), Roehm Pharma GmbH] and ethyl acrylate/methyl methacrylate copolymer suspension [Eudragit NE (trade name), Roehm Pharma GmbH]; and the like can be mentioned.

The above-described coating bases may be used in a suitable mixture of two or more kinds thereof. Also, a light-blocking agent such as titanium oxide or iron sesquioxide may be used during coating.

An injection is produced by dissolving, suspending or emulsifying active ingredients, along with a dispersing agent (e.g., polysorbate 80, polyoxyethylene hydrogenated castor oil 60, polyethylene glycol, carboxymethylcellulose, sodium alginate and the like), a preservative (e.g., methylparaben, propylparaben, benzyl alcohol, chlorobutanol, phenol and the like), an isotonizing agent (e.g., sodium chloride, glycerin, D-mannitol, D-sorbitol, glucose and the like) and the like, in an aqueous solvent (e.g., distilled water, physiological saline, Ringer's solution and the like) or an oily solvent (e.g., vegetable oils such as olive oil, sesame oil, cottonseed oil and corn oil, propylene glycol and the like). If desired, additives such as a solubilizer (e.g., sodium salicylate, sodium acetate and the like), a stabilizer (e.g., human serum albumin and the like), and a soothing agent (e.g., benzyl alcohol and the like) may be used. The injection is usually filled in suitable ampoules.

Because the preparation thus obtained is safe and less toxic, it can be administered to, for example, mammals (for example, humans, rats, rabbits, sheep, swine, cattle, cats, dogs, monkeys and the like).

When the DNA of the present invention is used as the above-described prophylactic/therapeutic agent, the DNA of the present invention can be administered alone, or after being inserted into an appropriate expression vector such as a retrovirus vector, adenovirus vector, or adenovirus-associated virus vector, according to a conventional method. The DNA of the present invention can also be administered as is, or along with an auxiliary for promoting its ingestion, using a gene gun or a catheter such as a hydrogel catheter.

The dose of SS169 species varies depending on the subject of administration, target organ, symptoms, method of administration and the like; in oral administration, the dose is normally about 0.1 to 100 mg, preferably about 1.0 to 50 mg, and more preferably about 1.0 to 20 mg, per day, in, for example, a patient with a sugar/lipid metabolic abnormality (assuming a 60 kg body weight). In parenteral administration, the single dose varies depending on the subject of administration, target organ, symptoms, method of administration and the like; for example, in the form of an injection, the dose is normally about 0.01 to 30 mg, preferably about 0.1 to 20 mg, and more preferably about 0.1 to 10 mg, per day, in, for example, a patient with a sugar/lipid metabolic abnormality (assuming a 60 kg body weight). In cases where the subject of administration is other than a human, a dose corresponding to a human dose per 60 kg body weight can be administered.

The dose of the DNA of the present invention varies depending on the subject of administration, target organ, symptoms, method of administration and the like; in oral administration, the dose is normally about 0.1 to 100 mg, preferably about 1.0 to 50 mg, and more preferably about 1.0 to 20 mg, per day, in, for example, a patient with a sugar/lipid metabolic abnormality (assuming a 60 kg body weight). In parenteral administration, the single dose varies depending on the subject of administration, target organ, symptoms, method of administration and the like; for example, in the form of an injection, the dose is normally about 0.01 to 30 mg, preferably about 0.1 to 20 mg, and more preferably about 0.1 to 10 mg, per day, in, for example, a patient with a sugar/lipid metabolic abnormality (assuming a 60 kg body weight). In cases where the subject of administration is other than a human, a dose corresponding to a human dose per 60 kg body weight can be administered.

(3) Prophylactic/Therapeutic Agents for Diseases Associated with SS169 Overexpression An antibody against SS169 species is capable of inactivating (i.e., neutralizing) a signal transmission function involved by SS169, for example, a cell stimulation activity mediated by SS169 (for example, activities that promote or suppress arachidonic acid release, acetylcholine release, intracellular $Ca^{2+}$ release, intracellular cAMP production, intracellular cGMP production, inositolphosphate production, cell membrane potential changes, intracellular protein phosphorylation, c-fos activation, pH reduction and the like, and the like). On the other hand, an antisense nucleic acid (including ribozymes and double-stranded oligo-RNAs having and RNAi activity) of SS169 or a partial peptide thereof is capable of inhibiting the expression of SS169 by blocking the transcription of the SS169 gene, processing of the transcription product and/or the translation from mRNA. Accordingly, (1) the antibody of the present invention or (2) the antisense nucleic acid of the present invention can be used as a pharmaceutical such as a prophylactic/therapeutic agent for a disease associated with SS169 overexpression.

SS169 is expressed nearly specifically in skeletal muscles and highly expressed in diabetic model mice and during re-feeding after fasting, and its expression is influenced by insulin and influences insulin action; for these and other reasons, SS169 is useful in the prophylaxis/treatment of diseases involved in differentiation of skeletal muscle cell and/or metabolic abnormality (hypofunction or hyperfunction) (for example, obesity, diabetes mellitus, impaired glucose tolerance, arteriosclerosis, hypertension, hyperlipemia and the like).

The antibody of the present invention and the antisense nucleic acid of the present invention can be formulated in the same manner as the aforementioned "prophylactic/therapeutic agent for a disease associated with SS169 dysfunction". The antisense nucleic acid can also be administered as is, using a gene gun or a catheter such as a hydrogel catheter.

The dose of the antibody of the present invention varies depending on the subject of administration, target organ, symptoms, method of administration and the like; in oral administration, the dose is normally about 0.1 to 100 mg, preferably about 1.0 to 50 mg, and more preferably about 1.0 to 20 mg, per day, in, for example, a patient with a sugar/lipid metabolic abnormality (assuming a 60 kg body weight). In parenteral administration, the single dose varies depending on the subject of administration, target organ, symptoms, method of administration and the like; for example, in the form of an injection, the dose is normally about 0.01 to 30 mg, preferably about 0.1 to 20 mg, and more preferably about 0.1 to 10 mg, per day, in, for example, a patient with a sugar/lipid metabolic abnormality (assuming a 60 kg body weight). In cases where the subject of administration is other than a human, a dose corresponding to a human dose per 60 kg body weight can be administered.

The dose of the antisense nucleic acid of the present invention varies depending on the subject of administration, target organ, symptoms, method of administration and the like; in oral administration, the dose is normally about 0.1 to 100 mg, preferably about 1.0 to 50 mg, and more preferably about 1.0 to 20 mg, per day, in, for example, a patient with a sugar/lipid metabolic abnormality (assuming a 60 kg body weight). In parenteral administration, the single dose varies depending on the subject of administration, target organ, symptoms, method of administration and the like; for example, in the form of an injection, the dose is normally about 0.01 to 30 mg, preferably about 0.1 to 20 mg, and more preferably about 0.1 to 10 mg, per day, in, for example, a patient with a sugar/lipid metabolic abnormality (assuming a 60 kg body weight). In cases where the subject of administration is other than a human, a dose corresponding to a human dose per 60 kg body weight can be administered.

(4) Genetic Diagnostic Reagents

Because a nucleic acid comprising the base sequence encoding SS169 or the initial translation product thereof or a portion thereof (hereinafter referred to as "the sense nucleic acid of the present invention") or the antisense nucleic acid of the present invention is capable of detecting an abnormality in the DNA or mRNA encoding SS169 in a mammal (for example, humans, rats, rabbits, sheep, swine, cattle, cats, dogs, monkeys and the like) (gene abnormality) when used as a probe, it is useful as, for example, a genetic diagnostic reagent for damage, mutation or decreased expression of the DNA or mRNA, increased expression or overexpression of the DNA or mRNA, and the like.

The above-described genetic diagnosis using the sense nucleic acid or antisense nucleic acid of the present invention can be performed by, for example, methods known per se, such as Northern hybridization and the PCR-SSCP method (Genomics, Vol. 5, pp. 874-879 (1989), Proceedings of the National Academy of Sciences of the United States of America, Vol. 86, pp. 2766-2770 (1989)).

For example, if decreased expression of SS169 is detected by Northern hybridization, it can be judged that the subject is suffering from, for example, a disease associated with SS169 dysfunction, or is highly likely to suffer from the disease in the future. Conversely, for example, if overexpression of SS169 is detected by Northern hybridization, it can be judged that the subject is suffering from, for example, a disease associated with SS169 hyperfunction or is highly likely to suffer from the disease in the future.

SS169 is expressed nearly specifically in skeletal muscles and highly expressed in diabetic model mice and during re-feeding after fasting; for these and other reasons, SS169 is useful in the prophylaxis/treatment of diseases involved in differentiation of skeletal muscle cell and/or metabolic abnormality (hypofunction or hyperfunction) (for example, obesity, diabetes mellitus, impaired glucose tolerance, arteriosclerosis, hypertension, hyperlipemia and the like).

(5) Method of Screening a Compound that Changes the Expression Amount of SS169

The sense nucleic acid of the present invention can be used as a probe for screening a compound that changes the expression amount of SS169.

Accordingly, the present invention provides a method of screening a compound that changes the expression amount of SS169, which comprises measuring the amount of SS169 mRNA contained in, for example, (i) (1) blood, (2) a particular organ, (3) a tissue or cells isolated from an organ, of a non-human mammal, or (ii) a transformant or the like.

Specifically, the amount of SS169 mRNA is measured as described below.

(i) A drug (for example, anti-obesity drugs, anti-diabetic drugs, antihypertensive drugs, vasoactive drugs, anticancer agents and the like) or a physical stress (for example, soaking stress, electric shock, brightness/darkness, low temperatures and the like) or the like is given to a normal or disease model non-human mammal (for example, mice, rats, rabbits, sheep, swine, cattle, cats, dogs, monkeys and the like, more specifically, obese mice, diabetic mice, hypertensive rats, arteriosclerotic rabbits, cancer-bearing mice and the like); after a given time has elapsed, blood or a particular organ (for example, liver, pancreas, kidney, muscles and the like), a tissue (for example, brown or white adipose tissue and the like) or cells (skeletal muscle cells, adipocytes and the like) are obtained.

The SS169 mRNA contained in the cells and the like obtained can be quantified by, for example, extracting the mRNA from the cells and the like by an ordinary method, and using a technique such as TaqMan PCR, and can also be analyzed by performing Northern blot by a means known per se.

(ii) A transformant expressing SS169 or a partial peptide thereof can be prepared according to the method described above, and the mRNA of the SS169 or a partial peptide thereof contained in the transformant can be quantified and analyzed in the same manner as described above.

Screening of a compound that changes the expression amount of SS169 can be performed by:

(i) administering a test compound to a normal or disease model non-human mammal at a given time before (before 30 minutes to before 24 hours, preferably before 30 minutes to before 12 hours, more preferably before 1 hour to before 6 hours) or after (after 30 minutes to after 3 days, preferably after 1 hour to after 2 days, more preferably after 1 hour to after 24 hours) giving a drug, a physical stress or the like, or at the same time as the drug or physical stress, and quantifying and analyzing the amount of SS169 mRNA contained in the cells after a given time has elapsed after administration (after 30 minutes to after 3 days, preferably after 1 hour to after 2 days, more preferably after 1 hour to after 24 hours), and can also be preformed by:

(ii) mixing a test compound in the medium at the start of cultivation of the transformant according to a conventional method, and quantifying and analyzing the amount of mRNA of SS169 or a partial peptide thereof contained in the transformant after cultivation for a given time (after 1 day to after 7 days, preferably after 1 day to after 3 days, more preferably after 2 days to after 3 days).

The compound obtained using the above-described screening method or a salt thereof is a compound that acts to change the expression amount of SS169, specifically, (a) a compound that enhances a cell stimulation activity mediated by the interaction between SS169 and its receptor (or ligand) (for example, activities that promote or suppress arachidonic acid release, acetylcholine release, intracellular $Ca^{2+}$ release, intracellular cAMP production, intracellular cGMP production, inositolphosphate production, cell membrane potential changes, intracellular protein phosphorylation, c-fos activation, pH reduction and the like, and the like) by increasing the expression amount of SS169, or (b) a compound that weakens the cell stimulation activity by reducing the expression amount of SS169.

As the compound used, peptides, proteins, non-peptide compounds, synthetic compounds, fermentation products and the like can be mentioned; these compounds may be novel compounds or known compounds.

A compound that enhances the cell stimulation activity is useful as a safe and less toxic pharmaceutical for enhancing a physiological activity of SS169.

A compound that weakens the cell stimulation activity is useful as a safe and less toxic pharmaceutical for reducing a physiological activity of SS169.

When a compound obtained using the above-described screening method or a salt thereof is used as a pharmaceutical, it can be formulated in the same manner as with the aforementioned "prophylactic/therapeutic agent for a disease associated with SS169 dysfunction".

Because the preparation thus obtained is safe and less toxic, it can be administered to, for example, a mammal (for example, humans, rats, rabbits, sheep, swine, cattle, cats, dogs, monkeys and the like).

The dose of the compound or a salt thereof varies depending on the subject of administration, target organ, symptoms, method of administration and the like; in oral administration, the dose is normally about 0.1 to 100 mg, preferably about 1.0 to 50 mg, and more preferably about 1.0 to 20 mg, per day, in, for example, a patient with a sugar/lipid metabolic abnormality (assuming a 60 kg body weight). In parenteral administration, the single dose varies depending on the subject of administration, target organ, symptoms, method of administration and the like; for example, in the form of an injection, the dose is normally about 0.01 to 30 mg, preferably about 0.1 to 20 mg, and more preferably about 0.1 to 10 mg, per day, in, for example, a patient with a sugar/lipid metabolic abnormality (assuming a 60 kg body weight). In cases where the subject of administration is other than a human, a dose corresponding to a human dose per 60 kg body weight can be administered.

(6) Prophylactic/Therapeutic Agents for Various Diseases Comprising a compound that changes the expression amount of SS169

As stated above, SS169 is expressed nearly specifically in skeletal muscles and highly expressed in diabetic model mice and during re-feeding after fasting; for these and other reasons, SS169 is considered to play an important role in the regulation of (i) skeletal muscle cell differentiation and/or (ii) metabolism [examples include, but are not limited to, metabolism (particularly sugar/lipid metabolism) in the liver, adipose tissue, skeletal muscles, pancreas and the like, and the like; the same applies below]. Therefore, a compound that changes the expression amount of SS169 can be used as a prophylactic/therapeutic agent for a disease involved in differentiation of skeletal muscle cell and/or metabolic abnormality (hypofunction or hyperfunction) (for example, obesity, diabetes mellitus, impaired glucose tolerance, arteriosclerosis, hypertension, hyperlipemia and the like).

When the compound is used as a prophylactic/therapeutic agent for a disease associated with SS169 hypofunction or hyperfunction, it can be formulated in the same manner as the aforementioned "prophylactic/therapeutic agent for a disease associated with SS169 dysfunction".

Because the preparation thus obtained is safe and less toxic, it can be administered to, for example, a mammal (for example, humans, rats, rabbits, sheep, swine, cattle, cats, dogs, monkeys and the like).

The dose of the compound or a salt thereof varies depending on the subject of administration, target organ, symptoms, method of administration and the like; in oral administration, the dose is normally about 0.1 to 100 mg, preferably about 1.0 to 50 mg, and more preferably about 1.0 to 20 mg, per day, in, for example, a patient with a sugar/lipid metabolic abnormality (assuming a 60 kg body weight). In parenteral administration, the single dose varies depending on the subject of administration, target organ, symptoms, method of administration and the like; for example, in the form of an injection, the dose is normally about 0.01 to 30 mg, preferably about 0.1 to 20 mg, and more preferably about 0.1 to 10 mg, per day, in, for example, a patient with a sugar/lipid metabolic abnormality (assuming a 60 kg body weight). In cases where the subject of administration is other than a human, a dose corresponding to a human dose per 60 kg body weight can be administered.

(7) Method of Quantifying a Compound Having Specific Affinity for SS169 (Ligand or Receptor)

Because an SS169 species has bindability for a ligand (or receptor) for SS169, it enables highly sensitive quantitation of the concentration of the ligand (or receptor) in vivo.

The method of quantitation of the present invention can be used in combination with, for example, the competitive method. That is, by bringing a test sample in contact with an SS169 species, the ligand (or receptor) concentration in the test sample can be measured. Specifically, for example, the method of quantitation of the present invention can be used according to a method described in (1) or (2) below and the like or a method based thereon.

(1) Hiroshi Irie, ed., "Radioimmunoassay" (Kodansha Ltd., published in 1974)
(2) Hiroshi Irie, ed., "Sequel to the Radioimmunoassay" (Kodansha Ltd., 1979)

(8) A Method of Screening a Compound (Agonist, Antagonist and the Like) that Changes the Bindability Between SS169 and a Compound Having Specific Affinity for SS169 (Ligand or Receptor)

A compound that changes the bindability between SS169 and its ligand (or receptor) (e.g., peptides, proteins, non-peptide compounds, synthetic compounds, fermentation products and the like) or a salt thereof can be efficiently screened by using an SS169 species, or by constructing an expression system for recombinant SS169, and using an affinity assay system based on the expression system.

Such compounds include (i) a compound having a cell stimulation activity (e.g., activities that promote or suppress arachidonic acid release, acetylcholine release, intracellular $Ca^{2+}$ release, intracellular cAMP production, intracellular cGMP production, inositolphosphate production, cell membrane potential changes, intracellular protein phosphorylation, c-fos activation, pH reduction and the like) via a receptor (agonist), (ii) a compound not having the cell stimulation activity (antagonist), (iii) a compound that enhances the bindability between SS169 and its ligand (or receptor), or (iv) a compound that reduces the bindability between SS169 and its ligand (or receptor) (compound (i) above is preferably screened by the above-described method of ligand identification).

Accordingly, the present invention provides a method of screening a compound that changes the bindability between SS169 and its ligand (or receptor) or a salt thereof, which comprises comparing (i) a case wherein an SS169 species is brought into contact with its ligand (or receptor) and (ii) a case wherein an SS169 species is brought into contact with its ligand (or receptor) and a test compound.

A feature of the above-described screening method resides in that the binding amount of a ligand (or receptor) for SS169, a cell stimulation activity or the like is measured and compared between cases (i) and (ii).

More specifically, the present invention provides:

(1) a method of screening a compound that changes the bindability between SS169 and its ligand (or receptor) or a salt thereof, which comprises measuring and comparing the amounts of labeled ligand (or receptor) bound to SS169 species when the labeled ligand (or receptor) is brought into contact with the SS169 species and when the labeled ligand (or receptor) and a test compound are brought into contact with the SS169 species, (2) a method of screening a compound that changes the bindability between SS169 and its ligand (or receptor) or a salt thereof, which comprises measuring and comparing the amounts of labeled ligand (or receptor) bound to SS169-producing cells or a membrane fraction thereof, or to an extracellular fluid or cell culture supernatant when the labeled ligand (or receptor) is brought into contact with the cells or membrane fraction, or with the extracellular fluid or cell culture supernatant (in this case, for example, SS169 is immobilized using the above-described solid phase (cell culture plate and the like) having the antibody of the present invention immobilized thereon), and when the labeled ligand (or receptor) and a test compound are brought into contact with SS169-producing cells or a membrane fraction thereof, or with an extracellular fluid or cell culture supernatant, (3) a method of screening a compound that changes the bindability between SS169 and its ligand (or receptor) or a salt thereof, which comprises measuring and comparing the amounts of labeled ligand (or receptor) bound to an SS169 species when the labeled ligand (or receptor) is brought into contact with an SS169 species expressed on the cell membrane by culturing a transformant bearing the DNA of the present invention, or with an SS169 species secreted in the culture supernatant (in this case, for example, the SS169 species is immobilized using the above-described solid phase (cell culture plate and the like) having the antibody of the present invention immobilized thereon), and when the labeled ligand (or receptor) and a test compound are brought into contact with an SS169 species expressed on the cell membrane by culturing a transformant bearing the DNA of the present invention, or with an SS169 species secreted in the culture supernatant, (4) a method of screening a compound that changes the bindability between SS169 and its ligand (or receptor) or a salt thereof, which comprises measuring and comparing the levels of a cell stimulation activity mediated by a receptor (for example, activities that promote or suppress arachidonic acid release, acetylcholine release, intracellular $Ca^{2+}$ release, intracellular cAMP production, intracellular cGMP production, inositolphosphate production, cell membrane potential changes, intracellular protein phosphorylation, c-fos activation, pH reduction and the like, and the like) when a compound that activates SS169 (for example, ligand for SS169 and the like) or a compound activated by SS169 (for example, receptor for SS169 and the like) is brought into contact with cells expressing SS169 on the cell membrane or a culture supernatant in which SS169 is secreted, and when a compound that activates SS169 or a compound activated by SS169 and a test compound are brought into contact with cells expressing SS169 on the cell membrane or a culture supernatant in which SS169 is secreted, and (5) a method of screening a compound that changes the bindability between SS169 and its ligand (or receptor) or a salt thereof, which comprises measuring and comparing the levels of a cell stimulation activity mediated by a receptor (for example, activities that promote or suppress arachidonic acid release, acetylcholine release, intracellular $Ca^{2+}$ release, intracellular CAMP production, intracellular cGMP production, inositolphosphate production, cell membrane potential changes, intracellular protein phosphorylation, c-fos activation, pH reduction and the like, and the like) when a compound that activates SS169 (for example, ligand for SS169 and the like) or a compound activated by SS169 (for example, receptor for SS169 and the like) is brought into contact with an SS169 species expressed on the cell membrane by culturing a transformant bearing the DNA of the present invention, or with an SS169 species secreted in the culture supernatant by culturing a transformant bearing the DNA of the present invention, and when a compound that activates SS169 or a compound activated by SS169 and a test compound are brought into contact with an SS169 species expressed on the cell membrane by culturing a transformant bearing the DNA of the present invention, or with an SS169 species secreted in the culture supernatant by culturing a transformant bearing the DNA of the present invention.

The screening method of the present invention is hereinafter described specifically.

First, the SS169 species used in the screening method of the present invention may be any one comprising the above-described SS169 or a partial peptide thereof or a salt thereof, and the cell membrane fraction or extracellular fluid of an organ of an SS169-producing mammal is preferred. However, because human-derived organs, in particular, are extremely difficult to obtain, the SS169 species used in the screening method of the present invention is preferably a human-derived SS169 species expressed in a large amount using a transformant.

An SS169 species is produced using the method described above, which is preferably performed by expressing the DNA of the present invention in mammalian cells or insect cells. A cDNA is normally used as the DNA fragment encoding the desired portion of the protein, but is not construed as limiting. For example, a gene fragment or a synthetic DNA may also be used. For introducing a DNA fragment encoding SS169 or a partial peptide thereof into host animal (or insect) cells and efficiently expressing the same, it is preferable to insert the DNA fragment downstream of an SV40-derived promoter, a retrovirus promoter, a metallothionein promoter, a human heat shock promoter, a cytomegalovirus promoter, an SRα promoter, the polyhedrin promoter of nuclear polyhedrosis virus (NPV), which is a baculovirus having insect hosts, or the like.

Therefore, the SS169 species used in the screening method of the present invention may be an SS169 species purified according to a method known per se, or may be used as cells producing the SS169 species or a cell membrane fraction thereof, or a culture supernatant of cells secreting the SS169 species.

In the above-described screening method, when using cells producing an SS169 species, the cells may be fixed with glutaraldehyde, formalin and the like. This fixation can be performed according to a method known per se.

Cells producing an SS169 species refer to host cells expressing the SS169 species; as the host cells, *Escherichia coli, Bacillus subtilis*, yeasts, insect cells, animal cells and the like can be used.

The aforementioned cell membrane fraction refers to a fraction rich in cell membrane obtained by a method known per se after cell disruption. As the method of cell disruption, cell squashing using a Potter-Elvehjem homogenizer, disruption using a Waring blender or Polytron (manufactured by Kinematica Inc.), disruption by ultrasonication, disruption by cell spraying through a thin nozzle under an increased pressure using a French press or the like, and the like can be mentioned. For cell membrane fractionation, fractionation by centrifugal forces, such as fractional centrifugation or density gradient centrifugation, is mainly used. For example, a cell disruption fluid is centrifuged at a low speed (500 rpm to 3000 rpm) for a short time (normally about 1 to 10 minutes), the supernatant is centrifuged at a higher speed (15000 rpm to 30000 rpm) normally for 30 minutes to 2 hours, and the precipitate obtained is used as the membrane fraction. The membrane fraction is rich in the SS169 species expressed and cell-derived membrane components such as phospholipids and membrane proteins.

The amount of SS169 species in the cells producing the SS169 species and the membrane fraction thereof is preferably $10^3$ to $10^8$ molecules per cell, more preferably $10^5$ to $10^7$ molecules. Note that as the expression amount increases, ligand-binding activity per unit of membrane fraction (specific activity) increases so that it is possible to construct a highly sensitive screening system, and to assay a large number of samples in the same lot.

To perform methods (1) to (3) above for screening a compound that changes the bindability between SS169 and its ligand, for example, an appropriate SS169 species-containing membrane fraction and labeled ligand are necessary.

As the SS169-containing membrane fraction, a naturally occurring SS169-containing membrane fraction or a recombinant SS169 species-containing membrane fraction having an activity equivalent to that thereof, or the like is desirable. As used herein, equivalent activity means equivalent ligand-binding activity, signal transmission activity or the like.

As the labeled ligand, a labeled ligand, a labeled ligand analogue compound and the like can be used. For example, a ligand and the like labeled with $[^3H]$, $[^{125}I]$, $[^{14}C]$, $[^{35}S]$ or the like are used.

Specifically, to perform screening of a compound that changes the bindability between SS169 and its ligand, cells producing an SS169 species or a membrane fraction thereof is first suspended in a buffer suitable for the screening to prepare a standard preparation of SS169 species. The buffer may be any buffer that does not interfere with the binding of SS169 and its ligand, such as a phosphate buffer or Tris-hydrochloride buffer having a pH value of 4 to 10 (desirably a pH value of 6 to 8). To reduce non-specific binding, a surfactant such as CHAPS, Tween-80 (Kao-Atlas Co.), digitonin or deoxycholate may be added to the buffer. Furthermore, to suppress the degradation of receptors and ligands by proteases, a protease inhibitor such as PMSF, leupeptin, E-64 (manufactured by Peptide Research Laboratory, Co.), or pepstatin may be added. A given amount (5,000 cpm to 500,000 cpm) of a labeled ligand is added to 0.01 ml to 10 ml of a suspension of SS169 species, in the presence of a $10^{-4}$M to $10^{-10}$M test compound. To determine non-specific binding (NSB), a reaction tube containing the unlabeled ligand in large excess is also provided. The reaction is performed at about 0° C. to 50° C., desirably about 4° C. to 37° C., for about 20 minutes to 24 hours, desirably about 30 minutes to 3 hours. After the reaction, the reaction mixture is filtered through glass fiber filter paper and the like, and washed with an appropriate amount of the same buffer; thereafter, the residual radioactivity on the glass fiber filter paper is counted using a liquid scintillation counter or a γ-counter. A test compound showing a specific binding (B-NSB) of, for example, not more than 50%, as the percent ratio to the count ($B_0$-NSB) calculated by subtracting non-specific binding (NSB) from the count in the absence of antagonizing substance ($B_0$), can be selected as a candidate substance capable of inhibiting the antagonism.

To perform methods (4) and (5) above for screening a compound that changes the bindability between SS169 and its ligand, for example, a cell stimulation activity mediated by SS169 (for example, activities that promote or suppress arachidonic acid release, acetylcholine release, intracellular $Ca^{2+}$ release, intracellular cAMP production, intracellular cGMP production, inositolphosphate production, cell membrane potential changes, intracellular protein phosphorylation, c-fos activation, pH reduction and the like, and the like) can be measured using a known method or a commercially available assay kit.

Specifically, first, cells producing an SS169 species are cultured on a multi-well plate or the like. In performing the screening, the medium is replaced with a fresh medium or an appropriate non-cytotoxic buffer in advance, and a test compound and the like are added, followed by incubation for a given time; thereafter, the cells are extracted or the supernatant is recovered, and the resulting product is quantified by each method. If it is difficult to detect the production of an indicator substance for cell stimulation activity (for example, arachidonic acid and the like) due to a degrading enzyme contained in the cells, the assay may be performed with the addition of an inhibitor of the degrading enzyme. Activities such as cAMP-production suppression can be detected as suppressive effects on the production of cells having baseline production previously increased with forskolin or the like.

To perform the screening with a measurement of a cell stimulation activity, appropriate cells expressing an SS169 species on the membrane thereof are necessary. As the cells expressing an SS169 species, cell lines producing naturally occurring SS169, cell lines expressing the aforementioned recombinant SS169 species and the like are desirable.

As examples of the test compound used, peptides, proteins, non-peptide compounds, synthetic compounds, fermentation products, cell extracts, plant extracts, animal tissue extracts and the like can be mentioned; these compounds may be novel compounds or known compounds.

Although a method of screening a compound that changes the bindability between SS169 and its ligand (or receptor) or a salt thereof has been described specifically with reference to a case wherein SS169 is a membrane protein, those skilled in the art can easily screen a compound that changes the bindability between SS169 and its receptor by applying the above-described technique even when SS169 is a secretory protein.

The screening kit for a compound that changes the bindability between SS169 and a compound having specific affinity therefor (ligand or receptor) or a salt thereof comprises an SS169 species, cells producing an SS169 species or a membrane fraction thereof, or a culture supernatant of cells secreting an SS169 species, and the like.

As examples of the screening kit of the present invention, the following can be mentioned.

1. Screening Reagents (1) Assay Buffer Solution and Wash Buffer Solution

Hanks' balanced salt solution (manufactured by Gibco Co.) supplemented with 0.05% bovine serum albumin (manufactured by Sigma Co.).

The solution is sterilized by filtration through a filter of 0.45 μm pore size and stored at 4° C., or may be prepared freshly just before use.

(2) Standard Preparation of SS169 Species

CHO cells expressing an SS169 species are subcultured on a 12-well plate at a density of $5\times10^5$ cells/well and cultured at 37° C. under 5% $CO_2$ and 95% air for 2 days (when the SS169 species is secreted, the plate is coated with anti-SS169 antibody).

(3) Labeled Ligand (Receptor)

A commercially available ligand (receptor) labeled with [$^3$H] [$^{125}$I] [$^{14}$C] [$^{35}$S] or the like.

An aqueous solution of the ligand (receptor) is stored at 4° C. or −20° C. and diluted to 1 μM with the assay buffer solution just before use.

(4) Standard Solution of Ligand (Receptor)

The ligand (receptor) is dissolved in PBS containing 0.1% bovine serum albumin (manufactured by Sigma Co.) to obtain a concentration of 1 mM, and stored at −20° C.

As the labeled receptor and standard receptor solution, proteoliposome, which comprises the receptor protein embedded in a liposome membrane composed of an appropriate lipid composition, may be used in suspension in an appropriate dispersant (water, PBS and the like) after being stored at 4° C.

2. Assay Method (1) After SS169 species-expressing CHO cells cultured on a 12-well tissue culture plate are washed twice with 1 ml of the assay buffer solution (when the SS169 species is secreted, after the cells and culture supernatant are removed and then the plate is washed with the assay buffer solution in the same manner), 490 μl of the assay buffer solution is added to each well.

(2) After 5 μl of $10^{-3}$ to $10^{-10}$M test compound solution is added, 5 μl of a labeled ligand (or receptor) is added and the reaction is performed at room temperature for 1 hour. To determine non-specific binding, 5 μl of $10^{-3}$M standard ligand (or receptor) solution, instead of the test compound, is added in advance.

(3) The reaction liquid is removed and the wells are washed 3 times with 1 ml of the wash buffer solution. The labeled ligand (or receptor) bound to the cells (or plate) is dissolved in 0.2N NaOH-1% SDS, and mixed with 4 ml of liquid scintillator A (manufactured by Wako Pure Chemical Industries, Ltd.).

(4) Radioactivity is measured using a liquid scintillation counter (manufactured by Beckman Co.), and percent maximum binding (PMB) is calculated using the following equation [Equation 1].

$$PMB=[(B-NSB)/(B_0-NSB)]\times100 \quad \text{[Equation 1]}$$

PMB: percent maximum binding
B: value obtained in the presence of test compound
NSB: non-specific binding
$B_0$: maximum binding The compound obtained using the above-described screening method or screening kit or a salt thereof is a compound that acts to change the bindability between SS169 and a compound having specific affinity therefor (ligand or receptor), specifically, (i) a compound having a cell stimulation activity (for example, activities that promote or suppress arachidonic acid release, acetylcholine release, intracellular $Ca^{2+}$ release, intracellular cAMP production, intracellular cGMP production, inositolphosphate production, cell membrane potential changes, intracellular protein phosphorylation, c-fos activation, pH reduction and the like, and the like) mediated by ligand-receptor interaction (agonist), (ii) a compound not having the cell stimulation activity (antagonist), (iii) a compound that enhances the bindability between SS169 and its ligand (or receptor), or (iv) a compound that reduces the bindability between SS169 and its ligand (or receptor).

As the compound used, peptides, proteins, non-peptide compounds, synthetic compounds, fermentation products and the like can be mentioned; these compounds may be novel compounds or known compounds.

Because an agonist for SS169 (or SS169 receptor) has a similar physiological activity to that of a ligand for SS169 (or of SS169), it is useful as a safe and less toxic pharmaceutical depending on the ligand activity.

Because an antagonist for SS169 (or SS169 receptor) is capable of suppressing a physiological activity of a ligand for SS169 (or of SS169), it is useful as a safe and less toxic pharmaceutical for suppressing the ligand activity.

A compound that enhances the bindability between SS169 and its ligand (or receptor) is useful as a safe and less toxic pharmaceutical for enhancing a physiological activity of a ligand (or SS169).

A compound that reduces the bindability between SS169 and its ligand (or receptor) is useful as a safe and less toxic pharmaceutical for reducing a physiological activity of a ligand for SS169 (or of SS169).

When a compound obtained using the above-described screening method or screening kit or a salt thereof is used as a pharmaceutical, it can be formulated in the same manner as with the aforementioned "prophylactic/therapeutic agent for a disease associated with SS169 dysfunction".

Because the preparation thus obtained is safe and less toxic, it can be administered to, for example, mammals (for example, humans, rats, rabbits, sheep, swine, cattle, cats, dogs, monkeys and the like).

The dose of the compound or a salt thereof varies depending on the subject of administration, target organ, symptoms, method of administration and the like; in oral administration, the dose is normally about 0.1 to 100 mg, preferably about 1.0 to 50 mg, and more preferably about 1.0 to 20 mg, per day, in, for example, a patient with a sugar/lipid metabolic abnormality (assuming a 60 kg body weight). In parenteral administration, the single dose varies depending on the subject of administration, target organ, symptoms, method of administration and the like; for example, in the form of an injection, the dose is normally about 0.01 to 30 mg, preferably about 0.1 to 20 mg, and more preferably about 0.1 to 10 mg, per day, in, for example, a patient with a sugar/lipid metabolic abnormality (assuming a 60 kg body weight). In cases where the subject of administration is other than a human, a dose corresponding to a human dose per 60 kg body weight can be administered.

(9) Prophylactic/Therapeutic Agents for Various Diseases Containing a Compound that Changes the Bindability Between SS169 and a Compound Having Specific Affinity for SS169 (Ligand or Receptor) (Agonist, Antagonist)

As stated above, SS169 is expressed nearly specifically in skeletal muscles and highly expressed in diabetic model mice and during re-feeding after fasting; for these and other reasons, SS169 is considered to play an important role in the regulation of differentiation of skeletal muscle cell and/or metabolism (particularly sugar/lipid metabolism). Therefore, a compound that changes the bindability between SS169 and its ligand (or receptor) (agonist, antagonist) can be used as a prophylactic/therapeutic agent for a disease involved in differentiation of skeletal muscle cell and/or metabolic abnormality (hypofunction or hyperfunction) (for example, obesity, diabetes mellitus, impaired glucose tolerance, arteriosclerosis, hypertension, hyperlipemia and the like).

When the compound is used as a prophylactic/therapeutic agent for a disease associated with SS169 hypofunction or hyperfunction, it can be formulated in the same manner as the aforementioned "prophylactic/therapeutic agent for a disease associated with SS169 dysfunction".

Because the preparation thus obtained is safe and less toxic, it can be administered to, for example, mammals (for example, humans, rats, rabbits, sheep, swine, cattle, cats, dogs, monkeys and the like).

The dose of the compound or a salt thereof varies depending on the subject of administration, target organ, symptoms, method of administration and the like; in oral administration, the dose is normally about 0.1 to 100 mg, preferably about 1.0 to 50 mg, and more preferably about 1.0 to 20 mg, per day, in, for example, a patient with a sugar/lipid metabolic abnormality (assuming a 60 kg body weight). In parenteral administration, the single dose varies depending on the subject of administration, target organ, symptoms, method of administration and the like; for example, in the form of an injection, the dose is normally about 0.01 to 30 mg, preferably about 0.1 to 20 mg, and more preferably about 0.1 to 10 mg, per day, in, for example, a patient with a sugar/lipid metabolic abnormality (assuming a 60 kg body weight). In cases where the subject of administration is other than a human, a dose corresponding to a human dose per 60 kg body weight can be administered.

(10) Quantitation of SS169 Species

Because the antibody of the present invention is capable of specifically recognizing an SS169 species, it can be used for quantitation of SS169 species in a test fluid, particularly quantitation by sandwich immunoassay, and the like. Accordingly, the present invention provides, for example, (i) a method of quantifying an SS169 species in a test fluid, which comprises competitively reacting the antibody of the present invention and the test fluid, a labeled protein and the like, and measuring the ratio of labeled protein and the like bound to the antibody, and (ii) a method of quantifying an SS169 species in a test fluid, which comprises simultaneously or sequentially reacting the test fluid, the antibody of the present invention as immobilized on a carrier, and the antibody of the present invention as labeled, and measuring the activity of labeling agent on the insolubilizing carrier.

In (ii) above, the insolubilized antibody and the labeled antibody preferably have antigen recognition sites such that they do not mutually interfere with their binding to SS169 species (for example, one antibody recognizes the N-terminus of the SS169 species, and the other antibody reacts with the C-terminus of the SS169 species, and the like).

Using a monoclonal antibody against an SS169 species (hereinafter sometimes referred to as the monoclonal antibody of the present invention), the SS169 species can be measured, and can also be detected by tissue staining and the like. For these purposes, the antibody molecule itself may be used, and the F(ab')2, Fab' or Fab fraction of the antibody molecule may also be used. The assay method using an antibody against an SS169 species is not to be subject to limitation; any assay method can be used, as long as the amount of antibody, antigen, or antibody-antigen complex corresponding to the amount of antigen (for example, the amount of SS169) in a test fluid is detected by a chemical or physical means and calculated from a standard curve generated using standard solutions containing known amounts of antigen. For example, nephelometry, the competitive method, immunometric method, and sandwich method are advantageously used, with preference given to the sandwich method described below, in terms of sensitivity and specificity.

As examples of the labeling agent used for the assay method using a labeled substance, radioisotopes, enzymes, fluorescent substances, luminescent substances and the like can be mentioned. As examples of the radioisotopes used, [$^{125}$I], [$^{131}$I], [$^{3}$H], [$^{14}$C] and the like can be mentioned. As examples of the enzymes, stable enzymes of high specific activity are preferred; for example, β-galactosidase, β-glucosidase, alkaline phosphatase, peroxidase, malate dehydrogenase and the like can be mentioned. As examples of the fluorescent substances, fluorescamine, fluorescein isothiocyanate and the like can be mentioned. As examples of the luminescent substances, luminol, luminol derivatives, luciferin, lucigenin and the like can be mentioned. Furthermore, the biotin-avidin system may also be used for the binding of an antibody or antigen and the labeling agent.

For insolubilization of the antigen or antibody, physical adsorption may be used, and methods based on chemical binding, which are normally used to insolubilize or immobilize proteins or enzymes and the like, may also be used. As examples of the carrier, insoluble polysaccharides such as agarose and dextran; synthetic resins such as polystyrene, polyacrylamide and silicone; glass and the like can be used.

In the sandwich method, the monoclonal antibody of the present invention as insolubilized is reacted with a test fluid (primary reaction), and further reacted with the monoclonal antibody of the present invention as labeled (secondary reaction), and the activity of the labeling agent on the insolubilizing carrier is then measured, whereby the amount of SS169 in the test fluid can be quantified. The primary and secondary reactions may be performed in the reverse order, and may be performed simultaneously or at a time interval. The labeling agent and the method of insolubilization may be the same as those described above.

In immunoassays by the sandwich method, the antibody used for an immobilized antibody or a labeled antibody need not always be one kind; a mixture of two or more kinds of antibodies may be used to increase assay sensitivity.

In assaying an SS169 species by the sandwich method, the monoclonal antibodies of the present invention used for the primary and secondary reactions are preferably antibodies having mutually different sites for binding with the SS169 species. That is, regarding the antibodies used for the primary and secondary reactions, for example, when the antibody used for the secondary reaction recognizes the C-terminus region of the SS169 species, the antibody used for the primary reaction is preferably an antibody that recognizes a region other than the C-terminus region, for example, the N-terminus region.

The monoclonal antibody of the present invention can be used for assay systems other than the sandwich method, for example, the competitive method, immunometric method, nephelometry and the like. In the competitive method, an antigen in a test fluid and a labeled antigen are competitively reacted with an antibody, then the unreacted labeled antigen (F) and the labeled antigen bound to the antibody (B) are separated (B/F separation); the amount of labeled antigen in B or F is measured to quantify the amount of antigen in the test fluid. For this reaction, the liquid phase method, which uses a soluble antibody and polyethylene glycol and a secondary antibody to the above-described antibody and the like for B/F separation, and the immobilization method, which uses a soluble primary antibody and a solid-immobilized secondary antibody, are available.

In the immunometric method, an antigen in a test fluid and an immobilized antigen are competitively reacted with a given amount of labeled antibody, and thereafter the solid phase is separated from the liquid phase, or an antigen in a test fluid is reacted with an excess amount of labeled antibody, an immobilized antigen is then added to bind the unreacted labeled antibody to the solid phase, and the solid phase is separated from the liquid phase. Subsequently, the amount of labeled antibody in either phase is measured to quantify the amount of antigen in the test fluid.

In nephelometry, the amount of insoluble precipitate from the antigen-antibody reaction within the gel or in the solution is measured. Even when the amount of antigen in the test fluid is small and only a small amount of precipitate is obtained, laser nephelometry, which is based on laser scattering, and the like can be used advantageously.

In applying these individual immunoassays to the quantification of an SS169 species, no special conditions, procedures or the like need to be set forth. The assay system for the SS169 species may be constructed with ordinary technical considerations of those skilled in the art on ordinary conditions and procedures in the respective methods. For details of these general techniques, reference can be made to reviews, texts and the like [see, for example, Hiroshi Irie, ed., "Radioimmunoassay" (Kodansha Ltd., published in 1974), Hiroshi Irie, ed., "Sequel to the Radioimmunoassay" (Kodansha Ltd., published in 1979), Eiji Ishikawa et al., ed., "Enzyme Immonoassay" (Igakushoin, published in 1978), Eiji Ishikawa et al., ed., "Enzyme Immonoassay" (2nd ed.) (Igakushoin, published in 1982), Eiji Ishikawa et al., ed., "Enzyme Immonoassay" (3rd ed.) (Igakushoin, published in 1987), Methods in ENZYMOLOGY, Vol. 70 (Immunochemical Techniques (Part A)), ibidem, Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibidem, Vol. 92 (Immunochemical Techniques (Part E: Monoclonal Antibodies and General Immunoassay Methods)), ibidem, Vol. 121 (Immunochemical Techniques (Part I: Hybridoma Technology and Monoclonal Antibodies)) (all published by Academic Press Publishing) and the like].

As described above, an SS169 species can be quantified highly sensitively by using the antibody of the present invention.

Furthermore, various diseases associated with SS169 hypofunction or hyperfunction can be diagnosed by quantifying SS169 or a salt thereof in vivo using the antibody of the present invention.

The antibody of the present invention can also be used to specifically detect SS169 or a salt thereof present in a test sample such as body fluid or tissue. The antibody of the present invention can also be used to prepare an antibody column for purification of an SS169 species, to detect an SS169 species in each fraction during purification, to analyze the behavior of SS169 in subject cells, and the like.

(11) Method of Screening a Compound that Changes the Amount of SS169 in the Cell Membrane or Outside the Cells Because the antibody of the present invention is capable of specifically recognizing an SS169 species, it can be used for screening a compound that changes the amount of SS169 in the cell membrane or outside the cells.

Accordingly, the present invention provides, for example:

(i) a method of screening a compound that changes the amount of SS169 in the cell membrane, which comprises disrupting (1) blood, (2) a particular organ, or (3) a tissue, cells or the like isolated from an organ, of a non-human mammal, then isolating a cell membrane fraction, and quantifying the SS169 contained the cell membrane fraction (or a method of screening a compound that changes the amount of SS169 outside the cells, which comprises separating an extracellular fluid such as blood, urine or another body fluid, of a non-human mammal, and quantifying the SS169 contained therein), (ii) a method of screening a compound that changes the amount of SS169 in the cell membrane, which comprises disrupting a transformant expressing SS169 or a partial peptide thereof, or the like, then isolating a cell membrane fraction, and quantifying the SS169 species contained in the cell membrane fraction (or a method of screening a compound that changes the amount of SS169 outside the cells, which comprises separating a culture supernatant of a transformant expressing SS169 or a partial peptide thereof, and quantifying the SS169 species contained in the culture supernatant), (iii) a method of screening a compound that changes the amount of SS169 in the cell membrane, which comprises identifying SS169 on the cell membrane by cutting into sections (1) blood, (2) a particular organ, or (3) a tissue, cells or the like isolated from an organ, of a non-human mammal, then quantifying the extent of staining of SS169 on the cell surface layer using an immunostaining technique, and (iv) a method of screening a compound that changes the amount of SS169 species in the cell membrane, which comprises identifying the SS169 species on the cell membrane by cutting into sections a transformant expressing SS169 or a partial peptide thereof, or the like, then quantifying the extent of staining of the SS169 species on the cell surface layer using an immunostaining technique.

Quantitation of the SS169 species contained in the cell membrane fraction is specifically performed as described below.

(i) A drug (for example, anti-obesity drugs, anti-diabetic drugs, antihypertensive drugs, vasoactive drugs, anticancer agents and the like) or a physical stress (for example, soaking stress, electric shock, brightness/darkness, low temperatures and the like) or the like is given to a normal or disease model non-human mammal (for example, mice, rats, rabbits, sheep, swine, cattle, cats, dogs, monkeys and the like, more specifically, obese mice, diabetic mice, hypertensive rats, arteriosclerotic rabbits, cancer-bearing mice and the like); after a given time has elapsed, blood or a particular organ (for example, liver, kidney, pancreas, muscles and the like), a tissue (for example, brown or white adipose tissue and the like) or cells (for example, adipocytes, muscle cells or the like) are obtained. The cells and the like obtained are suspended in an appropriate buffer solution (for example, Tris-HCl buffer solution, phosphate buffer solution, HEPES buffer solution and the like) and the like, and the cells or the like are disrupted using a surfactant (for example, Triton X100™, Tween 20™ and the like) and the like, and further treated using techniques such as centrifugation, filtration and column fractionation to yield a cell membrane fraction.

The cell membrane fraction refers to a fraction rich in cell membrane obtained by a method known per se after cell disruption. As the method of cell disruption, cell squashing using a Potter-Elvehjem homogenizer, disruption using a Waring blender or Polytron (manufactured by Kinematica Inc.), disruption by ultrasonication, disruption by cell spraying through a thin nozzle under an increased pressure using a French press or the like, and the like can be mentioned. For cell membrane fractionation, fractionation by centrifugal forces, such as fractional centrifugation or density gradient centrifugation, is mainly used. For example, a cell disruption fluid is centrifuged at a low speed (500 rpm to 3000 rpm) for a short time (normally about 1 to 10 minutes), the supernatant is centrifuged at a higher speed (15000 rpm to 30000 rpm) normally for 30 minutes to 2 hours, and the precipitate obtained is used as the membrane fraction. The membrane fraction is rich in SS169 species and cell-derived membrane components such as phospholipids and membrane proteins.

The SS169 species contained in the cell membrane fraction can be quantified by, for example, a sandwich immunoassay using the antibody of the present invention, Western blot analysis and the like.

The sandwich immunoassay can be performed in the same manner as the method described above, and Western blot can be performed by a means known per se.

(ii) A transformant expressing SS169 or a partial peptide thereof can be prepared according to the method described above, and the SS169 species contained in the cell membrane fraction can be quantified.

Screening of a compound that changes the amount of SS169 in the cell membrane can be performed by:

(i) administering a test compound to a normal or disease model non-human mammal at a given time before (before 30 minutes to before 24 hours, preferably before 30 minutes to before 12 hours, more preferably before 1 hour to before 6 hours) or after (after 30 minutes to after 3 days, preferably after 1 hour to after 2 days, more preferably after 1 hour to after 24 hours) a drug, a physical stress or the like is given, or at the same time as the drug or physical stress, and quantifying the amount of SS169 in the cell membrane after a given time has elapsed after administration (after 30 minutes to after 3 days, preferably after 1 hour to after 2 days, more preferably after 1 hour to after 24 hours), and can also be preformed by:

(ii) mixing a test compound in a medium at the start of cultivation of a transformant according to a conventional method, and quantifying the amount of SS169 species in the cell membrane after cultivation for a given time (after 1 day to after 7 days, preferably after 1 day to after 3 days, more preferably after 2 days to after 3 days).

Identification of the SS169 species contained in the cell membrane fraction is specifically performed as described below.

(iii) A drug (for example, anti-obesity drugs, anti-diabetic drugs, antihypertensive drugs, vasoactive drugs, anticancer agents and the like) or a physical stress (for example, soaking stress, electric shock, brightness/darkness, low temperatures and the like) or the like is given to a normal or disease model non-human mammal (for example, mice, rats, rabbits, sheep, swine, cattle, cats, dogs, monkeys and the like, more specifically, obese mice, diabetic mice, hypertensive rats, arteriosclerotic rabbits, cancer-bearing mice and the like); after a given time has elapsed, blood or a particular organ (for example, liver, kidney, pancreas, muscles and the like), a tissue (for example, brown or white adipose tissue and the like) or cells (for example, adipocytes, muscle cells and the like) are obtained. The cells or the like obtained are cut into tissue sections according to a conventional method, and immunostaining is performed using the antibody of the present invention. The amount of SS169 species in the cell membrane can be determined, quantitatively or qualitatively, by quantifying the extent of staining of SS169 on the cell surface layer to identify the SS169 on the cell membrane.

(iv) The SS169 species contained in a cell membrane fraction can also be identified in a similar way using a transformant expressing SS169 or a partial peptide thereof and the like.

Although a method of screening a compound that changes the amount of SS169 in the cell membrane has been described specifically with reference to a case wherein SS169 is a membrane protein in the above-described screening method, it is evident that those skilled in the art can also easily screen a compound that changes the amount of SS169 outside the cells by applying the above-described technique even when SS169 is a secretory protein.

The compound obtained using the above-described screening method or a salt thereof is a compound that acts to change the amount of SS169 in the cell membrane or outside the cells, specifically, (a) a compound that enhances a cell stimulation activity mediated by a ligand-receptor interaction (for example, activities that promote or suppress arachidonic acid release, acetylcholine release, intracellular $Ca^{2+}$ release, intracellular cAMP production, intracellular cGMP production, inositolphosphate production, cell membrane potential changes, intracellular protein phosphorylation, c-fos activation, pH reduction and the like, and the like) by increasing the amount of SS169 in the cell membrane or outside the cells, or (b) a compound that weakens the cell stimulation activity by reducing the amount of SS169 in the cell membrane or outside the cells.

As the compound used, peptides, proteins, non-peptide compounds, synthetic compounds, fermentation products and the like can be mentioned; these compounds may be novel compounds or known compounds.

A compound that enhances the cell stimulation activity is useful as a safe and less toxic pharmaceutical for enhancing a physiological activity of SS169.

A compound that weakens the cell stimulation activity is useful as a safe and less toxic pharmaceutical for reducing a physiological activity of SS169.

When a compound obtained using the above-described screening method or a salt thereof is used as a pharmaceutical, it can be formulated in the same manner as with the aforementioned "prophylactic/therapeutic agent for a disease associated with SS169 dysfunction".

Because the preparation thus obtained is safe and less toxic, it can be administered to, for example, mammals (for example, humans, rats, rabbits, sheep, swine, cattle, cats, dogs, monkeys and the like).

The dose of the compound or a salt thereof varies depending on the subject of administration, target organ, symptoms, method of administration and the like; in oral administration, the dose is normally about 0.1 to 100 mg, preferably about 1.0 to 50 mg, and more preferably about 1.0 to 20 mg, per day, in, for example, a patient with a sugar/lipid metabolic abnormality (assuming a 60 kg body weight). In parenteral administration, the single dose varies depending on the subject of administration, target organ, symptoms, method of administration and the like; for example, in the form of an injection, the dose is normally about 0.01 to 30 mg, preferably about 0.1 to 20 mg, and more preferably about 0.1 to 10 mg, per day, in, for example, a patient with a sugar/lipid metabolic abnormality (assuming a 60 kg body weight). In cases where the subject of administration is other than a human, a dose corresponding to a human dose per 60 kg body weight can be administered.

(12) Prophylactic/Therapeutic Agents for Various Diseases Comprising a Compound that Changes the Amount of SS169 in the Cell Membrane or Outside the Cells As stated above, SS169 is expressed nearly specifically in skeletal muscles and highly expressed in diabetic model mice and during re-feeding after fasting; for these and other reasons, SS169 is considered to play an important role in the regulation of differentiation of skeletal muscle cell and/or metabolism (particularly sugar/lipid metabolism). Therefore, a compound that changes the amount of SS169 in the cell membrane or outside the cells can be used as a prophylactic/therapeutic agent for a disease involved in differentiation of skeletal muscle cell and/or metabolic abnormality (hypofunction or hyperfunction) (for example, obesity, diabetes mellitus, impaired glucose tolerance, arteriosclerosis, hypertension, hyperlipemia and the like).

When the compound is used as a prophylactic/therapeutic agent for a disease associated with SS169 hypofunction or hyperfunction, it can be formulated in the same manner as with the aforementioned "prophylactic/therapeutic agent for a disease associated with SS169 dysfunction"

Because the preparation thus obtained is safe and less toxic, it can be administered to, for example, mammals (for example, humans, rats, rabbits, sheep, swine, cattle, cats, dogs, monkeys and the like).

The dose of the compound or a salt thereof varies depending on the subject of administration, target organ, symptoms, method of administration and the like; in oral administration, the dose is normally about 0.1 to 100 mg, preferably about 1.0 to 50 mg, and more preferably about 1.0 to 20 mg, per day, in, for example, a patient with a sugar/lipid metabolic abnormality (assuming a 60 kg body weight). In parenteral administration, the single dose varies depending on the subject of administration, target organ, symptoms, method of administration and the like; for example, in the form of an injection, the dose is normally about 0.01 to 30 mg, preferably about 0.1 to 20 mg, and more preferably about 0.1 to 10 mg, per day, in, for example, a patient with a sugar/lipid metabolic abnormality (assuming a 60 kg body weight). In cases where the subject of administration is other than a human, a dose corresponding to a human dose per 60 kg body weight can be administered.

As used herein, the term "regulator" of SS169 comprehensively means compounds capable of regulating (promoting or suppressing) any of the expression of SS169 (including transcription, translation, post-translational modification and the like), amounts (including membrane/extracellular transportation, stability and the like), and activities (including receptor- (or ligand)-binding activity, signal transmission activity and the like). Accordingly, for example, the above-described compound that changes the expression amount of SS169, SS169, a compound having specific affinity for SS169 (agonist, antagonist and the like), a compound that changes the amount of SS169 in the cell membrane or outside the cells and the like can be mentioned as the SS169 regulator. Each of these compounds can be obtained by performing the above-described screening method.

An SS169 regulator can be used as a prophylactic/therapeutic agent for a disease involved in differentiation of skeletal muscle cell and/or metabolic abnormality (particularly sugar/lipid metabolic abnormality). Hence, an SS169 regulator can be formulated and administered as described above with respect to prophylactic/therapeutic agents for various diseases containing a compound that changes the expression amount of SS169, prophylactic/therapeutic agents for various diseases containing SS169 and a compound having specific affinity for SS169 (agonist, antagonist and the like), and prophylactic/therapeutic agents for various diseases containing a compound that changes the amount of SS169 in the cell membrane or outside the cells.

(13) Preparation of Non-Human Transgenic Animal Bearing a DNA Encoding SS169

The present invention provides a non-human mammal bearing a DNA encoding exogenous SS169 (hereinafter abbreviated as the exogenous DNA of the present invention) or a variant DNA thereof (sometimes abbreviated as the exogenous variant DNA of the present invention).

Accordingly, the present invention provides:

[1] a non-human mammal bearing the exogenous DNA of the present invention or a variant DNA thereof,

[2] the animal described in term [1], wherein the non-human mammal is a rodent,

[3] the animal described in term [2], wherein the rodent is a mouse or a rat, and

[4] a recombination vector comprising the exogenous DNA of the present invention or a variant DNA thereof, and expressible in a mammal.

A non-human mammal bearing the exogenous DNA of the present invention or a variant DNA thereof (hereinafter abbreviated as the DNA-transfected animal of the present invention) can be prepared by transferring a desired DNA into an unfertilized egg, a fertilized egg, a spermatozoon, a germinal cell (including its precursor cell) or the like, preferably in the embryogenic stage in the development of the non-human mammal (more preferably in the single-cell or fertilized-egg stage and generally before the 8-cell phase), by the calcium phosphate method, the electric pulse method, the lipofection method, the aggregation method, the microinjection method, the particle gun method, the DEAE-dextran method or the like. Also, it is possible to transfer the exogenous DNA of the present invention into a somatic cell, a living organ, a tissue cell or the like by the DNA transfer method, and utilize them for cell culture, tissue culture and the like, and these cells may be fused with the above-described germinal cells by a method of cell fusion known per se to create the DNA transgenic animal of the present invention.

As examples of the non-human mammal used, cattle, swine, sheep, goat, rabbits, dogs, cats, guinea pigs, hamsters, mice, rats and the like can be mentioned. In particular, preferred from the viewpoint of creating a pathologic animal model system are rodents, especially mice (for example, C57BL/6 line, DBA2 line and the like, which are pure lines, B6C3F$_1$ line, BDF$_1$ line, B6D2F$_1$ line, BALB/c line, ICR line and the like, which are cross lines) or rats (for example, Wistar, SD and the like), since they have relatively short ontogeny and lifecycles and are easy to breed.

As "the mammal" in a recombination vector expressible in a mammal, humans and the like can be mentioned, in addition to the above-described non-human mammals.

The exogenous DNA of the present invention refers to the DNA of the present invention once isolated/extracted from a mammal, rather than the DNA of the present invention inherently possessed by a non-human mammal.

As the variant DNA of the present invention, those resulting from a variation (for example, mutations and the like) in the base sequence of the original DNA of the present invention, specifically DNAs having a base addition, deletion, substitution with another base or the like, and the like can be mentioned, and abnormal DNAs are included.

The abnormal DNA means a DNA that allows the expression of abnormal SS169, and is exemplified by a DNA that allows the expression of a protein that suppresses the function of normal SS169, and the like.

The exogenous DNA of the present invention may be derived from a mammal of any of the same species as, or a different species from, the subject animal. In transferring the DNA of the present invention into the subject animal, it is generally advantageous to use the DNA of the present invention as a DNA construct having the DNA bound downstream of a promoter capable of allowing the expression of the DNA in animal cells. For example, when the human DNA of the present invention is transferred, a DNA-transfected mammal that highly expresses the DNA of the present invention can be prepared by microinjecting a DNA construct (e.g., vector and the like) having the human DNA of the present invention ligated downstream of various promoters allowing the expression of a DNA derived from various mammals (for example, rabbits, dogs, cats, guinea pigs, hamsters, rats, mice and the like) bearing the DNA of the present invention, which is highly homologous to the human DNA, into a fertilized egg of the subject mammal, for example, a mouse fertilized egg.

As the expression vector for carrying the DNA of the present invention, *Escherichia coli*-derived plasmids, *Bacillus subtilis*-derived plasmids, yeast-derived plasmids, bacteriophages such as λ phage, retroviruses such as Moloney leukemia virus, animal viruses such as vaccinia virus and baculovirus, and the like can be used. In particular, *Escherichia coli*-derived plasmids, *Bacillus subtilis*-derived plasmids, yeast-derived plasmids and the like are preferably used.

As examples of the promoter that regulates the DNA expression, 1) promoters of DNA derived from viruses (e.g., simian virus, cytomegalovirus, Moloney mouse leukemia virus, JC virus, breast cancer virus, poliovirus and the like) and 2) promoters derived from various mammals (humans, rabbits, dogs, cats, guinea pigs, hamsters, rats, mice and the like), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase β I subunit, dystrophin, tartrate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase 1 tissue inhibitor, MHC class I antigen (H-2L), H-ras, renin, dopamine β-hydroxylase, thyroid peroxidase (TPO), peptide chain elongation factor 1α (EF-1α), β actin, α and β myosin heavy chains, myosin light chains 1 and 2, myelin basic protein, thyroglobulin, Thy-1, immunoglobulins, H-chain variable region (VNP), serum amyloid P component, myoglobin, troponin C, smooth muscle a actin, preproencephalin A, vasopressin and the like can be used. Among them, the cytomegalovirus promoter, the human protein elongation factor 1α (EF-1α) promoter, the human and chicken β actin promoters and the like, which enable high expression in the whole body, are preferred.

The above-described vector preferably has a sequence that terminates the transcription of desired messenger RNA in the DNA-transfected animal (generally referred to as a terminator); for example, sequences of DNAs derived from viruses or various mammals can be used, with preference given to the simian virus SV40 terminator and the like.

In addition, for the purpose of increasing the expression of the desired exogenous DNA, the splicing signal and enhancer region of each DNA, a portion of the intron of an eukaryotic DNA and the like may also be joined upstream of the 5' end of the promoter region, between the promoter region and the translational region, or downstream of the 3' end of the translational region, depending on the purpose of use.

The translational region of normal SS169 can be acquired as the whole genomic DNA or a portion thereof from DNAs derived from the liver, kidney, adipose tissue, or muscle of various mammals (for example, humans, rabbits, dogs, cats, guinea pigs, hamsters, rats, mice and the like) and from various commercially available genomic DNA libraries, or using as the source material a cDNA prepared by a known method from RNA derived from the aforementioned organs or tissues. Also, an exogenous abnormal DNA can be obtained by mutating the translational region of normal SS169 obtained from the above-described cells or tissues by point mutagenesis.

The translational region can be prepared as a DNA construct expressible in the transgenic animal by an ordinary DNA engineering technique wherein the DNA is joined downstream of the aforementioned promoter (and, if desired, upstream of the transcription termination site).

The exogenous DNA of the present invention at the fertilized egg cell stage is transferred in a manner such that the DNA is certainly present in all the germinal cells and somatic cells of the subject mammal. The presence of the exogenous DNA of the present invention in the germinal cells of the animal prepared by DNA transfer means that all offspring of the animal prepared will carry the exogenous DNA of the present invention in all of the germinal cells and somatic cells thereof. The offspring of the animal of this species that have inherited the exogenous DNA of the present invention have the exogenous DNA of the present invention in all of the germinal cells and somatic cells thereof.

A non-human mammal transfected with the normal exogenous DNA of the present invention can be grown over generations as animals bearing that DNA in an ordinary breeding environment after being confirmed to stably retain the exogenous DNA by mating.

The exogenous DNA of the present invention at the fertilized egg cell stage is transferred in a manner such that the DNA is present in excess in all of the germinal cells and somatic cells of the subject mammal. The presence of the exogenous DNA of the present invention in excess in the germinal cells of the animal prepared by DNA transfer means that all offspring of the animal prepared will carry the exogenous DNA of the present invention in excess in all of the germinal cells and somatic cells thereof. The offspring of the animal of this species that have inherited the exogenous DNA of the present invention have the exogenous DNA of the present invention in excess in all of the germinal cells and somatic cells thereof.

By obtaining a homozygous animal having the transferred DNA in both the homologous chromosomes, and mating a male and female of this animal, the animal can be grown over generations so that all offspring thereof will retain the DNA in excess.

A non-human mammal having the normal DNA of the present invention highly expresses the normal DNA of the invention; the normal DNA may eventually cause SS169 hyperfunction by enhancing the function of the endogenous normal DNA, and the animal can be used as a pathologic model animal for the disease. For example, using an animal transfected with the normal DNA of the present invention, it is possible to elucidate the pathological mechanisms of SS169 hyperfunction and diseases associated with SS169, and to investigate therapeutic methods for these diseases.

Also, because a mammal transfected with the exogenous normal DNA of the present invention has a symptom of increased free SS169, it can be used for screening tests for therapeutic drugs for diseases associated with SS169.

On the other hand, a non-human mammal bearing the exogenous abnormal DNA of the present invention can be grown over generations as an animal bearing the DNA in an ordinary breeding environment after being confirmed to stably retain the exogenous DNA by mating. Furthermore, the desired exogenous DNA can be used as the source material as incorporated in the aforementioned plasmid. A DNA construct with a promoter can be prepared by an ordinary DNA engineering technique. The abnormal DNA of the present invention at the fertilized egg cell stage is transferred in a manner such that the DNA is present in all of the germinal cells and somatic cells of the subject mammal. The presence of the abnormal DNA of the present invention in the germinal cells of the animal prepared by DNA transfer means that all offspring of the animal prepared will carry the abnormal DNA of the present invention in all of the germinal cells and somatic cells thereof. The offspring of the animal of this species that have inherited the exogenous DNA of the present invention have the abnormal DNA of the present invention in all of the germinal cells and somatic cells thereof. By obtaining a homozygous animal having the introduced DNA in both the homologous chromosomes, and mating a male and female of this animal, the animal can be grown over generations so that all the offspring thereof will carry the DNA.

A non-human mammal bearing the abnormal DNA of the present invention highly expresses the abnormal DNA of the present invention; the DNA may finally cause functionally inactive adiaphoria to SS169 by inhibiting the function of endogenous normal DNA, and the animal can be utilized as a pathological model animal for the disease. For example, using an animal transfected with the abnormal DNA of the present invention, it is possible to elucidate the pathological mechanism of functionally inactive adiaphoria to SS169, and to investigate a therapeutic method for this disease.

Regarding specific applicability, an animal highly expressing the abnormal DNA of the present invention serves as a model for elucidating the functional impairment (dominant negative action) of normal SS169 due to abnormal SS169 in functionally inactive adiaphoria to SS169.

Because a mammal transfected with the exogenous abnormal DNA of the present invention has a symptom of increased free abnormal SS169, it can also be utilized for screening tests for a therapeutic drug for functionally inactive adiaphoria to SS169.

As examples of other potential applications of the above-described two kinds of DNA-transfected animal of the present invention, the following can be mentioned:

(1) use as cell sources for tissue culture,
(2) analysis of association with proteins specifically expressed or activated by SS169 and the like, by a direct analysis of DNA or RNA in a tissue of the DNA-transfected animal of the present invention, or by an analysis of the SS169 produced,
(3) research into the functions of cells generally difficult-to-culture tissues using cells of DNA-bearing tissues cultured by standard tissue culture technology,
(4) screening of a drug that enhances a function of cells using the cells described in (3) above,
(5) isolation and purification of variant SS169 and preparation of its antibody, and the like.

Furthermore, using the DNA-transfected animal of the present invention, it is possible to examine the clinical symptoms in diseases associated with SS169, including functionally inactive adiaphoria to SS169 and the like, and it is also possible to obtain more extensive pathological findings in various organs of a model of a disease associated with SS169, thus contributing to the development of new therapeutic methods, and to research and treatment for secondary diseases due to the disease.

It is also possible to excise each organ from the DNA-transfected animal of the present invention, shred the organ, then acquire liberated DNA-transfected cells using a protein-degrading enzyme such as trypsin, and culture the cells or establish a line of the cultured cells. Furthermore, it is possible to examine the associations with identification, apoptosis, differentiation or growth of SS169-producing cells, or the signal transmission mechanisms involved therein, to examine abnormalities thereof, and the like, thus providing effective research materials for the elucidation of the action of SS169.

Furthermore, for the development of therapeutic drugs for diseases associated with SS169, including functionally inactive adiaphoria to SS169, using the DNA-transfected animal of the present invention, it is possible to provide an effective and rapid screening method for the therapeutic drugs for the diseases, using the above-described test method, quantification method and the like. Also, using the DNA-transfected animal of the present invention or the exogenous DNA expression vector of the present invention, it is possible to investigate and develop a DNA therapy for a disease associated with SS169.

(14) Preparation of Non-Human Knockout Animal Having the SS169-Encoding Gene Inactivated Therein The present invention provides non-human mammalian embryonic stem cells having the DNA of the present invention inactivated therein and a non-human mammal deficient in the expression of the DNA of the present invention.

Accordingly, the present invention provides:
[1] non-human mammalian embryonic stem cells having the DNA of the present invention inactivated therein,
[2] the embryonic stem cells described in term [1], wherein the DNA has been inactivated by introducing a reporter gene (e.g., the β-galactosidase gene derived from *Escherichia coli*),
[3] the embryonic stem cells described in term [1], which is resistant to neomycin,
[4] the embryonic stem cells described in term [1], wherein the non-human mammal is a rodent,
[5] the embryonic stem cells described in term [4], wherein the rodent is a mouse,
[6] a non-human mammal deficient in the expression of the DNA of the present invention, wherein the DNA has been inactivated,
[7] the non-human mammal described in term [6], wherein the DNA has been inactivated by introducing a reporter gene (e.g., the β-galactosidase gene derived from *Escherichia coli*), the reporter gene being expressible under the control of a promoter for the DNA of the present invention,
[8] the non-human mammal described in term [6], wherein the non-human mammal is a rodent,
[9] the non-human mammal described in term [8], wherein the rodent is a mouse, and
[10] a method of screening a compound that promotes or inhibits the promoter activity for the DNA of the present invention or a salt thereof, which comprises administering a test compound to the animal described in term [7], and detecting the expression of the reporter gene.

Non-human mammalian embryonic stem cells having the DNA of the present invention inactivated therein refer to embryonic stem cells (hereinafter abbreviated as ES cells) of a non-human mammal, wherein the DNA has substantially no capability of SS169 expression (hereinafter also referred to as the knockout DNA of the present invention) as a result of artificially mutating the DNA of the present invention possessed by the non-human mammal to suppress the capability of DNA expression, or to substantially deprive of the activity of the SS169 encoded by the DNA.

The non-human mammal is exemplified by the same examples as those mentioned above.

The method of artificially mutating the DNA of the present invention can be performed by, for example, deleting a portion or whole of the DNA sequence, or inserting, or replacing with, another DNA, by a gene engineering technique. For example, by shifting the reading frame of codon or destroying the function of promoter or exon with these mutations, the knockout DNA of the present invention may be prepared.

Specifically, non-human mammalian embryonic stem cells having the DNA of the present invention inactivated therein (hereinafter abbreviated as the DNA-inactivated ES cells of the present invention or the knockout ES cells of the present invention) can be obtained by isolating the DNA of the present invention existing in the desired non-human mammal; constructing a DNA strand having a DNA sequence to destroy the gene by inserting a drug resistance gene represented by the neomycin resistance gene and the hygromycin resistance gene, or a reporter gene represented by lacZ (β-galactosidase gene) and cat (chloramphenicol acetyltransferase gene) or the like into the exon moiety of the DNA of the present invention to destroy the exon function, or inserting a DNA sequence that terminates gene transcription (for example, poly A addition signal and the like) into the intron moiety between exons to prevent the synthesis of complete mRNA; transferring the DNA strand into a chromosome of the animal by, for example, homologous recombination; analyzing the thus-obtained ES cells by a Southern hybridization analysis using a DNA sequence on the DNA of the present invention or in the vicinity thereof as a probe, or by a PCR method using a DNA sequence on the targeting vector and a DNA sequence in the vicinity other than the DNA of the present invention used to prepare the targeting vector, as primers; and selecting the knockout ES cells of the present invention.

The starting ES cell to have the DNA of the present invention inactivated therein by homologous recombination and the like may be of an already established cell line as described above, or of a cell line newly established by the known method of Evans and Kaufman. For example, in the case of mouse ES cells, an ES cell of the 129 line is currently generally used as the starting cell; however, since the immunological background of the 129 line is unclear, an ES cell line established using, for example, C57BL/6 mice, or $BDF_1$ mice ($F_1$ between C57BL/6 and DBA/2), which have been improved by crossing with DBA/2 to increase the otherwise small number of collectable eggs of C57BL/6, and the like can, also be used advantageously, for the purpose of obtaining a pure line of ES cells of clear immunological genetic background, and the like. Because $BDF_1$ mice are backgrounded by C57BL/6 mice, in addition to being advantageous in that the number of collectable eggs is large and the eggs are tough, the ES cells obtained using a $BDF_1$ mouse, when used to create a pathological model mouse, can be used advantageously in that the genetic background thereof can be replaced with C57BL/6 mouse by back-crossing with C57BL/6 mouse.

For establishing a line of ES cells, blastocysts at day 3.5 after fertilization are normally used; in addition, by collecting 8-cell embryos and culturing them to the blastocyst stage, a large number of early embryos can be obtained efficiently.

Although the ES cells used may be of either sex, male ES cells are normally more convenient in creating a germ line chimera. Also, to reduce operating time for painstaking cultivation, it is desirable to make sex identification as early as possible.

As an example of the method of sex identification of ES cells, a method that comprises amplifying and detecting a gene in the sex-determining region on Y chromosome by a PCR method can be mentioned. Using this method, a number of ES cells in one colony (about 50 cells) is enough for karyotype analysis, compared to the conventional method, which requires about $10^6$ cells for the same purpose; therefore, it is possible to perform primary selection of ES cells in the early stage of cultivation by sex identification, thus enabling a significant reduction in operating time in the early stage of cultivation because early selection of male cells has become possible.

Secondary selection can be performed by, for example, confirming the chromosome number by the G-binding method, and the like. Although the chromosome number of the ES cells obtained is desirably 100% of the normal number, it is desirable that a gene of the ES cells is knocked out and then re-cloned into normal cells (for example, cells having a chromosome number of 2n=40 for mice) if a 100% number is difficult to achieve due to physical procedures during cell line establishment, and the like.

Although the embryonic stem cell line thus obtained generally shows very good growing capacity, it is likely to lose its capability of ontogeny, so that it must be subcultured carefully. For example, cells of this line are cultured using a method of cultivation on appropriate feeder cells such as STO fibroblasts in the presence of LIF (1 to 10000 U/ml) in a carbon dioxide incubator (preferably under 5% carbon dioxide and 95% air or under 5% oxygen, 5% carbon dioxide and 90% air) at about 37° C., or the like; they are subcultured using, for example, a method comprising a treatment with a trypsin/EDTA solution (normally 0.001% to 0.5% trypsin/0.1 to 5 mM EDTA, preferably about 0.1% trypsin/1 mM EDTA) to give single cells, and sowing them on newly prepared feeder cells, or the like. This subculture is normally performed every 1 to 3 days, during which it is desirable that the cells be examined, and any morphologically abnormal cells, if found, are desirably discarded.

ES cells can be differentiated into various types of cells, such as the parietal muscle, visceral muscles, and myocardium when subjected to monolayer culture to the extent of a high density, or to suspension culture to the extent of the formation of a cell mass, under appropriate conditions [M. J. Evans and M. H. Kaufman, Nature, Vol. 292, p. 154, 1981; G. R. Martin, Proceedings of the National Academy of Sciences of the USA (Proc. Natl. Acad. Sci. U.S.A.), Vol. 78, p. 7634, 1981; T. C. Doetschman et al., Journal of Embryology and Experimental Morphology (J. Embryol. Exp. Morphol.), Vol. 87, p. 27, 1985], and cells deficient in the expression of the DNA of the present invention obtained by differentiating the ES cells of the present invention are useful in cytobiological investigations of SS169 or SS169.

A non-human mammal deficient in the expression of the DNA of the present invention can be distinguished from a normal animal by measuring the amounts of mRNA in the animals, and indirectly comparing the expression amounts thereof.

The non-human mammal is exemplified by the same examples as those mentioned above.

A non-human mammal deficient in the expression of the DNA of the present invention can be produced by, for example, introducing a targeting vector prepared as described above into a mouse embryonic stem cell or mouse ovum to cause homologous recombination to replace the DNA sequence having the DNA of the present invention inactivated therein in the introduced targeting vector with the DNA of the present invention on a chromosome of the mouse embryonic stem cell or mouse ovum, whereby the DNA of the present invention can be knocked out. Since many recombinations in mammals are non-homologous, as examples of means of screening cells having undergone homologous recombination, a method that comprises inserting a drug resistance gene such as the neomycin resistance gene into the DNA of the present invention, constructing a targeting vector comprising the thymidine kinase (tk) gene in the vicinity of the DNA of the present invention, introducing the vector into an embryonic stem cell or ovum, and selecting cells that survive in the presence of a drug corresponding to the inserted drug resistance gene (for example, G418 and the like for the neomycin resistance gene) and ganciclovir, can be mentioned. That is, if the insertion variant DNA of the present invention is incorporated onto a chromosome by homologous recombination, the cells are resistant to ganciclovir because the tk gene is eliminated, whereas in the case of incorporation by non-homologous recombination, the cells are susceptible to ganciclovir because the tk gene is incorporated at the same time. If the diphtheria toxin gene or the like is used instead of the tk gene, cells undergoing random insertion will die due to the production of the toxin, so that selection with a single drug is possible.

The final confirmation of cells having the DNA of the present invention knocked out therein can be achieved by a Southern hybridization analysis using a DNA sequence on the DNA of the present invention or in the vicinity thereof as a probe, or by a PCR method using a DNA sequence on the targeting vector and a DNA sequence in the vicinity other than the mouse-derived DNA of the present invention used in the targeting vector, as primers.

When a non-human mammalian embryonic stem cell is used, a cell line having the DNA of the present invention inactivated therein by homologous gene recombination is cloned, its cell is injected into a non-human mammalian embryo or blastocyst at an appropriate stage, for example, the 8-cell stage, and the chimeric embryo prepared is transplanted into the uterus of a pseudopregnant female of the non-human mammal. The animal created is a chimeric animal consisting of both cells having the normal locus of the DNA of present invention and cells having an artificially mutated locus of the DNA of the present invention.

When some of the germ cells of the chimeric animal have a mutated locus of the DNA of the present invention, such a chimeric individual and a normal individual may be mated; from the animal population thus obtained, an individual all of whose tissues consist of cells having an artificially mutated locus of the DNA of the present invention can be selected by, for example, coat color judgment and the like. Because the individual thus obtained is normally a hetero-expression-deficient individual, such hetero-expression-deficient individuals may be mated to obtain an individual homo-deficient in the expression of the protein of the present invention out of the pups thereof.

When an ovum is used, for example, a transgenic non-human mammal incorporating a targeting vector in a chromosome can be obtained by injecting a DNA solution into the nucleus of the ovum by the microinjection method, and such an individual is obtained by selecting one having a mutation in the locus of the DNA of the present invention by homologous gene recombination from among these transgenic non-human mammals.

An individual having the DNA of the present invention thus knocked out therein can also be grown over generations in an ordinary breeding environment after animal individuals obtained by mating as well are confirmed to have the DNA knocked out therein.

Furthermore, establishment and maintenance of a germ line can be performed according to conventional methods. That is, homozygous animals having the inactivated DNA in both the homologous chromosomes can be obtained by mating a male and female animal bearing the inactivated DNA. These homozygous animals can be efficiently propagated by breeding in a ratio of one normal individual and a plurality of homozygous animals relative to the dam. By mating a male and female heterozygous animal, homozygous and heterozygous animals having the inactivated DNA are propagated over generations.

Non-human mammalian embryonic stem cells having the DNA of the present invention inactivated therein are highly useful in creating a non-human mammal deficient in the expression of the DNA of the present invention.

Also, because a non-human mammal deficient in the expression of the DNA of the present invention lacks various biological activities induced by SS169, it can serve as models of diseases caused by inactivation of biological activities of SS169, and is hence useful in elucidating the causes of these diseases and investigating therapies therefor.

(14a) Method of Screening a Compound Having a Therapeutic/Prophylactic Effect for a Disease Caused by Deficiency, Damage and the Like of the DNA of the Present Invention.

A non-human mammal deficient in the expression of the DNA of the present invention can be used to screen a compound having a therapeutic/prophylactic effect for a disease caused by deficiency, damage and the like of the DNA of the present invention.

Accordingly, the present invention provides a method of screening a compound having a therapeutic/prophylactic effect for a disease caused by deficiency, damage and the like of the DNA of the present invention or a salt thereof, which comprises administering a test compound to a non-human mammal deficient in the expression of the DNA of the present invention, and observing and measuring changes in the animal.

As the non-human mammal deficient in the expression of the DNA of the present invention used for the screening method, the same examples as those mentioned above can be mentioned.

As examples of the test compound used, peptides, proteins, non-peptide compounds, synthetic compounds, fermentation products, cell extracts, plant extracts, animal tissue extracts, plasma and the like can be mentioned; these compounds may be novel compounds or known compounds.

Specifically, the therapeutic/prophylactic effect of a test compound can be tested by treating a non-human mammal deficient in the expression of the DNA of the present invention with the test compound, comparing the animal with a non-treated control animal, with the changes in the organs, tissues, disease symptoms and the like in the animals as indexes.

Examples of the method of treating a test animal with a test compound include oral administration, intravenous injection and the like, which can be selected as appropriate for the symptoms of the test animal, the properties of the test compound, and the like. A dose of the test compound can be selected as appropriate according to the method of administration, properties of the test compound and the like.

When a test compound is administered to a test animal in the screening method, the test compound can be selected as a compound having a therapeutic/prophylactic effect for the above-described disease, if the blood glucose level in the test animal decreases by about 10% or more, preferably about 30% or more, and more preferably about 50% or more.

A compound obtained using the screening method is a compound selected from among the above-described test compounds, and can be used as a safe and less toxic pharmaceutical such as a therapeutic/prophylactic agent for a disease caused by SS169 deficiency, damage and the like, for example, diseases involved in differentiation of skeletal muscle cell and/or metabolic abnormality (e.g., obesity, diabetes mellitus, impaired glucose tolerance, arteriosclerosis, hypertension, hyperlipemia and the like). Furthermore, compounds derived from a compound obtained by the above-described screening can also be used in the same manner.

A compound obtained by the screening method may have formed a salt; as examples of the salt of the compound, physiologically acceptable salts with acids (e.g., inorganic acids, organic acids and the like), bases (e.g., alkali metals and the like) and the like can be mentioned, with preference given to physiologically acceptable acid adduct salts. As examples of such salts, salts with inorganic acids (for example, hydrochloric acid, phosphoric acid, hydrobromic acid, sulfuric acid and the like), salts with organic acids (for example, acetic acid, formic acid, propionic acid, fumaric acid, maleic acid, succinic acid, tartaric acid, citric acid, malic acid, oxalic acid, benzoic acid, methanesulfonic acid, benzenesulfonic acid and the like) and the like can be mentioned.

When a compound obtained by the screening method or a salt thereof is used as a pharmaceutical, it can be formulated in the same manner as with the aforementioned "prophylactic/therapeutic agent for a disease associated with SS169 dysfunction".

Because the preparation thus obtained is safe and less toxic, it can be administered to, for example, mammals (for example, humans, rats, mice, guinea pigs, rabbits, sheep, swine, cattle, horses, cats, dogs, monkeys and the like).

The dose of the compound or a salt thereof varies depending on target disease, subject of administration, route of administration and the like; in oral administration, for example, the dose is normally about 0.1 to 100 mg, preferably about 1.0 to 50 mg, and more preferably about 1.0 to 20 mg, per day, in, for example, a patient with a sugar/lipid metabolic abnormality (assuming a 60 kg body weight). In parenteral administration, the single dose varies depending on the subject of administration, target organ, symptoms, method of administration and the like; for example, in the form of an injection, the dose is normally about 0.01 to 30 mg, preferably about 0.1 to 20 mg, and more preferably about 0.1 to 10 mg, per day, in, for example, a patient with a sugar/lipid metabolic abnormality (assuming a 60 kg body weight). In cases where the subject of administration is other than a human, a dose corresponding to a human dose per 60 kg body weight can be administered.

(14b) Method of Screening a Compound that Promotes or Inhibits the Activity of a Promoter for the DNA of the Present Invention The present invention provides a method of screening a compound that promotes or inhibits the activity of a promoter for the DNA of the present invention or a salt thereof, which comprises administering a test compound to a non-human mammal deficient in the expression of the DNA of the present invention, and detecting the expression of a reporter gene.

In the above-described screening method, as the non-human mammal deficient in the expression of the DNA of the present invention, one having the DNA of the present invention inactivated therein by introducing a reporter gene, wherein the reporter gene is expressible under the control of a promoter for the DNA of the present invention, out of the aforementioned non-human mammals deficient in the expression of the DNA of the present invention, is used.

The test compound is exemplified by the same examples as those mentioned above.

As the reporter gene used, the same examples as those mentioned above can be mentioned, with preference given to the β-galactosidase gene (lacZ), the soluble alkaline phosphatase gene or the luciferase gene and the like.

In a non-human mammal deficient in the expression of the DNA of the present invention having the DNA of the present invention replaced with a reporter gene therein, the reporter gene occurs under the control of a promoter for the DNA of the present invention; therefore, promoter activity can be detected by tracing the expression of a substance encoded by the reporter gene.

For example, when a portion of the SS169-encoding DNA region is replaced with the β-galactosidase gene (lacZ) derived from *Escherichia coli*, β-galactosidase is expressed, in place of SS169, in tissues where SS169 is otherwise expressed. Therefore, for example, by staining using a reagent that serves as a substrate for β-galactosidase, such as 5-bromo-4-chloro-3-indolyl-β-galactopyranoside (X-gal), the expression state of SS169 in the animal body can be examined conveniently. Specifically, an SS169-deficient mouse or a tissue section thereof is fixed with glutaraldehyde and the like, washed with phosphate-buffered saline (PBS), then reacted with a staining solution containing X-gal at room temperature or around 37° C. for about 30 minutes to 1 hour, thereafter the tissue specimen is washed with 1 mM EDTA/PBS solution to stop the β-galactosidase reaction, and the color developed is examined. The lacZ-encoding mRNA may be detected according to a conventional method.

A compound obtained using the above-described screening method or a salt thereof is a compound selected from among the above-described test compounds, and promoting or inhibiting the activity of a promoter for the DNA of the present invention.

A compound obtained by the screening method may have formed a salt; as examples of the salt of the compound, physiologically acceptable salts with acids (e.g., inorganic acids and the like), bases (e.g., organic acids and the like) and the like can be mentioned, with preference given to physiologically acceptable acid adduct salts. As examples of such salts, salts with inorganic acids (for example, hydrochloric acid, phosphoric acid, hydrobromic acid, sulfuric acid and the like), salts with organic acids (for example, acetic acid, formic acid, propionic acid, fumaric acid, maleic acid, succinic acid, tartaric acid, citric acid, malic acid, oxalic acid, benzoic acid, methanesulfonic acid, benzenesulfonic acid and the like) and the like can be mentioned.

Because a compound that promotes the activity of a promoter for the DNA of the present invention or a salt thereof is capable of promoting the expression of SS169 and promoting the function of SS169, it is useful as, for example, a pharmaceutical such as a prophylactic/therapeutic drug for a disease associated with SS169 dysfunction and the like.

Because a compound that inhibits the activity of a promoter for the DNA of the present invention or a salt thereof is capable of inhibiting the expression of SS169 and inhibiting the function of SS169, it is useful as, for example, a pharmaceutical such as a prophylactic/therapeutic drug for a disease associated with SS169 overexpression and the like.

As examples of the disease associated with SS169 dysfunction or overexpression, diseases involved in differentiation of skeletal muscle cell and/or metabolic abnormality (for example, obesity, diabetes mellitus, impaired glucose tolerance, arteriosclerosis, hypertension, hyperlipemia and the like) and the like can be mentioned.

Furthermore, compounds derived from a compound obtained by the above-described screening can also be used in the same manner.

When a compound obtained by the screening method or a salt thereof is used as a pharmaceutical, it can be formulated in the same manner as with the aforementioned "prophylactic/therapeutic agent for a disease associated with SS169 dysfunction".

Because the preparation thus obtained is safe and less toxic, it can be administered to, for example, mammals (for example, humans, rats, mice, guinea pigs, rabbits, sheep, swine, cattle, horses, cats, dogs, monkeys and the like).

The dose of the compound or a salt thereof varies depending on the subject of administration, target organ, symptoms, route of administration and the like; in oral administration of a compound that promotes or inhibits promoter activity, the dose is normally about 0.1 to 100 mg, preferably about 1.0 to 50 mg, and more preferably about 1.0 to 20 mg, per day, in, for example, a patient with a sugar/lipid metabolic abnormality (assuming a 60 kg body weight). In parenteral administration, the single dose varies depending on the subject of administration, target organ, symptoms, method of administration, and the like; for example, in the form of an injection, the dose is normally about 0.01 to 30 mg, preferably about 0.1 to 20 mg, and more preferably about 0.1 to 10 mg, per day, in, for example, a patient with a sugar/lipid metabolic abnormality (assuming a 60 kg body weight). In cases where the subject of administration is other than a human, a dose corresponding to a human dose per 60 kg body weight can be administered.

As stated above, a non-human mammal deficient in the expression of the DNA of the present invention is highly useful in screening a compound that promotes or inhibits the activity of a promoter for the DNA of the present invention or a salt thereof, and can contribute significantly to the elucidation of the causes of various diseases due to deficiency of the expression of the DNA of the present invention or the development of a prophylactic/therapeutic drug.

Also, provided that a gene encoding one of various proteins is joined downstream of a DNA comprising an SS169 promoter region, and this DNA construct is injected into an animal ovum to prepare what is called a transgenic animal, it is also possible to allow the animal to specifically synthesize the protein, and investigate its action in vivo. Furthermore, provided that an appropriate reporter gene is bound to the above-described promoter portion, and a cell line that expresses the gene is established, the cell line can be used as a screening system for a low-molecular compound that acts to specifically promote or suppress the in vivo productivity of SS169 itself.

Abbreviations for bases, amino acids and the like used in the present specification and drawings are based on abbreviations specified by the IUPAC-IUB Commission on Biochemical Nomenclature or abbreviations in common use in relevant fields. Some examples are given below. When an optical isomer may be present in amino acid, it is of the L-configuration, unless otherwise stated.

DNA: deoxyribonucleic acid
cDNA: complementary deoxyribonucleic acid
A: adenine
T: thymine
G: guanine
C: cytosine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate
Gly: glycine Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysine
Arg: arginine
His: histidine
Phe: phenylalanine
Tyr: tyrosine
Trp: tryptophan
Pro: proline
Asn: asparagine
Gln: glutamine
pGlu: pyrroglutamic acid
Me: methyl group
Et: ethyl group
Bu: butyl group
Ph: phenyl group
TC: thiazolidin-4(R)-carboxamide group Substituents, protecting groups and reagents often mentioned in the present specification are denoted by the symbols shown below.

Tos: p-toluenesulfonyl
CHO: formyl
Bzl: benzyl
Cl₂Bzl: 2,6-dichlorobenzyl
Bom: benzyloxymethyl
Z: benzyloxycarbonyl
Cl-Z: 2-chlorobenzyloxycarbonyl
Br-Z: 2-bromobenzyloxycarbonyl
Boc: t-butoxycarbonyl
DNP: dinitrophenol
Trt: trityl
Bum: t-butoxymethyl
Fmoc: N-9-fluorenylmethoxycarbonyl
HOBt: 1-hydroxybenzotriazole
HOOBt: 3,4-dihydro-3-hydroxy-4-oxo-1,2,3-benzotriazine
HONB: 1-hydroxy-5-norbornene-2,3-dicarboximide
DCC: N,N'-dicyclohexylcarbodiimide The sequence identification numbers in the sequence listing of the present specification show the following sequences.

[SEQ ID NO:1]
This represents the base sequence of the secretory or membrane protein SS169 gene derived from the human soleus.

[SEQ ID NO:2]
This represents the amino acid sequence encoded by the secretory or membrane protein SS169 gene derived from the human soleus.

[SEQ ID NO:3]
This represents the base sequence of the secretory or membrane protein SS169 gene derived from the mouse soleus.

[SEQ ID NO:4]
This represents the amino acid sequence encoded by the secretory or membrane protein SS169 gene derived from the mouse soleus.

[SEQ ID NO:5]
This represents the base sequence of a primer for amplifying a secretory or membrane protein SS169 cDNA fragment derived from the mouse soleus.

[SEQ ID NO:6]
This represents the base sequence of a primer for amplifying a secretory or membrane protein SS169 cDNA fragment derived from the mouse soleus.

[SEQ ID NO:7]
This represents the base sequence of a secretory or membrane protein SS169 cDNA fragment derived from the mouse soleus, obtained by the SST method.

[SEQ ID NO:8]
This represents the base sequence of a 5'-RACE primer used for cloning the mouse SS169 gene.

[SEQ ID NO:9]
This represents the base sequence of a 3'-RACE primer used for cloning the mouse SS169 gene.

[SEQ ID NO:10]
This represents a cDNA sequence of mouse SS169.

[SEQ ID NO:11]
This represents the base sequence of a 5'-RACE primer used for cloning the human SS169 gene.

[SEQ ID NO:12]
This represents the base sequence of a 3'-RACE primer used for cloning the human SS169 gene.

[SEQ ID NO:13]
This represents a cDNA sequence of the human SS169 gene.

[SEQ ID NO:14]
This represents the base sequence of a primer used to amplify a mouse SS169 cDNA fragment.

[SEQ ID NO:15]
This represents the base sequence of a primer used to amplify a mouse SS169 cDNA fragment.

[SEQ ID NO:16]
This represents the base sequence of a 3'-RACE primer used for cloning the rat SS169 gene.

[SEQ ID NO:17]
This represents the base sequence of a 3'-RACE primer used for cloning the rat SS169 gene.

[SEQ ID NO:18]
This represents the base sequence of a 3'-RACE primer used for cloning the rat SS169 gene.

[SEQ ID NO:19]
This represents the base sequence of a 3'-RACE primer used for cloning the rat SS169 gene.

[SEQ ID NO:20]
This represents the base sequence of a primer used to amplify a rat SS169 cDNA fragment (CDS).

[SEQ ID NO:21]
This represents the base sequence of a primer used to amplify a rat SS169 cDNA fragment (CDS).

[SEQ ID NO:22]
This represents the base sequence of the secretory or membrane protein SS169 gene derived from the rat gastrocnemius.

[SEQ ID NO:23]
This represents the amino acid sequence encoded by the secretory or membrane protein SS169 gene derived from the rat gastrocnemius.

[SEQ ID NO:24]
This represents the base sequence of a primer used to amplify a rat SS169 cDNA fragment.

[SEQ ID NO:25]
This represents the base sequence of a primer used to amplify a rat SS169 cDNA fragment.

The present invention is hereinafter described in more detail by means of the following Examples, which, however, are not to be construed as limiting the scope of the present invention. Gene manipulation procedures such as cloning and base sequencing were performed according to known methods (for example, methods described in Molecular Cloning, 2nd edition, J. Sambrook et al., Cold Spring Harbor Lab. Press (1989) and the like).

EXAMPLE 1

Screening of Secretory/Membrane Protein cDNA Derived from Mouse Skeletal Muscle The mouse proB cell line Ba/F3 (RIKEN Cell Bank; RCB0805) requires IL-3 for its survival and growth. The cells of this line have expressed a thrombopoietin receptor (MPL) on the cell membrane, which receptor forms a homo-dimer upon binding of the ligand thrombopoietin, whereby growth signals are transmitted into the cells. It has been found that MPL becomes a ligand-independent constitutive active form ($MPL^M$) by $Ser^{498}Asn$ mutation in the transmembrane region, the survival and growth of Ba/F3 is maintained even in the absence of IL-3, and in addition $MPL^M$ activity does not require the majority of the extracellular domain, and if amino acid 187 at the C-terminus is included, it is capable of being expressed on the cell membrane and forming a homo-dimer (Kojima and Kitamura, Nature Biotech., 17: 487-490, 1999). That is, if a retroviral vector designed to allow a cDNA to be incorporated into the 5' side of $MPL^M$ deprived of the extracellular region is constructed, and provided that the incorporated cDNA has a signal sequence, a fusion protein of the cDNA-encoded protein and $MPL^M$ would be expressed on the cell membrane of Ba/F3 and the Ba/F3 would be able to survive and grow in the absence of IL-3. Based on this principle, a cDNA derived from the soleus of free feeding, fasted, and re-feeding mice was inserted into the BstXI site of a retroviral vector comprising the coding region of $MPL^M$ deprived of $Met^1$-$Thr^{44}$ ($\Delta MPL^M$) (pMX-SST; Kojima and Kitamura, ibidem) to construct a retrovirus expression library, and cloning of secretory/membrane protein cDNA was performed.

First, the soleus was excised from free feeding, fasted, and re-feeding mice (C57Bl/6J, 13-week-old, female; after 24 hours of fasting for the fasted mice, or after 6 hours following the start of re-feeding after fasting for the re-feeding mice), poly A(+) RNA was isolated using the Quick Prep mRNA Purification Kit (Pharmacia) according to the protocol attached, and converted into a cDNA with a random hexamer using the SuperScript Choice System (Gibco-BRL). The cDNA obtained was inserted into the BstXI site of the retroviral vector pMX-SST using the BstXI adapter (Invitrogen), and the cDNA was ligated to the 5' side of $MPL^M$. The DNA obtained was introduced into the E. coli DH10B strain using the electroporation method, and amplified. Plasmid DNA was purified according to a conventional method, and transfected into packaging cells for constructing retrovirus (Plat-E; Morita et al., Gene Ther., 7(12): 1063-1066, 2000; obtained from Dr. Toshio Kitamura, the Institute of Medical Science, the University of Tokyo) ($2 \times 10^6$ cells/dish) using the Lipofectamine™ reagent (Invitrogen) according to the protocol attached. After cultivation in a DMEM medium supplemented with 10% fetal bovine serum for 24 hours, the medium was exchanged with a fresh medium, and the cells were further cultured for 24 hours and the culture supernatant was collected to give a high-titer retrovirus stock having infectivity (infection efficiency 10-30%). Cells for protein expression (Ba/F3) were infected with this retrovirus stock and cultured in an RPMI 1640 medium supplemented with IL-3 for 8 to 24 hours, then the cells were sown to a 96-well plate at 1 to $10 \times 10^3$ cells/well, and selected in IL-3 free medium. Ba/F3 cells retaining growing capacity after infection were selected, and genomic DNA was extracted therefrom by a conventional method. Then, PCR was performed with the genomic DNA as the template using primers 1 and 2 (SEQ ID NO:5 and 6) (98° C., 60 seconds, followed by 98° C., 20 seconds and then 68° C., 120 seconds; 30 cycles). The base sequence of the amplified fragment was determined using the BigDye Terminator Cycle Sequencing FS Ready Kit (PE Biosystems) and an automated DNA sequencer (ABI Prism 377); the cDNA clone shown by SEQ ID NO:7 was identified.

EXAMPLE 2

Cloning of the Mouse SS169 Gene

A search with the NCBI blast was performed on the basis of the above-described sequence; homology to XM-155941 LOC239790 was demonstrated. A 5'-RACE primer (TCCTGAGCCCCACAGCATCACAATCATAGC; SEQ ID NO:8) and a 3'-RACE primer (CCTTGACAGACTCTCAGCT; SEQ ID NO:9) were designed on the basis of this sequence, and 5'-RACE and 3'-RACE were performed (Clontech SMARTT™ RACE cDNA amplification kit). The experiments were performed per the operating manual attached to the kit. Total RNA was extracted from C57BL/6J mouse skeletal muscle, and adapter addition and a reverse transcription reaction were carried out to prepare a cDNA. PCR was performed on the basis of this cDNA (94° C. 5 sec, 72° C. 3 min=5 cycles, 94° C. 5 sec, 69° C. 10 sec, 72° C. 3 min=5 cycles, 94° C. 5 sec, 66° C. 10 sec, 72° C. 3 min=40 cycles). The PCR product was separated by 1% agarose gel electrophoresis, and the band obtained was cleaved out from the gel, extracted, and subjected to TA cloning (PROMEGA pGEM-T EASY). When the sequence of the plasmid obtained was determined, this gene was found to be novel. The 1153-bp cDNA fragment obtained (SEQ ID NO:10) consisted of five exons (as determined from the results of a mouse genome blast search) and comprised the ORF shown by SEQ ID NO:3 and 4 comprising 393 bp and 130aa. Escherichia coli competent cell DH5α (Invitrogen) was transformed with the plasmid pGEM-T incorporating this cDNA clone (clone 169).

EXAMPLE 3

Cloning of the Human SS169 Gene

A blast search on the human genome was performed on the basis of the above-described sequence of the mouse SS169 gene; the presence of a sequence highly homologous to mouse exons 2 and 3 was demonstrated. A 5'-RACE primer (GACTGTGGGTGTTGACTGCACATCTATG; SEQ ID NO:11) and a 3'-RACE primer (CTGATCTTTCACGAGATGCTGGACTGGA; SEQ ID NO:12) were designed on the basis of this sequence, and 5'-RACE and 3'-RACE were performed (Clontech SMART™ RACE cDNA amplification kit). The experiments were performed per the operating manual attached to the kit. Adapter addition and a reverse transcription reaction were carried out using a human skeletal muscle RNA (Clontech) to prepare a cDNA. PCR was performed on the basis of this cDNA (94° C. 5 sec, 72° C. 3 min=5 cycles, 94° C. 5 sec, 69° C. 10 sec, 72° C. 3 min=5 cycles, 94° C. 5 sec, 66° C. 10 sec, 72° C. 3 min=40 cycles). The PCR product was separated by 1% agarose gel electrophoresis, and the band obtained was cleaved out from the gel, extracted, and subjected to TA cloning (PROMEGA pGEM-T EASY). When the sequence of the plasmid obtained was determined, this gene was found to be novel. The 1655-bp cDNA fragment obtained (SEQ ID NO:13) comprised the ORF shown by SEQ ID NO:1 and 2 comprising 402 bp and 133aa. *Escherichia coli* competent cell DH5α (Invitrogen) was transformed with the plasmid pGEM-T (clone 169), which incorporates this cDNA clone.

EXAMPLE 4

Analysis of the Expression of the SS169 Gene

Using the primers shown by SEQ ID NO:14 and 15, the expression of the mouse SS169 gene was examined by the real-time PCR method under various conditions.

First, to examine expression tissues, total RNA was extracted from each tissue of 11-week-old male C57BL/6J mice, and PCR was performed using Light Cycler-FastStart DNA Master SYBR Green 1 (Roche Company) per the attached protocol (95° C. 10 min, 95° C. 15 sec, 65° C. 5 sec, 72° C. 15 sec, standing at room temperature). The results are shown in FIG. 1. Mouse SS169 was specifically expressed in skeletal muscles, with only small amounts expressed in other tissues, including brown adipose tissue and the like.

Figure 2:
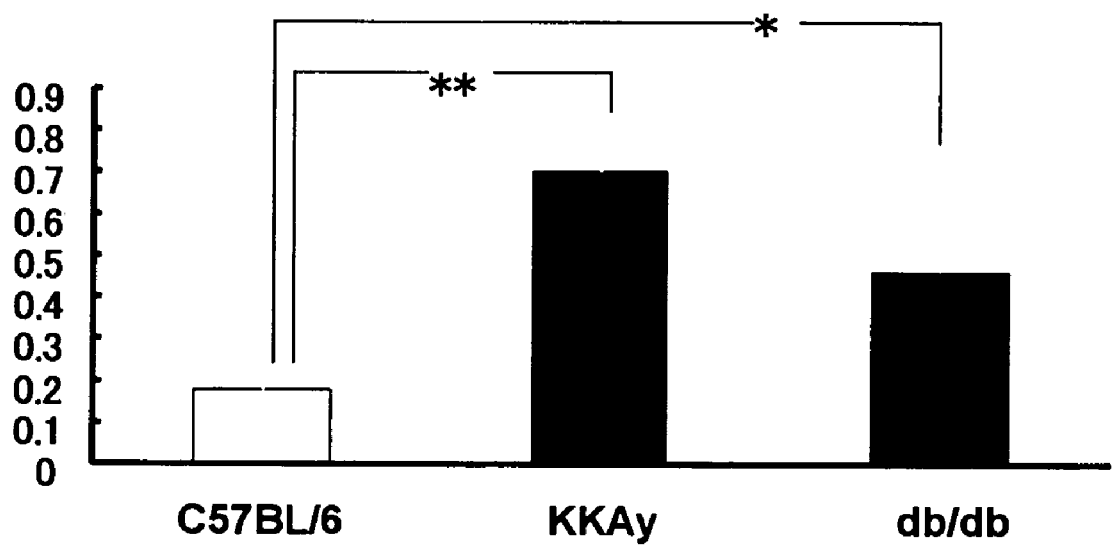
FIG. 2 shows the expression of the SS169 gene in skeletal muscles of diabetic model mice (KKAy, db/db) and normal mice (C57BL/6). The ordinate indicates an arbitrary unit. * indicates $p<0.01$; ** indicates $p<0.001$.

To examine the expression in pathologic animals, total RNA was extracted from skeletal muscles of 12-week-old male C57BL/6J mice, female KKA$^y$ mice, and 11-week-old male db/db mice, and the expression amount was determined in the same manner as the determination of the expression tissue distribution. As shown in FIG. 2, the KKA$^y$ mice exhibited a higher expression amount than C57BL/6J, with a high expression amount also observed in the db/db mice.

Figure 3:
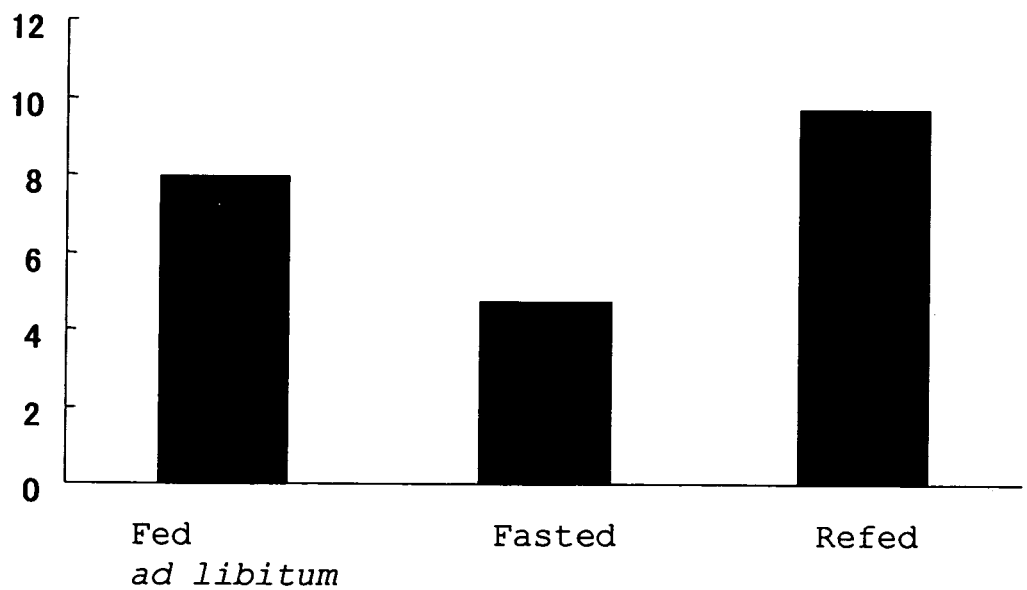
FIG. 3 shows the expression of the SS169 gene in mouse skeletal muscles during free feeding, during fasting, and during re-feeding. The ordinate indicates an arbitrary unit.

Furthermore, changes in the expression with different feeding conditions were measured using the total RNA used in Example 1; the expression amount decreased under fasting conditions than under free feeding conditions, and the expression amount normalized with re-feeding, as shown in FIG. 3.

EXAMPLE 5

Cloning of the Rat SS169 Gene

A blast search on the rat genome was performed on the basis of the sequence of the mouse SS169 gene; the presence of NWO47356, a sequence highly homologous to mouse exons 1 and 2, was demonstrated. Four kinds of 3'-RACE primers (SEQ ID NO:16, 17, 18 and 19) were designed on the basis of this sequence, and 3'-RACE was performed. The experiments were performed per the operating manual attached to the kit (Clontech SMART™ RACE cDNA amplification kit). A reverse transcription reaction was carried out using total RNA extracted from the rat gastrocnemius using the RNA-STAT 60 kit (manufactured by Friendswood Company) to prepare a cDNA. PCR was performed with this cDNA as the template using the primers shown by SEQ ID NO:20 and 21, and the base sequence of the rat SS169 gene (SEQ ID NO:22) was determined from the sequence of the PCR product obtained.

EXAMPLE 6

Tissue Distribution of the Rat SS169 Gene

Using the primers shown by SEQ ID NO:24 and 25, tissues in which the rat SS169 gene was expressed were examined by the real-time PCR method.

Figure 4:
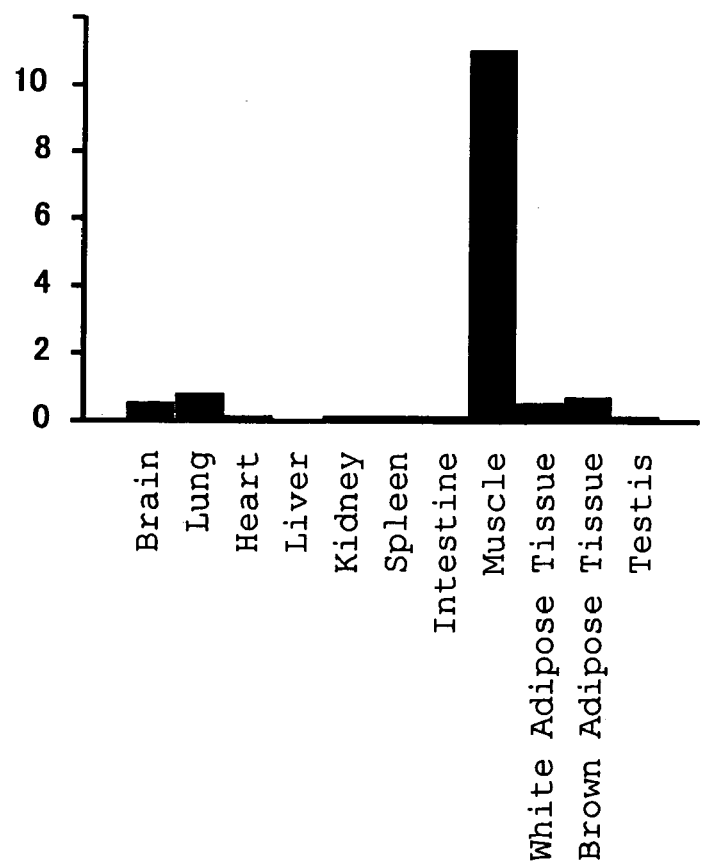
FIG. 4 shows the tissue distribution of the expression of the rat SS169 gene [the brain, lung, heart, liver, kidney, spleen, intestine, muscles, white adipose tissue, brown adipose tissue and testis are shown from the left]. The ordinate indicates an arbitrary unit.

Total RNA was extracted from each tissue of 6-week-old male SD rats, and PCR was performed using Light Cycler-FastStart DNA Master SYBR Green 1 (Roche Company) per the attached protocol (95° C. 10 min, 95° C. 15 sec, 65° C. 5 sec, 72° C. 15 sec. standing at room temperature). The results are shown in FIG. 4. The rat SS169 gene was specifically expressed in skeletal muscles, with only small amounts expressed in other tissues, including brown adipose tissue and the like.

EXAMPLE 7

Changes in the Expression in Mouse Skeletal Muscle-Derived Cell Line

Using the mouse skeletal muscle-derived cell line C2C12, the expression of the SS169 gene during differentiation induction and the influence of insulin on the expression of the SS169 gene were examined.

Figure 5:
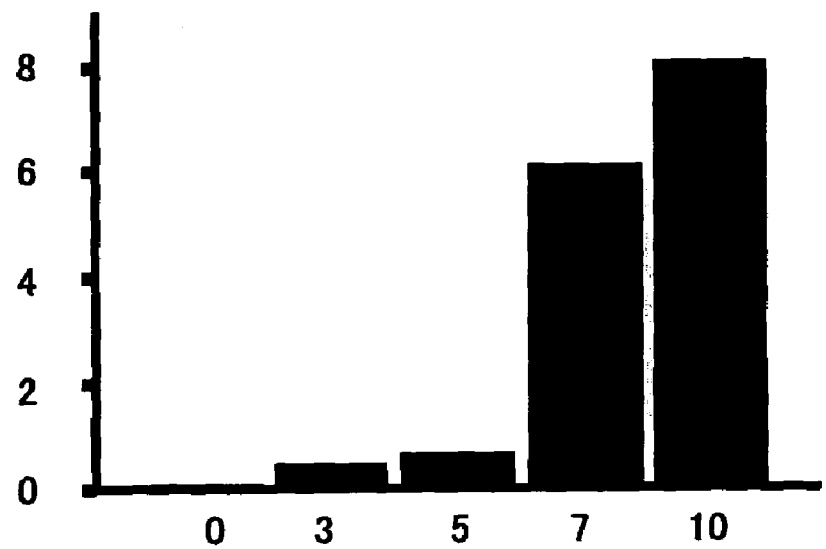
FIG. 5 shows changes in the expression of the SS169 gene over days during induction of differentiation of the mouse skeletal muscle-derived cell line C2C12. The ordinate indicates an arbitrary unit; the abscissa indicates the number of days after induction of differentiation.

C2C12 cells were cultured on a collagen-coated plate using a DMEM supplemented with 10% FCS. After the cells grew to confluency, the medium was replaced with a DMEM containing 2% equine serum to induce differentiation. On days 0, 3, 5, 7, and 10 after differentiation induction, total RNA was extracted, and the expression amount of the SS169 gene was quantified in the same manner as Example 4. The results are shown in FIG. 5. Expression induction of the SS169 gene increased remarkably on day 7 after differentiation induction and thereafter.

Figure 6:
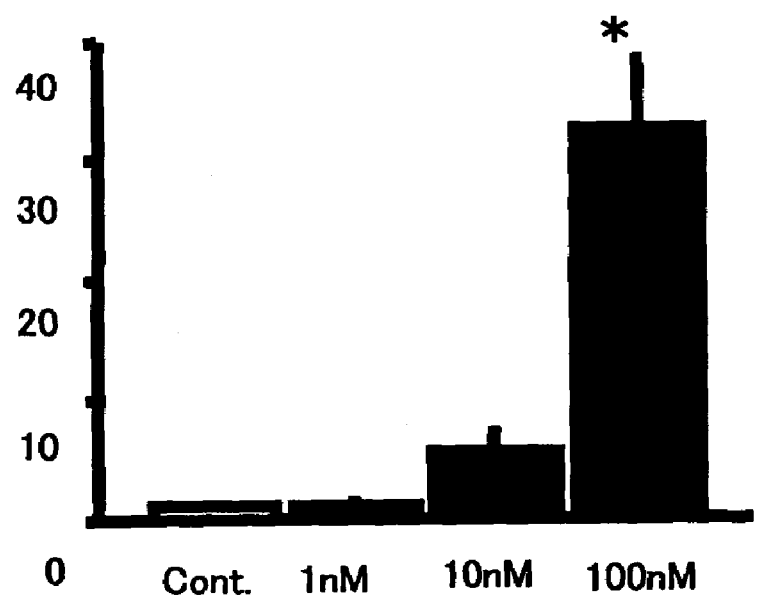
FIG. 6 shows the influence of insulin on the expression of the SS169 gene in the mouse skeletal muscle-derived cell line C2C12. The ordinate indicates an arbitrary unit; the abscissa indicates insulin concentration. Cont. represents C2C12 cultured in an insulin-free medium. * indicates $p<0.01$.

On the other hand, for the influence of insulin, the medium for cells on day 7 after differentiation induction was replaced with DMEMs supplemented with various concentrations of insulin (see FIG. 6); 24 hours later, total RNA was prepared from the cells and quantified. The results are shown in FIG. 6. Insulin increased the expression of the SS169 gene concentration-dependently.

EXAMPLE 8

Changes in the Expression in STZ Mouse Skeletal Muscles

Figure 7:
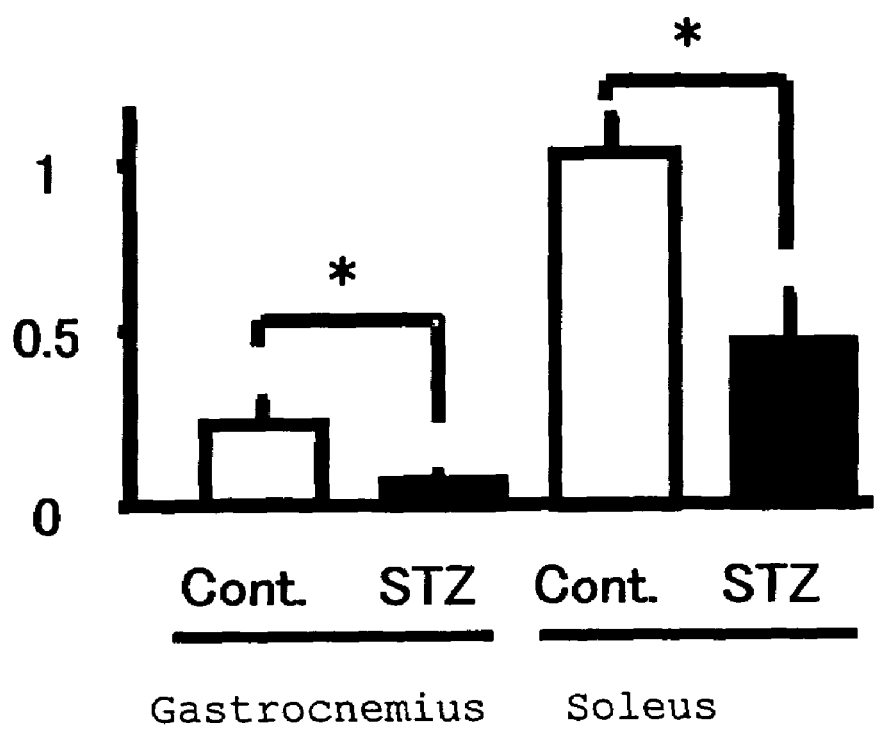
FIG. 7 shows the expression of the SS169 gene in skeletal muscles (the gastrocnemius and the soleus) of diabetic model mice receiving streptozotocin (STZ). The ordinate indicates an arbitrary unit. "Cont." shows the results from mice not receiving STZ. * indicates $p<0.01$.

Ten-week-old male C57BL/6J mice, previously fasted for 12 hours, were given an intraperitoneal administration of streptozosin (STZ) at 100 mg/kg, and fed for 12 hours after the administration; this was repeated three times to prepare STZ mice. Four days after final administration of STZ, total RNA was extracted from a skeletal muscle, and the expression amount of the SS169 gene was quantified in the same manner as Example 4. The results are shown in FIG. 7. In the STZ mice, a model of type 1 diabetes, the expression of the SS169 gene decreased significantly in both the gastrocnemius and the soleus compared to control mice.

EXAMPLE 9

Preparation of Cell Lines that Stably Express the SS169 Gene

Figure 8A:
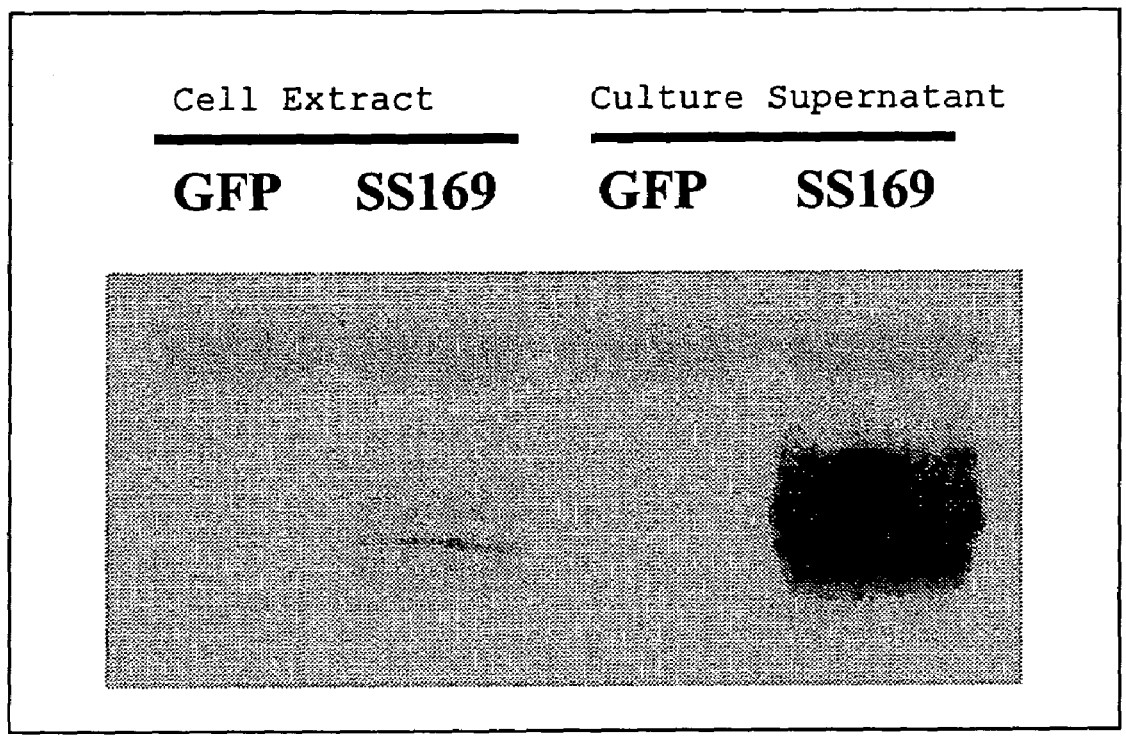
FIG. 8 shows the localization of SS169 in cell lines that stably express the SS169 gene (A: NIH3T3 cells; B: C2C12 cells). The SS169 or GFP gene having a Flag-tag attached thereto was introduced to each cell line, each of the cell extract and culture supernatant was immunoprecipitated using an anti-Flag antibody, and SDS-polyacrylamide gel electrophoresis was performed; thereafter, Western blotting using an anti-Flag antibody was performed.
Figure 8B:
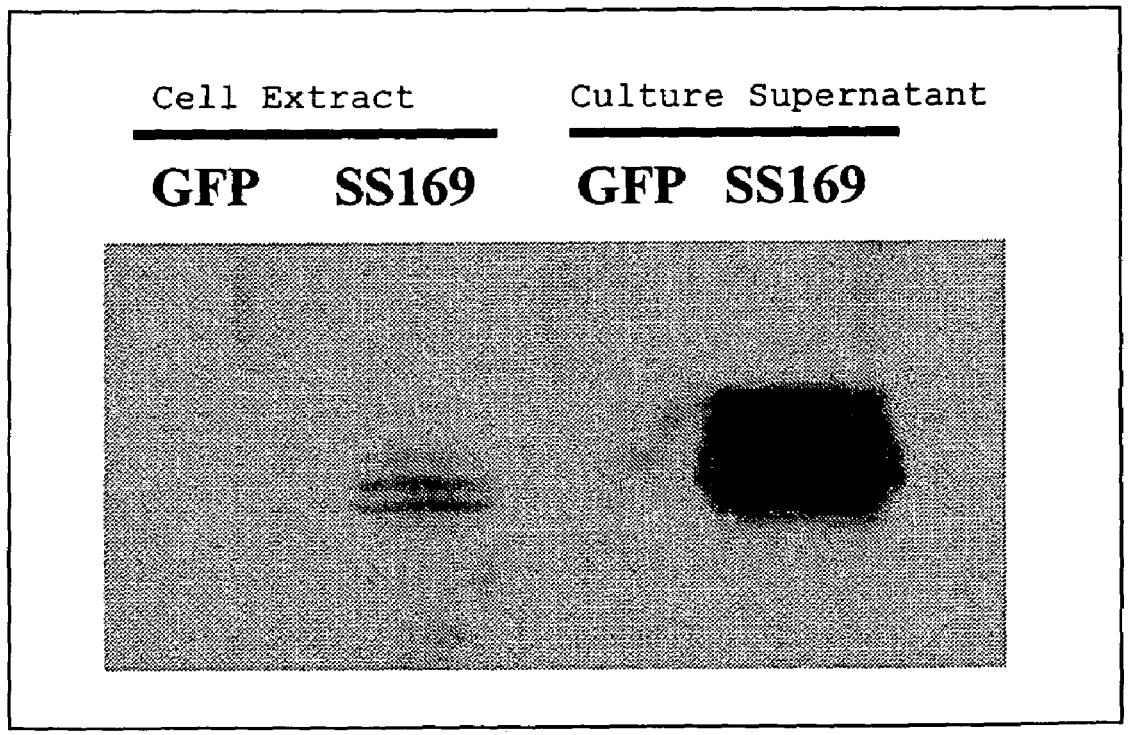

The expression vector pMXs-puro incorporating the SS169 gene or GFP gene having a Flag-tag added to the C-terminus was prepared and introduced to PlatE cells, which are retrovirus packaging cells, using FuGENE6. Forty-eight hours after the gene introduction, the viral liquid was recovered and infected to C2C12 cells and NIH3T3 cells. Viral-infected cells were selected through cultivation in a medium supplemented with puromycin (2 μg/ml) for 24 hours, to yield cell lines that stably express the SS169 gene. The stably expressing lines obtained were treated respectively. In the case of C2C12, the medium was replaced with an FCS-free medium on day 7 of differentiation induction; after 24 hours, the culture supernatant and cell extract were immunoprecipitated using an anti-Flag antibody and subjected to SDS-polyacrylamide gel electrophoresis, thereafter the SS169 gene product was detected by Western blotting using anti-Flag antibody. In the case of NIH3T3, the medium for cells cultured until confluency was replaced with an FCS-free medium, and treated in the same manner as C2C12, to detect the SS169 gene product. As shown in FIG. 8, the SS169 gene product was mostly present in the culture supernatant; it was found that SS169 is extracellularly secreted in C2C12 and NIH3T3 cells.

EXAMPLE 10

Preparation of SS169 Expression Adenovirus Vector

Figure 9:
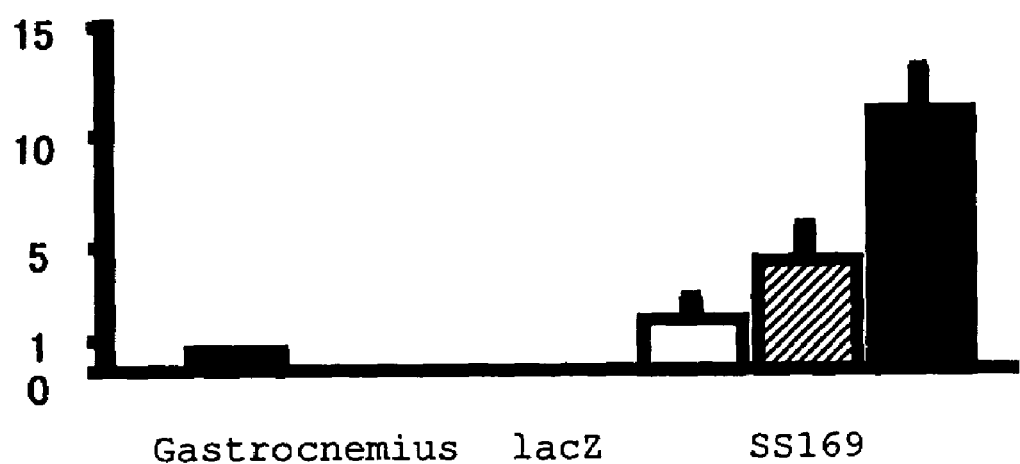
FIG. 9 shows the expression amounts of the SS169 gene in the livers of mice infected with an adenovirus that expresses the mouse SS169 gene at a low titer ($2\times10^7$ pfu), medium titer ($6\times10^7$ pfu), and high titer ($2\times10^8$ pfu). For control, mice similarly infected with an adenovirus that expresses the lacZ gene were used. The ordinate indicates an arbitrary unit. The bar graphs show the results for the low titer, medium titer, and high titer, from the left. "The gastrocnemius" shows the expression amount of the SS169 gene in the gastrocnemius of non-infected mice.
Figure 10A:
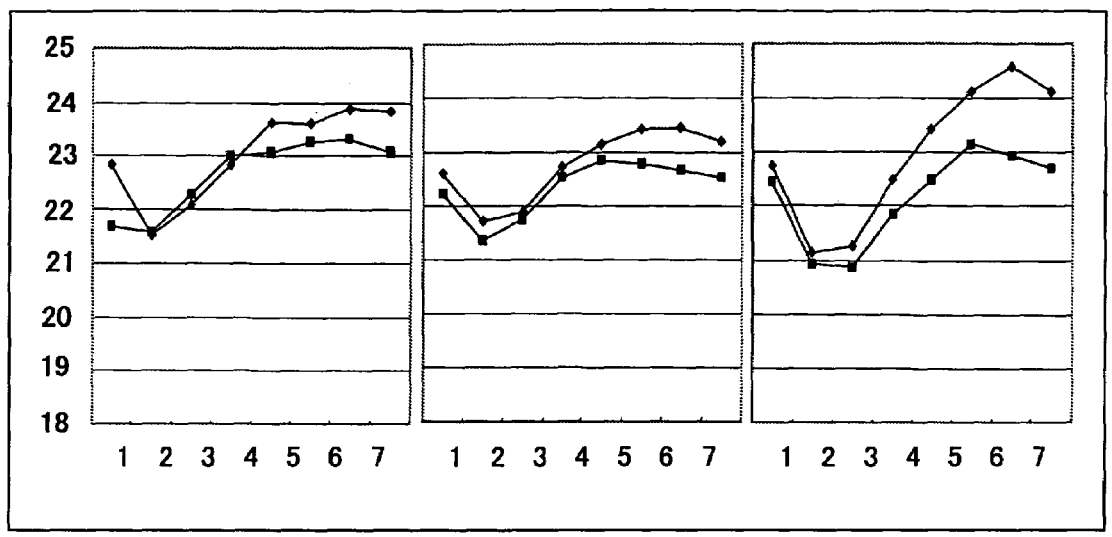
FIG. 10 shows changes over days in body weight (A) and food consumption (B) in mice infected with an adenovirus that expresses the mouse SS169 gene at a low titer ($2\times10^7$ pfu), medium titer ($6\times10^7$ pfu), and high titer ($2\times10^8$ pfu). For control, mice similarly infected with an adenovirus that expresses the lacZ gene were used. The ordinate indicates (A) body weight (unit of measurement: g) and (B) food consumption (unit of measurement: g/day); the abscissa indicates the number of days after viral infection. -♦- shows the results from the mice infected with the adenovirus that expresses the lacZ gene, and -■- shows the results from the mice infected with the adenovirus expressing the SS169 gene.
Figure 10B:
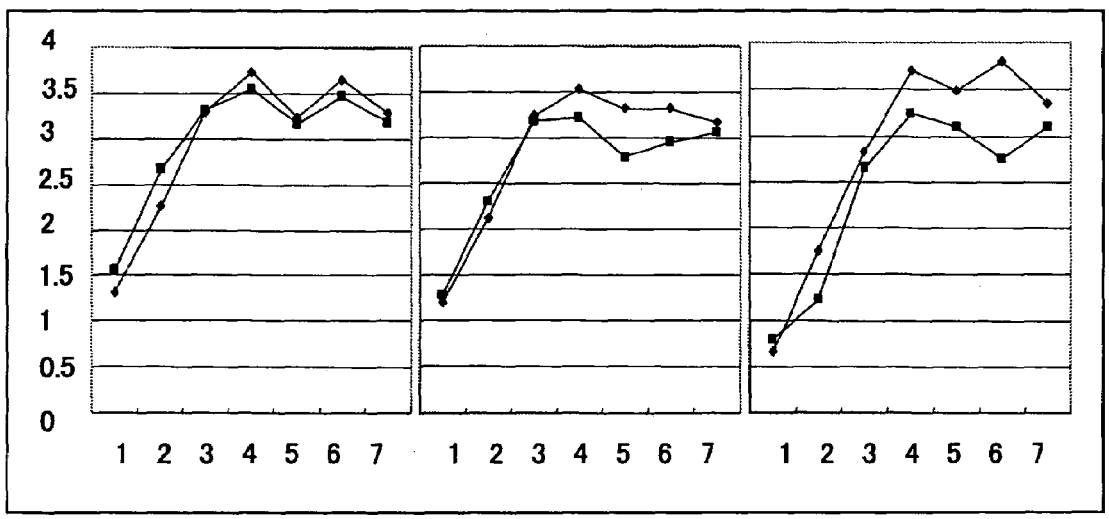
Figure 11:
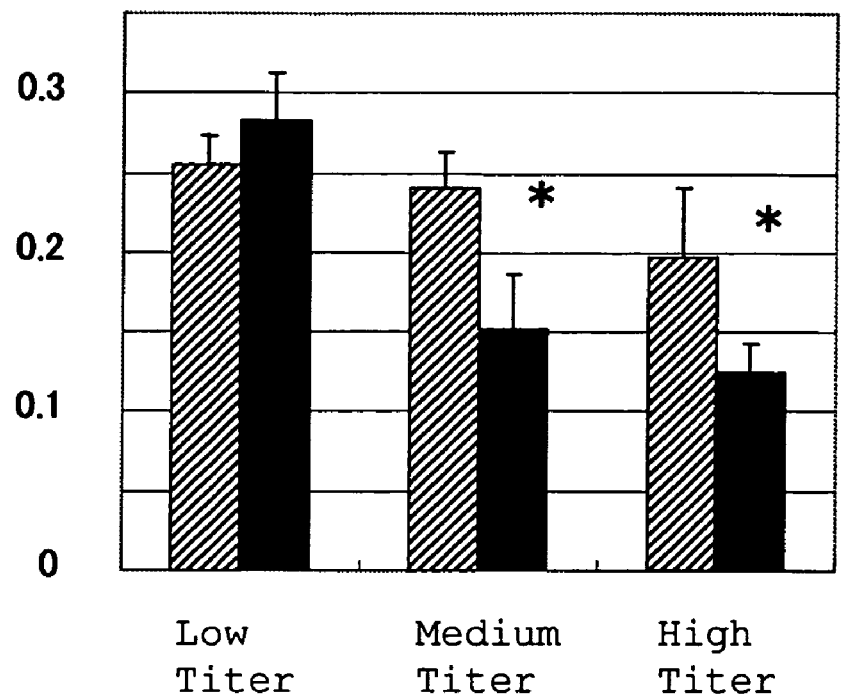
FIG. 11 shows the weights of adipose around the epididymis in mice infected with an adenovirus that expresses the mouse SS169 gene at a low titer ($2\times10^7$ pfu), medium titer ($6\times10^7$ pfu), and high titer ($2\times10^8$ pfu). The ordinate indicates the weight of adipose around the epididymis (unit of measurement: g). The bar graphs show the results from mice infected with an adenovirus that expresses the lacZ gene and the results from the mice infected with the adenovirus that expresses the SS169 gene, from the left, for each titer. * indicates $p<0.01$.
Figure 12:
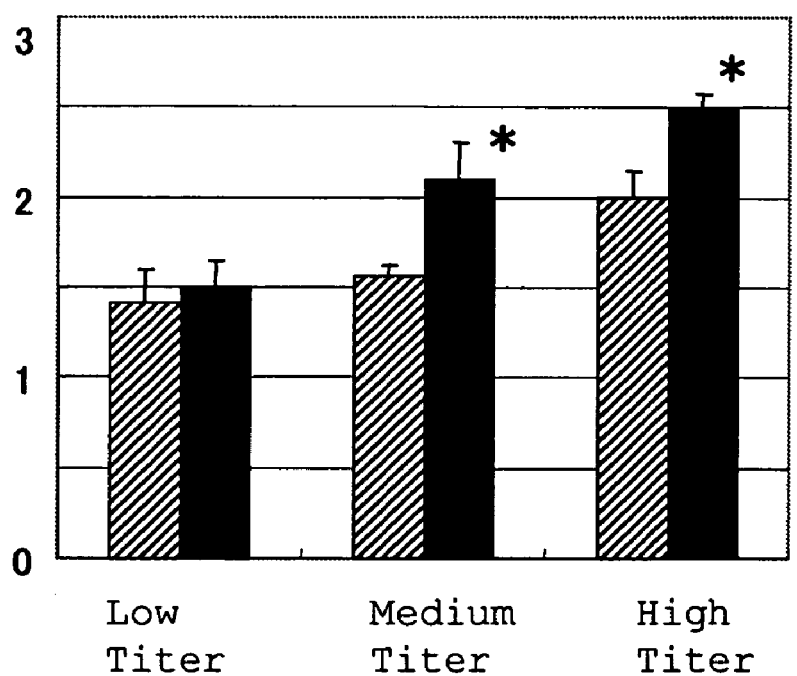
FIG. 12 shows the weights of livers in mice infected with an adenovirus that expresses the mouse SS169 gene at a low titer ($2\times10^7$ pfu), medium titer ($6\times10^7$ pfu), and high titer ($2\times10^8$ pfu). The ordinate indicates liver weight (unit of measurement: g). The bar graphs show the results from mice infected with an adenovirus that expresses the lacZ gene and the results from the mice infected with the adenovirus that expresses the mouse SS169 gene, from the left, for each titer. * indicates $p<0.01$.
Figure 13A:
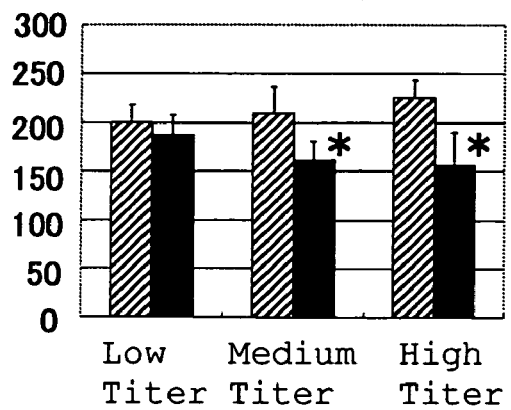
FIG. 13 shows (A) blood glucose levels (unit of measurement: mg/dl), (B) blood insulin levels (unit of measurement: ng/ml), (C) blood free fatty acid concentrations (unit of measurement: mEq/l), and (D) blood triglyceride concentrations (unit of measurement: mg/dl) in mice infected with an adenovirus that expresses the mouse SS169 gene at a low titer ($2\times10^7$ pfu), medium titer ($6\times10^7$ pfu), and high titer ($2\times10^8$ pfu). The bar graphs show the results from mice infected with an adenovirus that expresses the lacZ gene and the results from the mice infected with the adenovirus that expresses the SS169 gene, from the left, for each titer. * indicates $p<0.01$.
Figure 13B:
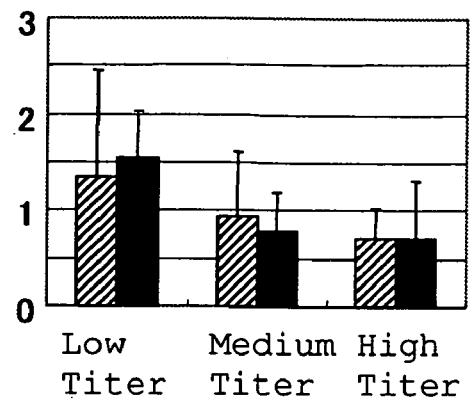
Figure 13C:
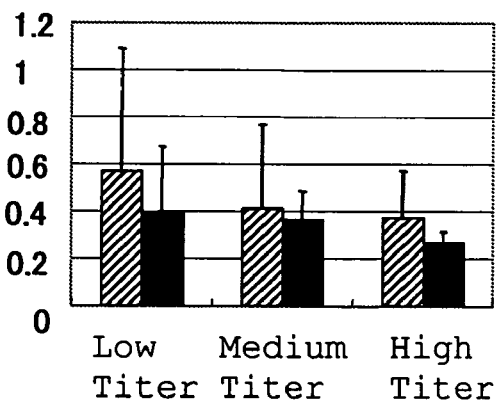
Figure 13D:
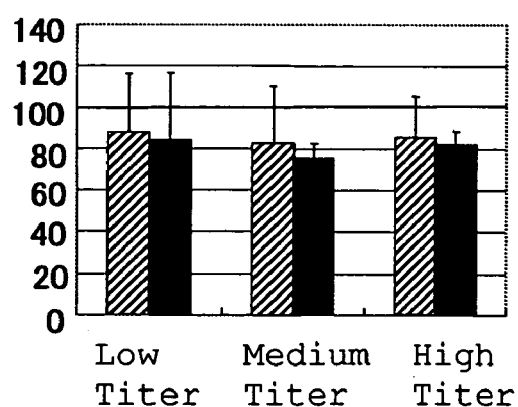

A mouse SS169 gene cDNA was inserted in the pShuttle-CMV vector, and the vector was transfected to *Escherichia coli*, along with pAdEasy, which comprises a type 5 adenovirus genome lacking E1-E3, to prepare a viral vector by homologous recombination. This viral vector was introduced to cells of the 293 line to prepare an adenovirus expressing the mouse SS169 gene. For control, a lacZ gene-expressing adenovirus was prepared in the same manner. The virus obtained was inoculated from the mouse tail vein at various titers to cause infection. FIG. 9 shows the expression amount of the SS169 gene in the liver of a virus-infected mouse; FIG. 10 shows changes in body weight and food consumption after infection; FIGS. 11 and 12 show the weights of adipose around the epididymis and liver; and FIG. 13 shows the results of measurements of blood glucose level, blood insulin level, blood free fatty acid concentration, and blood triglyceride concentration. Note that in these figures, low titer, medium titer, and high titer indicate cases where the virus was inoculated to the mouse at $2\times10^7$, $6\times10^7$ and $2\times10^8$ pfu, respectively. In the mice infected with the SS169 gene expression virus, the expression amount of the SS169 gene in the liver increased titer-dependently (FIG. 9). In the mice infected with the SS169 gene expression virus at high titer, body weight and food consumption tended to decrease (FIG. 10). In the mice infected with the SS169 gene expression virus at medium titer and high titer, adipose around the epididymis decreased significantly (FIG. 11), liver weight increased significantly (FIG. 12), and blood glucose level decreased significantly (FIG. 13).

EXAMPLE 11

Influence on Sugar Uptake Activity of Skeletal Muscle Cells

Figure 14A:
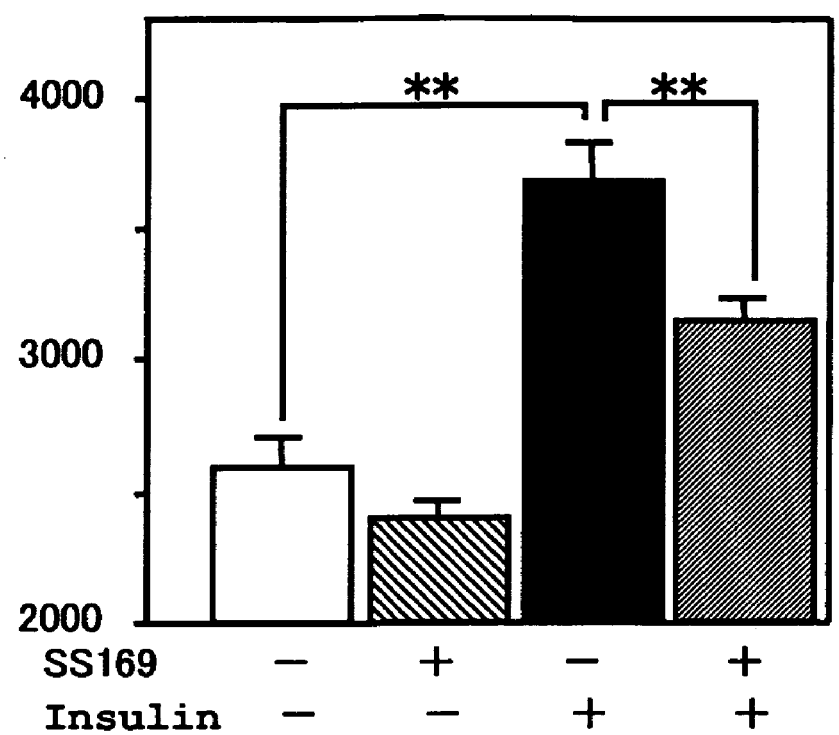
FIG. 14 shows the effects of SS169 on $^3$H-2-deoxy-D-glucose (2-DG) uptake in C2C12 cells with and without insulin stimulation (A) and on the expression of the GLUT4, GLUT1 and hexokinase II (HK II) genes with insulin stimulation (B). In A, the ordinate indicates 2-DG uptake (cpm/well); ** indicates $p<0.001$. In B, the ordinate indicates an arbitrary unit; n.s. indicates the absence of a significant difference.
Figure 14B:
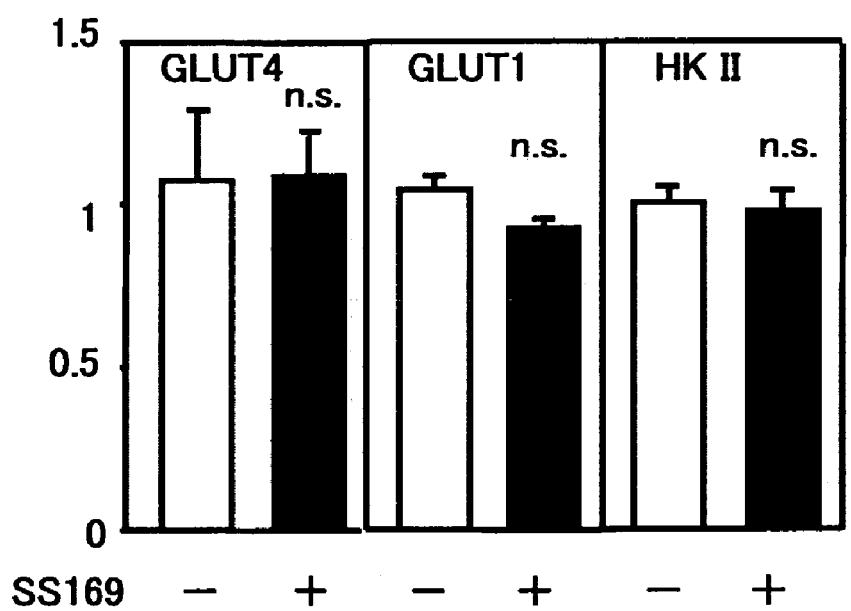

Using C2C12 cells, the influence of SS169 on sugar uptake was examined. On day 5 of differentiation induction, the medium for C2C12 cells was replaced with an FCS-free DMEM, 0.5 µg/ml of SS169 with the Flag-tag was added, and the cells were cultured for 5 hours. Subsequently, insulin (100 nM) stimulation was given for 30 minutes, and $^3$H-2-deoxy-D-glucose uptake activity in the cells was determined using a scintillation counter, as reported previously (Am. J. Physiol. 276, E849-E855, 1999). Note that the SS169 with the Flag-tag used had been purified from a culture supernatant of the C2C12 cell line that stably expresses SS169 described in Example 9, using an anti-Flag antibody column. The results of the measurement of sugar uptake are shown in FIG. 14A. Sugar uptake in C2C12 during insulin stimulation was suppressed by the addition of SS169. When the expression amounts of the Glut4 (insulin-dependent sugar transport carrier), Glut1 (non-insulin-dependent sugar transport carrier), and hexokinase II (phosphorylates glucose to reduce the free glucose concentration, and to promote sugar uptake in cells) genes in C2C12 cells during insulin stimulation were measured by RT-PCR, their expression amounts did not change with the addition of SS169 (FIG. 14B). From this finding, it is considered that sugar uptake was not suppressed due to a reduction in the expression of these genes, but was suppressed as a result of an influence of SS169 on insulin action.

EXAMPLE 12

Influence on Glycogen Synthesis in Skeletal Muscle Cells

Using C2C12 cells cultured and treated with SS169 in the same manner as Example 11, the influence of SS169 on glycogen synthesis was examined. Glycogen synthesis was measured with D-[1–$^{14}$C]glucose uptake in intracellular glycogen fraction as an index in accordance with a published report (J. Biol. Chem. 274, 24202-21210, 1999). The results are shown in FIG. 15. Glycogen synthesis in C2C12 cells was suppressed by the addition of SS169.

INDUSTRIAL APPLICABILITY

Since SS169 is a secretory or membrane protein expressed in skeletal muscle cells in feeding state and in diabetes mellitus and obesity, it is useful as a prophylactic/therapeutic agent or diagnostic agent for a disease associated with an abnormality of differentiation of skeletal muscle cell or metabolism function, or as a tool for screening a drug-candidate compound effective for the prophylaxis/treatment of the disease.

This application is based on a patent application Nos. 2003-071188, 2003-391047, 2004-23557 and 2004-30988 filed in Japan, the contents of which are hereby incorporated by reference.

Sequence List Free-Text

[SEQ ID NO:5]
An oligonucleotide designed to function as a primer for amplifying a mouse soleus-derived cDNA.
[SEQ ID NO:6]
An oligonucleotide designed to function as a primer for amplifying a mouse soleus-derived cDNA.
[SEQ ID NO:8]
An oligonucleotide designed to function as a primer for amplifying a full-length mouse SS169 cDNA.
[SEQ ID NO:9]
An oligonucleotide designed to function as a primer for amplifying a full-length mouse SS169 cDNA.
[SEQ ID NO:11]
An oligonucleotide designed to function as a primer for amplifying a full-length human SS169 cDNA.
[SEQ ID NO:12]
An oligonucleotide designed to function as a primer for amplifying a full-length human SS169 cDNA.
[SEQ ID NO:13]
(Base No:763)
n represents an unidentified base.
(Base No:965)
n represents an unidentified base.
(Base No:1032)
n represents an unidentified base.

(Base No:1033)
n represents an unidentified base.
(Base No:1043)
n represents an unidentified base.
(Base No:1075)
n represents an unidentified base.
(Base No:1080)
n represents an unidentified base.
(Base No:1113)
n represents an unidentified base.
(Base No:1138)
n represents an unidentified base.
(Base No:1235)
n represents an unidentified base.
(Base No:1238)
n represents an unidentified base.
(Base No:1265)
n represents an unidentified base.
(Base No:1277)
n represents an unidentified base.
(Base No:1280)
n represents an unidentified base.
(Base No:1291)
n represents an unidentified base.
(Base No:1301)
n represents an unidentified base.
(Base No:1328)
n represents an unidentified base.
(Base No:1347)
n represents an unidentified base.
(Base No:1366)
n represents an unidentified base.
(Base No:1454)
n represents an unidentified base.
(Base No:1553)
n represents an unidentified base.
(Base No:1580)
n represents an unidentified base.
(Base No:1625)
n represents an unidentified base.

[SEQ ID NO:14]
An oligonucleotide designed to function as a primer for amplifying a mouse SS169 cDNA fragment.
[SEQ ID NO:15]
An oligonucleotide designed to function as a primer for amplifying a mouse SS169 cDNA fragment.
[SEQ ID NO:16]
An oligonucleotide designed to function as a primer for amplifying a full-length rat SS169 cDNA.
[SEQ ID NO:17]
An oligonucleotide designed to function as a primer for amplifying a full-length rat SS169 cDNA.
[SEQ ID NO:18]
An oligonucleotide designed to function as a primer for amplifying a full-length rat SS169 cDNA.
[SEQ ID NO:19]
An oligonucleotide designed to function as a primer for amplifying a full-length rat SS169 cDNA.
[SEQ ID NO:20]
An oligonucleotide designed to function as a primer for amplifying a rat gastrocnemius-derived cDNA.
[SEQ ID NO:21]
An oligonucleotide designed to function as a primer for amplifying a rat gastrocnemius-derived cDNA.
[SEQ ID NO:24]
An oligonucleotide designed to function as a primer for amplifying a rat SS169 cDNA fragment.
[SEQ ID NO:25]
An oligonucleotide designed to function as a primer for amplifying a rat SS169 cDNA fragment.

---

The invention claimed is:

1. A screening method for a therapeutic substance for a disease associated with abnormal differentiation of skeletal muscle cell and/or metabolic abnormality, which comprises 1) bringing a protein, or a salt thereof, comprising the amino acid sequence starting at amino acid No. 1 in the amino acid sequence shown by SEQ ID NO: 2 or 4 into contact with its receptor in the presence or absence of a test substance, and 2) selecting the test substance that changes the ability of said protein or salt thereof to bind to said receptor as a candidate for a therapeutic substance for a disease associated with abnormal differentiation of skeletal muscle cell and/or metabolic abnormality and 3) confirming that the test substance does change the ability of the protein to bind to its receptor by demonstrating that sugar uptake is suppressed under insulin stimulation in skeletal muscle cells.

2. A screening method for a therapeutic substance for a disease associated with abnormal differentiation of skeletal muscle cell and/or metabolic abnormality, which comprises 1) bringing a protein, or a salt thereof, comprising the amino acid sequence starting at amino acid No. 1 in the amino acid sequence shown by SEQ ID NO: 2 or 4 into contact with its receptor in the presence or absence of a test substance, and 2) selecting the test substance that changes the ability of said protein or salt thereof to bind to said receptor as a candidate for a therapeutic substance for a disease associated with abnormal differentiation of skeletal muscle cell and/or metabolic abnormality and 3) confirming that the test substance does change the ability of the protein to bind to its receptor by demonstrating that glycogen synthesis is suppressed in skeletal muscle cells.

3. The screening method of claim 1 or 2, wherein the metabolic abnormality is a sugar/lipid metabolic abnormality.

4. The screening method of claim 1 or 2, wherein the disease is obesity, diabetes mellitus, impaired glucose tolerance, arteriosclerosis, hypertension or hyperlipemia.

* * * * *

UNITED STATES PATENT AND TRADEMARK OFFICE
CERTIFICATE OF CORRECTION

PATENT NO. : 7,700,361 B2
APPLICATION NO. : 10/561144
DATED : April 20, 2010
INVENTOR(S) : Iichirou Shimomura et al.

It is certified that error appears in the above-identified patent and that said Letters Patent is hereby corrected as shown below:

On page 1, after the "Prior Publication Data" section [65], add:

Foreign Application Priority Data
June 16, 2003    (JP)    2003-171188
November 20, 2003    (JP)    2003-391047
January 30, 2004    (JP)    2004-023557
February 6, 2004    (JP)    2004-030988

On page 20, Column 17, Line 62, "*Escherichia coli* K12•DH1" should be "*Escherichia coli* K12•DH1".

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

PATENT NO. : 7,700,361 B2
APPLICATION NO. : 10/561144
DATED : April 20, 2010
INVENTOR(S) : Iichirou Shimomura et al.

It is certified that error appears in the above-identified patent and that said Letters Patent is hereby corrected as shown below:

On page 1, after the "Prior Publication Data" section [65], add:

Foreign Application Priority Data
June 16, 2003 (JP) 2003-171188
November 20, 2003 (JP) 2003-391047
January 30, 2004 (JP) 2004-023557
February 6, 2004 (JP) 2004-030988

On page 20, Column 17, Line 62, "*Escherichia coli* K12●DH1" should be "*Escherichia coli* K12•DH1".

This certificate supersedes the Certificate of Correction issued November 23, 2010.

Signed and Sealed this
Twelfth Day of April, 2011

David J. Kappos
*Director of the United States Patent and Trademark Office*

SEQUENCE LISTING

```
<160> NUMBER OF SEQ ID NOS: 25

<210> SEQ ID NO 1
<211> LENGTH: 402
<212> TYPE: DNA
<213> ORGANISM: Homo sapiens
<220> FEATURE:
<221> NAME/KEY: CDS
<222> LOCATION: (1)..(399)
<220> FEATURE:
<221> NAME/KEY: sig_peptide
<222> LOCATION: (1)..(87)
<220> FEATURE:
<221> NAME/KEY: mat_peptide
<222> LOCATION: (88)..(399)

<400> SEQUENCE: 1 atg ctg gac tgg aga ttg gca agt gca cat ttc atc ctg gct gtg aca      48
Met Leu Asp Trp Arg Leu Ala Ser Ala His Phe Ile Leu Ala Val Thr
```

```
                    -25                 -20                 -15
ctg aca ctg tgg agc tca gga aaa gtc ctc tca gta gat gta aca aca         96
Leu Thr Leu Trp Ser Ser Gly Lys Val Leu Ser Val Asp Val Thr Thr
            -10                 -5                  -1  1 aca gag gcc ttt gat tct gga gtc ata gat gtg cag tca aca ccc aca        144
Thr Glu Ala Phe Asp Ser Gly Val Ile Asp Val Gln Ser Thr Pro Thr
      5                  10                  15 gtc agg gaa gag aaa tca gcc act gac ctg aca gca aaa ctc ttg ctt        192
Val Arg Glu Glu Lys Ser Ala Thr Asp Leu Thr Ala Lys Leu Leu Leu
 20                  25                  30                  35 ctt gat gaa ttg gtg tcc cta gaa aat gat gtg att gag aca aag aag        240
Leu Asp Glu Leu Val Ser Leu Glu Asn Asp Val Ile Glu Thr Lys Lys
                40                  45                  50 aaa agg agt ttc tct ggt ttt ggg tct ccc ctt gac aga ctc tca gct        288
Lys Arg Ser Phe Ser Gly Phe Gly Ser Pro Leu Asp Arg Leu Ser Ala
             55                  60                  65 ggc tct gta gat cac aaa ggt aaa cag agg aaa gta gta gat cat cca        336
Gly Ser Val Asp His Lys Gly Lys Gln Arg Lys Val Val Asp His Pro
         70                  75                  80 aaa agg cga ttt ggt atc ccc atg gat cgg att ggt aga aac cgg ctt        384
Lys Arg Arg Phe Gly Ile Pro Met Asp Arg Ile Gly Arg Asn Arg Leu
 85                  90                  95 tca aat tcc aga ggc taa                                                402
Ser Asn Ser Arg Gly
100

<210> SEQ ID NO 2
<211> LENGTH: 133
<212> TYPE: PRT
<213> ORGANISM: Homo sapiens

<400> SEQUENCE: 2

Met Leu Asp Trp Arg Leu Ala Ser Ala His Phe Ile Leu Ala Val Thr
                -25                 -20                 -15

Leu Thr Leu Trp Ser Ser Gly Lys Val Leu Ser Val Asp Val Thr Thr
            -10                 -5                  -1  1

Thr Glu Ala Phe Asp Ser Gly Val Ile Asp Val Gln Ser Thr Pro Thr
      5                  10                  15

Val Arg Glu Glu Lys Ser Ala Thr Asp Leu Thr Ala Lys Leu Leu Leu
 20                  25                  30                  35

Leu Asp Glu Leu Val Ser Leu Glu Asn Asp Val Ile Glu Thr Lys Lys
                40                  45                  50

Lys Arg Ser Phe Ser Gly Phe Gly Ser Pro Leu Asp Arg Leu Ser Ala
             55                  60                  65

Gly Ser Val Asp His Lys Gly Lys Gln Arg Lys Val Val Asp His Pro
         70                  75                  80

Lys Arg Arg Phe Gly Ile Pro Met Asp Arg Ile Gly Arg Asn Arg Leu
 85                  90                  95

Ser Asn Ser Arg Gly
100

<210> SEQ ID NO 3
<211> LENGTH: 393
<212> TYPE: DNA
<213> ORGANISM: Mus musculus
<220> FEATURE:
<221> NAME/KEY: CDS
<222> LOCATION: (1)..(390)
<220> FEATURE:
<221> NAME/KEY: sig_peptide
```

```
<222> LOCATION: (1)..(87)
<220> FEATURE:
<221> NAME/KEY: mat_peptide
<222> LOCATION: (88)..(390)

<400> SEQUENCE: 3 atg ctg gac tgg aga ttg gca agt aca cac ttc atc ctg gct atg att      48
Met Leu Asp Trp Arg Leu Ala Ser Thr His Phe Ile Leu Ala Met Ile
            -25                 -20                 -15 gtg atg ctg tgg ggc tca gga aag gca ttc tct gtg gac tta gca tca      96
Val Met Leu Trp Gly Ser Gly Lys Ala Phe Ser Val Asp Leu Ala Ser
        -10                  -5                  -1  1 cag gag ttt gga aca gca agc ttg cag tct cca ccc aca gcc aga gaa     144
Gln Glu Phe Gly Thr Ala Ser Leu Gln Ser Pro Pro Thr Ala Arg Glu
      5                  10                  15 gag aag tca gcc act gag ctt tcg gct aag ctc ctg cgt ctt gat gat     192
Glu Lys Ser Ala Thr Glu Leu Ser Ala Lys Leu Leu Arg Leu Asp Asp
 20              25                  30                  35 ctg gtg tcc tta gag aat gac gta ttt gag acc aag aaa aag aga agc     240
Leu Val Ser Leu Glu Asn Asp Val Phe Glu Thr Lys Lys Lys Arg Ser
             40                  45                  50 ttc tct ggc ttt ggg tct ccc ctt gac aga ctc tca gct ggg tct gta     288
Phe Ser Gly Phe Gly Ser Pro Leu Asp Arg Leu Ser Ala Gly Ser Val
         55                  60                  65 gag cat aga ggg aaa caa agg aaa gca gta gat cat tca aaa aag cgg     336
Glu His Arg Gly Lys Gln Arg Lys Ala Val Asp His Ser Lys Lys Arg
     70                  75                  80 ttt ggt att ccc atg gat cgg att ggt aga aac cgg ctc tcc agt tcc     384
Phe Gly Ile Pro Met Asp Arg Ile Gly Arg Asn Arg Leu Ser Ser Ser
 85                  90                  95 aga ggc tga                                                         393
Arg Gly
100

<210> SEQ ID NO 4
<211> LENGTH: 130
<212> TYPE: PRT
<213> ORGANISM: Mus musculus

<400> SEQUENCE: 4

Met Leu Asp Trp Arg Leu Ala Ser Thr His Phe Ile Leu Ala Met Ile
            -25                 -20                 -15

Val Met Leu Trp Gly Ser Gly Lys Ala Phe Ser Val Asp Leu Ala Ser
        -10                  -5                  -1  1

Gln Glu Phe Gly Thr Ala Ser Leu Gln Ser Pro Pro Thr Ala Arg Glu
      5                  10                  15

Glu Lys Ser Ala Thr Glu Leu Ser Ala Lys Leu Leu Arg Leu Asp Asp
 20              25                  30                  35

Leu Val Ser Leu Glu Asn Asp Val Phe Glu Thr Lys Lys Lys Arg Ser
             40                  45                  50

Phe Ser Gly Phe Gly Ser Pro Leu Asp Arg Leu Ser Ala Gly Ser Val
         55                  60                  65

Glu His Arg Gly Lys Gln Arg Lys Ala Val Asp His Ser Lys Lys Arg
     70                  75                  80

Phe Gly Ile Pro Met Asp Arg Ile Gly Arg Asn Arg Leu Ser Ser Ser
 85                  90                  95

Arg Gly
100
```

<210> SEQ ID NO 5
<211> LENGTH: 19
<212> TYPE: DNA
<213> ORGANISM: Artificial Sequence
<220> FEATURE:
<223> OTHER INFORMATION: Oligonucleotide designed to act as primer for
      amplifying cDNA derived from mouse soleus muscle.

<400> SEQUENCE: 5
gggggtggac catcctcta                                                   19

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide designed to act as primer for
      amplifying cDNA derived from mouse soleus muscle.

<400> SEQUENCE: 6
cgcgcagctg taaacggtag                                                  20

<210> SEQ ID NO 7
<211> LENGTH: 249
<212> TYPE: DNA
<213> ORGANISM: Mus musculus

<400> SEQUENCE: 7
aggactctaa agttaggagc tctgacttct cacaagatgc tggactggag attggcaagt      60
acacacttca tcctggctat gattgtgatg ctgtggggct caggaaaggc attctctgtg     120
gacttagcat cacaggagtt tggaacagca agcttgcagt ctccacccac agccagagaa     180
gagaagtcag ccactgagct ttcggctaag ctcctgcgtc ttgatgatct ggtgtcctta     240
gagaatgac                                                             249

<210> SEQ ID NO 8
<211> LENGTH: 30
<212> TYPE: DNA
<213> ORGANISM: Artificial Sequence
<220> FEATURE:
<223> OTHER INFORMATION: Oligonucleotide designed to act as primer for
      amplifying full length mouse musculin cDNA.

<400> SEQUENCE: 8
tcctgagccc cacagcatca caatcatagc                                       30

<210> SEQ ID NO 9
<211> LENGTH: 19
<212> TYPE: DNA
<213> ORGANISM: Artificial Sequence
<220> FEATURE:
<223> OTHER INFORMATION: Oligonucleotide designed to act as primer for
      amplifying full length mouse musculin cDNA.

<400> SEQUENCE: 9
ccttgacaga ctctcagct                                                   19

<210> SEQ ID NO 10
<211> LENGTH: 1154
<212> TYPE: DNA
<213> ORGANISM: Mus musculus

<400> SEQUENCE: 10
gagagagaga gagagagaga gagagagaga gagagttggt gaaatgttcc gctgaaaatc      60

```
tgtggaactg atgtaagaga aagcaacgac aggggttgga gtaagtggag tagaactgag      120
actataaaaa cacagaaaga aactcgcatc agggctaagt ttgggataag ctgcaggcag      180
gactctaaag ttaggagctc tgacttctca caagatgctg gactggagat tgcaagtac      240 acacttcatc ctggctatga ttgtgatgct gtggggctca ggaaaggcat tctctgtgga      300
cttagcatca caggagtttg gaacagcaag cttgcagtct ccacccacag ccagagaaga      360
gaagtcagcc actgagcttt cggctaagct cctgcgtctt gatgatctgg tgtccttaga      420
gaatgacgta tttgagacca agaaaaagag aagcttctct ggctttgggt ctccccttga      480
cagactctca gctgggtctg tagagcatag agggaaacaa aggaaagcag tagatcattc      540
aaaaaagcgg tttggtattc ccatggatcg gattggtaga aaccggctct ccagttccag      600
aggctgatgg attcttattg tgcgacttac ttgtgtgaga tggcacagaa ctatagaaga      660
cacttcagtg aagttcacta ccccttttgt caaggaattg gcctttcgca aaccttccca      720
aagcttgatc ctccccagac catcacgtca tagtgttgct gtggttttag ttgagttgtg      780
cagatcattt cagtgcatgg atatctctga aagtattttt caatgattcc caaattgtaa      840
cgtggcccct gaacctactt tttttaaaca gcagaccaat ataatgcatt ctcttgccat      900
taatattttc acatttcagt taatcaatgt gctttctaga aacctagtgt ttgaagatct      960
gatgatctaa agaaatcaga aatgagcaca tggtgattta tataggtttc tttagttttt     1020
ctgaggtttg tcgaattgtt gtaaacttca acttcaagct tagaaaaaag acattacatg     1080
agtgtttgct tcaactgtgt cagaaggcaa ataaattttg agaaaccaaa aaaaaaaaa      1140 aaaaaaaaaa aaaa                                                       1154

<210> SEQ ID NO 11
<211> LENGTH: 28
<212> TYPE: DNA
<213> ORGANISM: Artificial Sequence
<220> FEATURE:
<223> OTHER INFORMATION: Oligonucleotide designed to act as primer for
      amplifying full length human musculin cDNA.

<400> SEQUENCE: 11
gactgtgggt gttgactgca catctatg                                          28

<210> SEQ ID NO 12
<211> LENGTH: 28
<212> TYPE: DNA
<213> ORGANISM: Artificial Sequence
<220> FEATURE:
<223> OTHER INFORMATION: Oligonucleotide designed to act as primer for
      amplifying full length human musculin cDNA.

<400> SEQUENCE: 12
ctgatctttc acgagatgct ggactgga                                          28

<210> SEQ ID NO 13
<211> LENGTH: 1655
<212> TYPE: DNA
<213> ORGANISM: Homo sapiens
<220> FEATURE:
<221> NAME/KEY: misc_feature
<222> LOCATION: (763)..(763)
<223> OTHER INFORMATION: n stands for unidentified base.
<220> FEATURE:
<221> NAME/KEY: misc_feature
<222> LOCATION: (965)..(965)
<223> OTHER INFORMATION: n stands for unidentified base.
<220> FEATURE:
<221> NAME/KEY: misc_feature
```

```
<222> LOCATION: (1032)..(1032)
<223> OTHER INFORMATION: n stands for unidentified base.
<220> FEATURE:
<221> NAME/KEY: misc_feature
<222> LOCATION: (1033)..(1033)
<223> OTHER INFORMATION: n stands for unidentified base.
<220> FEATURE:
<221> NAME/KEY: misc_feature
<222> LOCATION: (1043)..(1043)
<223> OTHER INFORMATION: n stands for unidentified base.
<220> FEATURE:
<221> NAME/KEY: misc_feature
<222> LOCATION: (1075)..(1075)
<223> OTHER INFORMATION: n stands for unidentified base.
<220> FEATURE:
<221> NAME/KEY: misc_feature
<222> LOCATION: (1080)..(1080)
<223> OTHER INFORMATION: n stands for unidentified base.
<220> FEATURE:
<221> NAME/KEY: misc_feature
<222> LOCATION: (1113)..(1113)
<223> OTHER INFORMATION: n stands for unidentified base.
<220> FEATURE:
<221> NAME/KEY: misc_feature
<222> LOCATION: (1138)..(1138)
<223> OTHER INFORMATION: n stands for unidentified base.
<220> FEATURE:
<221> NAME/KEY: misc_feature
<222> LOCATION: (1235)..(1235)
<223> OTHER INFORMATION: n stands for unidentified base.
<220> FEATURE:
<221> NAME/KEY: misc_feature
<222> LOCATION: (1238)..(1238)
<223> OTHER INFORMATION: n stands for unidentified base.
<220> FEATURE:
<221> NAME/KEY: misc_feature
<222> LOCATION: (1265)..(1265)
<223> OTHER INFORMATION: n stands for unidentified base.
<220> FEATURE:
<221> NAME/KEY: misc_feature
<222> LOCATION: (1277)..(1277)
<223> OTHER INFORMATION: n stands for unidentified base.
<220> FEATURE:
<221> NAME/KEY: misc_feature
<222> LOCATION: (1280)..(1280)
<223> OTHER INFORMATION: n stands for unidentified base.
<220> FEATURE:
<221> NAME/KEY: misc_feature
<222> LOCATION: (1291)..(1291)
<223> OTHER INFORMATION: n stands for unidentified base.
<220> FEATURE:
<221> NAME/KEY: misc_feature
<222> LOCATION: (1301)..(1301)
<223> OTHER INFORMATION: n stands for unidentified base.
<220> FEATURE:
<221> NAME/KEY: misc_feature
<222> LOCATION: (1328)..(1328)
<223> OTHER INFORMATION: n stands for unidentified base.
<220> FEATURE:
<221> NAME/KEY: misc_feature
<222> LOCATION: (1347)..(1347)
<223> OTHER INFORMATION: n stands for unidentified base.
<220> FEATURE:
<221> NAME/KEY: misc_feature
<222> LOCATION: (1366)..(1366)
<223> OTHER INFORMATION: n stands for unidentified base.
<220> FEATURE:
<221> NAME/KEY: misc_feature
<222> LOCATION: (1454)..(1454)
<223> OTHER INFORMATION: n stands for unidentified base.
<220> FEATURE:
<221> NAME/KEY: misc_feature
<222> LOCATION: (1553)..(1553)
<223> OTHER INFORMATION: n stands for unidentified base.
<220> FEATURE:
<221> NAME/KEY: misc_feature
<222> LOCATION: (1580)..(1580)
<223> OTHER INFORMATION: n stands for unidentified base.
<220> FEATURE:
```

<221> NAME/KEY: misc_feature
<222> LOCATION: (1625)..(1625)
<223> OTHER INFORMATION: n stands for unidentified base.

<400> SEQUENCE: 13

```
acgcgggag ggctgagttt tggagaaact gcagagacag tactctaaag ttagaatctc      60
ctgatctttc acgagatgct ggactggaga ttggcaagtg cacatttcat cctggctgtg    120
acactgacac tgtggagctc aggaaaagtc ctctcagtag atgtaacaac aacagaggcc    180
tttgattctg gagtcataga gtgcagtca acacccacag tcagggaaga gaaatcagcc    240
actgacctga cagcaaaact cttgcttctt gatgaattgg tgtccctaga aaatgatgtg    300
attgagacaa agaagaaaag gagtttctct ggttttgggt ctcccttga cagactctca    360
gctggctctg tagatcacaa aggtaaacag aggaaagtag tagatcatcc aaaaaggcga    420
tttggtatcc ccatggatcg gattggtaga aaccggcttt caaattccag aggctaattg    480
attccaatta tgcaacttcc ttgggtgaaa tgtcacagca atatggaaga tgcttcactg    540
aagttattca cacttcttaa tgattaaact tttaaggaac tgaccttctg caaatccttt    600
ccaaagcttg aacttcagtc catcacatta cggcattgtt acagcttcaa ttaaattgtg    660
taaatcattt tgatgcacgt acattttaaa attatatatt ttaattattc aagaatggtt    720
aacttcccct taaaccttac ttttaaaata ataattaaat acncaataca gtgaaatgcc    780
ttctgtatgg atttaccatg cacatgtttg gagtccaaag aaataataac caaagacaga    840
atttgccttc tgtaaaattt tagttataaa tctggcccat tattgggaa tgaaggaaag    900
gcaatgcctg tgtatttttc tggtgaggaa cttttccctt tccccggaat tccaatttt     960
tcccngaagg cctggatccg ggaataaatt atgaaaatta gggcttccct tttccaaatt   1020
ccaaagtttt cnngtccatg ttncagaaaa attaaaaaca ccagcccca agggnagccn   1080
tatttgactt tagaattaag gaaggggaa ggnccattac tcatttggtc aaaacttnga   1140
tatcactttg tccctaaaa accttcccat tttttttaaa ttctgccagg ttaagagcag   1200
taggtgtctc attaggaggg gaggtaacgc tcacncanag ggtaaaaatg aaagtaggag   1260
ggaantcaaa ggaattnccn ccagaactgg ntaggcccag ntaagcacac atcattttag   1320
gctcagtnca cttcagcata gtacaangtg atcttttgga tatcgnggat taatctaaga   1380
aactgtttac tgtgtttcat atattggctt attgggcttc aattgtctta ttatccttaa   1440
taagccaatt gaangagcat aatgattttg agaatgattt cttaaaaatc attcagatta   1500
tttttgaatg acttattaaa acataagttt tcgtattgta gaaaactcag ttntcagtaa   1560
taactatgat gttactgtan gcttggacac ataggtccat tgtgcacttg gatatacttt   1620
gaaanccccc aaaaaaaaaa aaaaaaaaaa aaaaa                               1655
```

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide designed to act as primer for amplifying mouse musculin cDNA fragment.

<400> SEQUENCE: 14

```
tgtggactta gcatcacagg                                                  20
```

<210> SEQ ID NO 15
<211> LENGTH: 19
<212> TYPE: DNA

<213> ORGANISM: Artificial Sequence
<220> FEATURE:
<223> OTHER INFORMATION: Oligonucleotide designed to act as primer for
     amplifying mouse musculin cDNA fragment.

<400> SEQUENCE: 15
ccttgacaga ctctcagct                                                      19

<210> SEQ ID NO 16
<211> LENGTH: 27
<212> TYPE: DNA
<213> ORGANISM: Artificial Sequence
<220> FEATURE:
<223> OTHER INFORMATION: Oligonucleotide designed to act as primer for
     amplifying full length rat SS169 cDNA.

<400> SEQUENCE: 16
gctggactgg agattggcaa gtgcaca                                              27

<210> SEQ ID NO 17
<211> LENGTH: 28
<212> TYPE: DNA
<213> ORGANISM: Artificial Sequence
<220> FEATURE:
<223> OTHER INFORMATION: Oligonucleotide designed to act as primer for
     amplifying full length rat SS169 cDNA.

<400> SEQUENCE: 17
ctcctggcta tgatcctgat gctgtggg                                             28

<210> SEQ ID NO 18
<211> LENGTH: 26
<212> TYPE: DNA
<213> ORGANISM: Artificial Sequence
<220> FEATURE:
<223> OTHER INFORMATION: Oligonucleotide designed to act as primer for
     amplifying full length rat SS169 cDNA.

<400> SEQUENCE: 18
aaggcattct ccgtggactt agcatc                                               26

<210> SEQ ID NO 19
<211> LENGTH: 23
<212> TYPE: DNA
<213> ORGANISM: Artificial Sequence
<220> FEATURE:
<223> OTHER INFORMATION: Oligonucleotide designed to act as primer for
     amplifying full length rat SS169 cDNA.

<400> SEQUENCE: 19
ctctggcttc gggtctcccc ttg                                                  23

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide designed to act as primer for
     amplifying cDNA derived from rat gastrocunemius muscle.

<400> SEQUENCE: 20
atgctggact ggagattggc                                                      20

<210> SEQ ID NO 21
<211> LENGTH: 20
<212> TYPE: DNA
<213> ORGANISM: Artificial Sequence

```
<220> FEATURE:
<223> OTHER INFORMATION: Oligonucleotide designed to act as primer for
      amplifying cDNA derived from rat gastrocunemius muscle.

<400> SEQUENCE: 21
tcagcccctg gaactggaga                                                     20

<210> SEQ ID NO 22
<211> LENGTH: 399
<212> TYPE: DNA
<213> ORGANISM: Rattus norvegicus
<220> FEATURE:
<221> NAME/KEY: CDS
<222> LOCATION: (1)..(396)
<220> FEATURE:
<221> NAME/KEY: sig_peptide
<222> LOCATION: (1)..(87)
<220> FEATURE:
<221> NAME/KEY: mat_peptide
<222> LOCATION: (88)..(396)

<400> SEQUENCE: 22 atg ctg gac tgg aga ttg gca agt gca cac ttc ctc ctg gct atg atc            48
Met Leu Asp Trp Arg Leu Ala Ser Ala His Phe Leu Leu Ala Met Ile
            -25                 -20                 -15 ctg atg ctg tgg ggc tca gga aag gca ttc tcc gtg gac tta gca tca            96
Leu Met Leu Trp Gly Ser Gly Lys Ala Phe Ser Val Asp Leu Ala Ser
        -10                  -5              -1   1 gag gcc tcc gag ttt gga gca gaa agc ttg cag tcc cca ccc aca acc           144
Glu Ala Ser Glu Phe Gly Ala Glu Ser Leu Gln Ser Pro Pro Thr Thr
     5                   10                  15 aga gaa gag aag tca gcc acg gag ctt gca gct aag ctc ctg ctt ctt           192
Arg Glu Glu Lys Ser Ala Thr Glu Leu Ala Ala Lys Leu Leu Leu Leu
 20                  25                  30                  35 gat gat ctg gtg tcc ttg gag aat gat gtg ttt gag acc aag aag aag           240
Asp Asp Leu Val Ser Leu Glu Asn Asp Val Phe Glu Thr Lys Lys Lys
                 40                  45                  50 aga agc ttc tct ggc ttc ggg tct ccc ctt gac aga ctc tcg gct ggg           288
Arg Ser Phe Ser Gly Phe Gly Ser Pro Leu Asp Arg Leu Ser Ala Gly
             55                  60                  65 tct gta gag cat aga ggg aaa caa agg aga gta gtt gat cat tca aaa           336
Ser Val Glu His Arg Gly Lys Gln Arg Arg Val Val Asp His Ser Lys
         70                  75                  80 aag cga ttt ggt att ccc atg gat cga att ggt aga aac cgt ctc tcc           384
Lys Arg Phe Gly Ile Pro Met Asp Arg Ile Gly Arg Asn Arg Leu Ser
     85                  90                  95 agt tcc agg ggc tga                                                       399
Ser Ser Arg Gly
100

<210> SEQ ID NO 23
<211> LENGTH: 132
<212> TYPE: PRT
<213> ORGANISM: Rattus norvegicus

<400> SEQUENCE: 23

Met Leu Asp Trp Arg Leu Ala Ser Ala His Phe Leu Leu Ala Met Ile
            -25                 -20                 -15

Leu Met Leu Trp Gly Ser Gly Lys Ala Phe Ser Val Asp Leu Ala Ser
        -10                  -5              -1   1

Glu Ala Ser Glu Phe Gly Ala Glu Ser Leu Gln Ser Pro Pro Thr Thr
     5                   10                  15

Arg Glu Glu Lys Ser Ala Thr Glu Leu Ala Ala Lys Leu Leu Leu Leu
```

-continued

```
                20                  25                  30                  35
Asp Asp Leu Val Ser Leu Glu Asn Asp Val Phe Glu Thr Lys Lys Lys
                    40                  45                  50

Arg Ser Phe Ser Gly Phe Gly Ser Pro Leu Asp Arg Leu Ser Ala Gly
                55                  60                  65

Ser Val Glu His Arg Gly Lys Gln Arg Arg Val Val Asp His Ser Lys
            70                  75                  80

Lys Arg Phe Gly Ile Pro Met Asp Arg Ile Gly Arg Asn Arg Leu Ser
        85                  90                  95

Ser Ser Arg Gly
100

<210> SEQ ID NO 24
<211> LENGTH: 24
<212> TYPE: DNA
<213> ORGANISM: Artificial Sequence
<220> FEATURE:
<223> OTHER INFORMATION: Oligonuclotide designed to act as primer for
      amplifying rat SS169 cDNA fragment.

<400> SEQUENCE: 24
gatgatctgg tgtccttgga gaat                                              24

<210> SEQ ID NO 25
<211> LENGTH: 22
<212> TYPE: DNA
<213> ORGANISM: Artificial Sequence
<220> FEATURE:
<223> OTHER INFORMATION: Oligonucleotide designed to act as primer for
      amplifying rat SS169 cDNA fragment.

<400> SEQUENCE: 25
tctacagacc cagccgagag tc                                                22
```